US012636444B2

(12) United States Patent
Giri

(10) Patent No.: US 12,636,444 B2
(45) Date of Patent: *May 26, 2026

---

(54) MICROFLUIDIC PLATFORM FOR SHEAR-LESS AEROSOLIZATION OF LIPID NANOPARTICLES FOR MESSENGER RNA INHALATION

(71) Applicant: RARE AIR HEALTH, INC., Corvallis, OR (US)

(72) Inventor: Manish Giri, Milwaukie, OR (US)

(73) Assignee: RARE AIR HEALTH, INC., Corvallis, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/987,781

(22) Filed: Dec. 19, 2024

(65) Prior Publication Data

US 2025/0205438 A1      Jun. 26, 2025

Related U.S. Application Data

(60) Provisional application No. 63/614,049, filed on Dec. 22, 2023.

(51) Int. Cl.
A61M 11/04 (2006.01)
A61M 15/00 (2006.01)

(52) U.S. Cl.
CPC ...... A61M 11/042 (2014.02); A61M 15/0001 (2014.02); A61M 2205/0244 (2013.01); A61M 2205/3368 (2013.01)

(58) Field of Classification Search
CPC ........... A61M 11/042; A61M 15/0001; A61M 2205/0244; A61M 2205/3368;
(Continued)

(56) References Cited

U.S. PATENT DOCUMENTS 9,174,445 B1 * 11/2015 Prati ..................... B41J 2/14072
9,956,360 B2 * 5/2018 Germinario .......... A61M 11/005
(Continued)

FOREIGN PATENT DOCUMENTS

CN       110 477 452       11/2019
EP        3569275 A1 * 11/2019 ............... H05B 3/42
EP        4 014 773        6/2022

OTHER PUBLICATIONS

Miao et al. Optimization of formulation and atomization of lipid nanoparticles for the inhalation of mRNA. International Journal of Pharmaceutics 640 (2023) 123050 Accessed on Oct. 15, 2025. (Year: 2023).*

(Continued)

*Primary Examiner* — Kendra D Carter
*Assistant Examiner* — Maap Ellabib
(74) *Attorney, Agent, or Firm* — KNOBBE, MARTENS, OLSON & BEAR, LLP

(57) ABSTRACT

Leveraging the extensive surface area of the lungs for gene therapy, inhalation route offers distinct advantages for delivery. Clinical nebulizers that employ vibrating mesh technology are the standard choice for converting liquid medicines into aerosols. However, they have limitations when it comes to delivering mRNA through inhalation, including severe damage to nanoparticles due to shearing forces. A microfluidic aerosolization platform (MAP) can preserves the structural and physicochemical integrity of lipid nanoparticles, enabling safe and efficient mRNA delivery to the respiratory system. Results demonstrated the superiority of the novel microfluidic aerosolizer over the conventional vibrating mesh nebulizer, as it avoided problems such as particle aggregation, loss of mRNA encapsulation, and deformation of nanoparticle morphology. Notably, aerosolized nanoparticles generated by the microfluidic aerosolization platform led to enhanced transfection efficiency (Continued)

across various cell lines. In vivo experiments with mice that inhaled these aerosolized nanoparticles revealed successful, lung-specific mRNA transfection without observable signs of toxicity. This pioneering MAP represents a significant advancement for the pulmonary gene therapy, enabling precise and effective delivery of aerosolized nanoparticles.

21 Claims, 40 Drawing Sheets

(58) Field of Classification Search
CPC A61M 11/00; A61M 11/005; A61M 15/0085; A61M 11/001; A61M 2205/502; A61M 15/0003; A61M 15/0065; A61M 2205/8206; A61M 15/025; A61K 39/39; A61K 2039/53; A61K 2039/55555; A61P 11/00
See application file for complete search history.

(56) References Cited

U.S. PATENT DOCUMENTS

| | | | | |
|---|---|---|---|---|
| 2004/0100532 A1* | 5/2004 | Silverbrook | ......... | B41J 2/04588 |
| | | | | 347/57 |
| 2005/0172957 A1* | 8/2005 | Childers | .............. | A61M 11/001 |
| | | | | 128/200.23 |
| 2006/0060191 A1* | 3/2006 | Yang | ................. | A61M 15/0065 |
| | | | | 128/200.14 |
| 2014/0187969 A1 | 7/2014 | Hunter et al. | | |
| 2018/0125989 A1* | 5/2018 | DeRosa | ............. | A61K 48/0008 |
| 2022/0142923 A1* | 5/2022 | Casimiro | ............... | A61K 47/02 |
| 2025/0177668 A1* | 6/2025 | Verhoeven | ........... | A61M 11/001 |

OTHER PUBLICATIONS

Akin Akinc et al., "Targetd Delivery of RNAi Therapeutics with Endogenous and Exogenous Ligand-Based Mechanisms" Am. Sooc. Gene & Cell Therapy Jul. 2010.

Alexandra Suberi et al., "Polymer nanoparticles deliver mRNA to the lung for mucosal vaccination" Sci. Transl. Med. 15, eabq0603 (2023) Aug. 16, 2023.

Allen Y. Jiang et al., "Combinatorial development of nebulized mRNA delivery formulations for the lungs" Nature Nanotechnology | vol. 19 | Mar. 2024 | 364-375.

Asha Kumari Patel et al., "Inhaled Nanoformulated mRNA Polyplexes for Protein Production in Lung Epithelium" Adv. Mater. 2019, 31, 1805116.

Bart R. Anderson, et al., "Incorporation of pseudouridine into mRNA enhances translation by diminishing PKR activation" Nucleic Acids Research, 2010, vol. 38, No. 17 5884-5892.

Bowen Li et al., "Combinatorial design of nanoparticles for pulmonary mRNA delivery and genome editing" Nature Biotechnology | vol. 41 | Oct. 2023 | 1410-1415 1410.

Ema Robinson, et al., "Lipid Nanoparticle-Delivered Chemically Modified mRNA Restores Chloride Secretion in Cystic Fibrosis" Molecular Therapy vol. 26 No. 8 Aug. 2018 The American Society of Gene and Cell Therapy.

Eric W. F. W. Alton, M.D. et al., "A Phase I/IIa Safety and Efficacy Study of Nebulized Liposome-mediated Gene Therapy for Cystic Fibrosis Supports a Multidose Trial" American Journal of Respiratory and Critical Care Medicine vol. 192 No. 11 | Dec. 1, 2015.

Evalyne M Jansen, et al., "Are inhaled mRNA vaccines safe and effective? A review of preclinical studies" Expert Opinion on Drug Delivery 2022, vol. 19, No. 11, 1471-1485.

Hao Miao et al., "Optimization of formulation and atomization of lipid nanoparticles for the inhalation of mRNA" International Journal of Pharmaceutics 640 (2023) 123050.

Jack Grubbs et al., "Comparison of laser diffraction and image analysis techniques for particle size-shape characterization in additive manufacturing applications" Powder Technology 391 (2021) 20-33.

Jeonghwan Kim et al., "Self-assembled mRNA vaccines" Advanced Drug Delivery Reviews 170 (2021) 83-112.

Jeonghwan Kim et al. "Rapid Generation of Circulating and Mucosal Decoy Human ACE2 using mRNA Nanotherapeutics for the Potential Treatment of SARS-CoV-2" Adv. Sci. 2022, 9, 2202556.

Jeonghwan Kim et al. "Strategies for non-viral vectors targeting organs beyond the liver" Nature Nanotechnology | vol. 19 | Apr. 2024 | 428-447.

Jeonghwan Kim et al., "Engineering Lipid Nanoparticles for Enhanced Intracellular Delivery of mRNA through Inhalation" ACS Nano 2022, 16, 14792-14806.

Jeonghwan Kim et al., "Naturally Derived Membrane Lipids Impact Nanoparticle-Based Messenger RNA Delivery" Cellular and Molecular Bioengineering, vol. 13, No. 5, Oct. 2020 pp. 463-474.

Julian D. Gillmore, M.D., Ph.D., et al., "CRISPR-Cas9 In Vivo Gene Editing for Transthyretin Amyloidosis" The New England Journal of Medicine 2021;385:493-502.

Katalin Karikó et al. "Incorporation of Pseudouridine Into mRNA Yields Superior Nonimmunogenic Vector With Increased Translational Capacity and Biological Stability" Molecular Therapy vol. 16 No. 11, 1833-1840 Nov. 2008.

Katalin Karikó et al. "mRNA Is an Endogenous Ligand for Toll-like Receptor 3" vol. 279, No. 13, Issue of Mar. 26, pp. 12542-12550, 2004.

Katalin Karikó et al. "Suppression of RNA Recognition by Toll-like Receptors: The Impact of Nucleoside Modification and the Evolutionary Origin of RNA" Immunity, vol. 23, 165-175, Aug. 2005.

Katherine McMahan, et al., "Mucosal boosting enhances vaccine protection against SARS-CoV-2 in macaques" Nature | vol. 626 | Feb. 8, 2024.

Keishi Kishimoto et al., "Mammalian tracheal development and reconstruction: insights from in vivo and in vitro studies" The Company of Biologists Ltd | Development (2021) 148, dev198192. doi:10.1242/dev.198192.

Konrad Thorsteinsson, et al., "FRET-Based Assay for the Quantification of Extracellular Vesicles and Other Vesicles of Complex Composition" Anal. Chem. 2020, 92, 15336-15343.

Laura Rotolo et al, "Species-agnostic polymeric formulations for inhalable messenger RNA delivery to the lung" Nature Materials | vol. 22 | Mar. 2023 | 369-379.

Marek Kloczewiak et al., "A Biopharmaceutical Perspective on Higher-Order Structure and Thermal Stability of mRNA Vaccines" Mol. Pharmaceutics 2022, 19, 2022-2031.

Melissa P. Lokugamage et al., "Optimization of lipid nanoparticles for the delivery of nebulized therapeutic mRNA to the lungs" Nature Biomedical Engineering | vol. 5 | Sep. 2021 | 1059-1068.

Michael Y.T. Chow et al., "Inhaled RNA Therapy: From Promise to Reality" Trends in Pharmacological Sciences, Oct. 2020, vol. 41, No. 10.

Nathan M Belliveau et al., "Microfluidic Synthesis of Highly Potent Limit-size Lipid Nanoparticles for In Vivo Delivery of siRNA" Molecular Therapy-Nucleic Acids (2012) 1, e37.

Ngoc Duy Le et al, "Antiangiogenic Therapeutic mRNA Delivery Using Lung-Selective Polymeric Nanomedicine for Lung Cancer Treatment" ACS Nano 2024, 18, 8392-8410.

Qiang Cheng et al., "Selective organ targeting (SORT) nanoparticles for tissue-specific mRNA delivery and CRISPR-Cas gene editing" Nat Ure Nanot echnolo gy | vol. 15 | Apr. 2020 | 313-320.

Qiangqiang Liu et al., "Accurate Stereo-Vision-Based Flying Droplet Volume Measurement Method" IEEE Transactions on Instrumentation and Measurement, vol. 71, 2022.

Sarah J. Shepherd et al., "Microfluidic formulation of nanoparticles for biomedical applications" Biomaterials 274 (2021) 120826.

Sarah J. Shepherd, et al., "Scalable mRNA and siRNA Lipid Nanoparticle Production Using a Parallelized Microfluidic Device" Nano Lett. 2021, 21, 5671-5680.

Sean A. Dilliarda et al., "On the mechanism of tissue-specific mRNA delivery by selective organ targeting nanoparticles" PNAS 2021 Vol. 118 No. 52 e2109256118.

Shuai Liu et al., "Membrane-destabilizing ionizable phospholipids for organ-selective mRNA delivery and CRISPR-Cas gene editing" Nat Ure Materials | vol. 20 | May 2021 | 701-710.

(56) References Cited

OTHER PUBLICATIONS

Teresa Coelho, M.D. et al., "Safety and Efficacy of RNAi Therapy for Transthyretin Amyloidosis" The New England Journal of Medicine 369;9 nejm.org Aug. 29, 2013.

Xucheng Hou1 et al., "Lipid nanoparticles for mRNA delivery" 1078 | Dec. 2021 | vol. 6.

Yulia Eygeris et al., "Chemistry of Lipid Nanoparticles for RNA Delivery" Acc. Chem. Res. 2022, 55, 2-12.

Yulia Eygeris et al., "Thiophene-based lipids for mRNA delivery to pulmonary and retinal tissues" PNAS 2024 vol. 121 No. 11 e2307813120.

International Search Report and Written Opinion mailed Apr. 22, 2025 in International Application No. PCT/US2024/060998, in 27 pages.

Jeonghwan Kim, Antony Jozić, Elissa Bloom, Brian Jones, Michael Marra, Namratha Turuvekere Vittala Murthy, Yulia Eygeris, and Gaurav Sahay; "Microfluidic Platform Enables Shearless Aerosolization of Lipid Nanoparticles for mRNA Inhalation." *ACS Nano* 2024 18 (17), 11335-11348. DOI: 10.1021/acsnano.4c00768.

\* cited by examiner

Bubble Direction

Nozzle Layer

Protective
Cavitation
Dielectric
Electrode
Heater
Film

Microfluidic
Chamber Layer

Thin Films

Silicon Substrate Layer

Thermal
Region

Thick Film

Thin Films

Silicon
Substrate Layer

Bubble

10 μm

Aerosol Containing mRNA-Loaded LNP

1. Bubble Nucleation

2. Bubble Growth

3. Drop Ejected

4. Drop Break Off

Refill

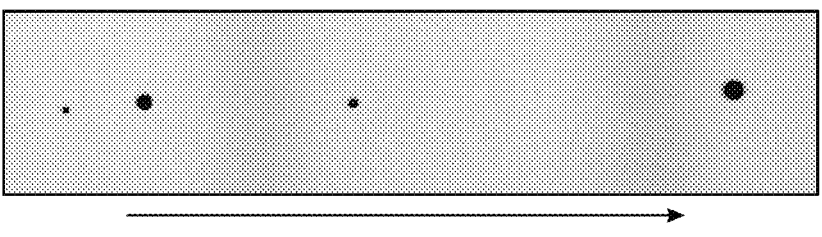
FIG. 2A
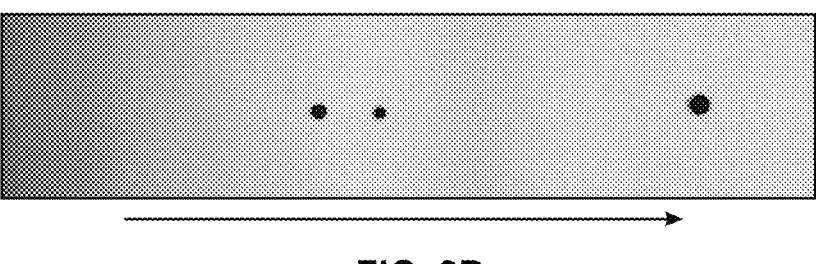
FIG. 2B
| Frequency: 1 kHz | | |
|---|---|---|
| Volume (pL) | % Volume | Diameter (μm) |
| 3.8 | 59% | 19.4 |
| 0.5 | 8% | 9.9 |
| 1.9 | 30% | 15.4 |
| 0.2 | 3% | 7.3 |
| 6.4 | 100% | - |
FIG. 2C

| Frequency: 15 kHz | | |
|---|---|---|
| Volume (pL) | % Volume | Diameter (μm) |
| 3.8 | 72% | 19.4 |
| 0.6 | 11% | 10.5 |
| 0.9 | 17% | 12.0 |
| 5.3 | 100% | - |

1) mRNA Only
2) LNP / mRNA: Untreated
3) LNP / mRNA: Triton X-100
4) LNP / mRNA: Vibrating Mesh
5) LNP / mRNA: Microfluidic

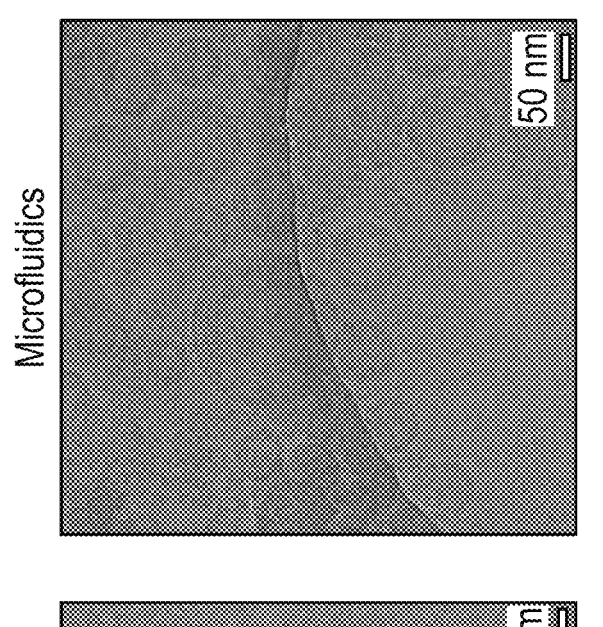
Microfluidics
50 nm
FIG. 4C
Vibrating Mesh
50 nm
FIG. 4B
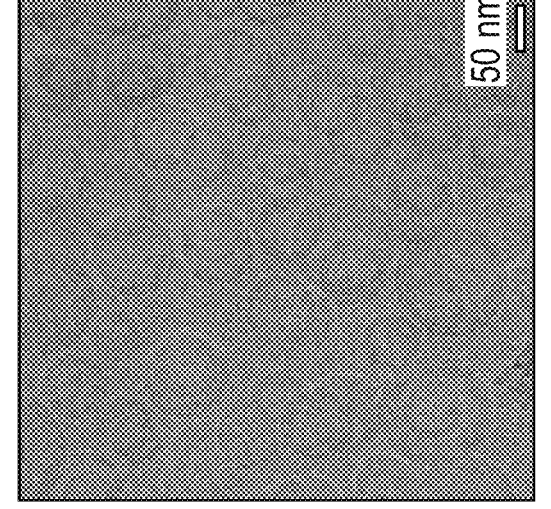
LNP Solution
50 nm
FIG. 4A

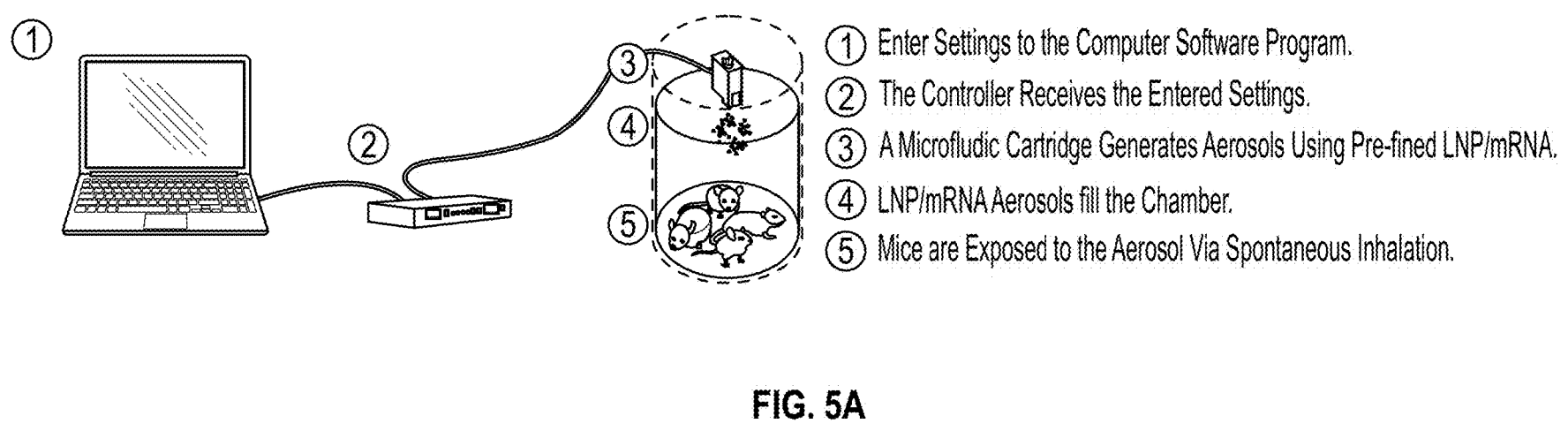

① Enter Settings to the Computer Software Program.

② The Controller Receives the Entered Settings.

③ A Microfludic Cartridge Generates Aerosols Using Pre-fined LNP/mRNA.

④ LNP/mRNA Aerosols fill the Chamber.

⑤ Mice are Exposed to the Aerosol Via Spontaneous Inhalation.

FIG. 5A

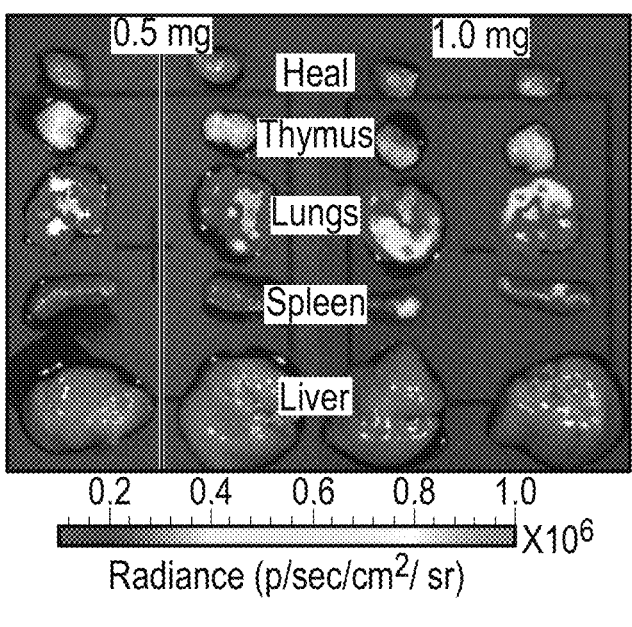
FIG. 5D
FIG. 5E
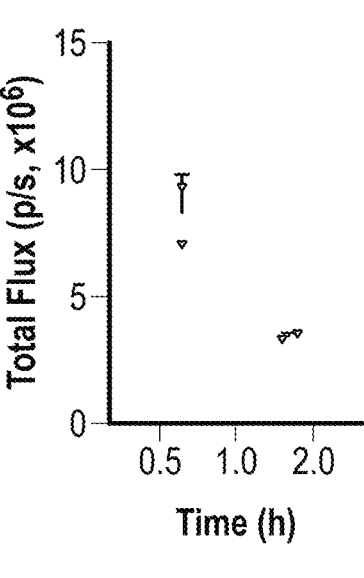
FIG. 5F
FIG. 5G

| Cumulant Results | Distribution Results | | | | | Undersize Results | |
|---|---|---|---|---|---|---|---|
| | Size (d.nm): | %Int | σ | %Pd | | Di (%) | Size (d.nm) |
| Z-Avg (nm): 81.03 | | | | | | | |
| Pd Index: 0.084   Peak 1: | 89.17 | 100.0 | 28.57 | 32.0 | | 50 | 84.7 |
| Pd (nm): 23.5   Peak 3: | 0.000 | 0.0 | 0.000 | 0 | | 90 | 132 |
| %Pd:29.0   Peak 3: | 0.000 | 0.0 | 0.000 | 0 | | 95 | 146 |
| Derived Kcps: 2616.9 | | | | | | | |

| | File | Dx(10) | Dx(50) | Dx(90) | Lot |
|---|---|---|---|---|---|
| —o— [N] | 20_Full | 9.65 | 13.80 | 20.76 | ... |
| – –□– – [N] | 30_Full | 9.49 | 13.88 | 21.75 | ... |
| ---◇--- [N] | 40_Full | 9.45 | 14.00 | 22.52 | ... |
| ---△--- [N] | 60_Full | 9.68 | 14.58 | 24.36 | ... |

[V]=Volume [N]=Number

| | File | Dx(10) | Dx(50) | Dx(90) | Lot |
|---|---|---|---|---|---|
| —o— [N] | 20_Spatial | 9.54 | 13.50 | 19.88 | ... |
| – –□– – [N] | 30_Spatial | 9.39 | 13.46 | 20.23 | ... |
| ---◇--- [N] | 40_Spatial | 9.24 | 13.35 | 20.48 | ... |
| ---△--- [N] | 60_Spatial | 9.09 | 13.44 | 21.60 | ... |

M=Vdume [N]=Number

|  | File | Dx(10) | Dx(50) | Dx(90) | Lot |
|---|---|---|---|---|---|
| ——○—— [N] | 20_Temporal | 9.05 | 12.89 | 19.19 | • • • |
| – –□– – [N] | 30_Temporal | 8.94 | 12.87 | 19.59 | • • • |
| ---◇--- [N] | 40_Temporal | 8.82 | 12.87 | 20.04 | • • • |
| ---△--- [N] | 60_Temporal | 8.79 | 12.99 | 20.91 | • • • |

[V]=Volume [N]=Number

| | File | Dx(10) | Dx(50) | Dx(90) | Lot |
|---|---|---|---|---|---|
| —o— [N] | 20_Full | 9.65 | 13.80 | 20.76 | ••• |
| – -□ – [N] | 20_Spatial | 9.54 | 13.50 | 19.88 | ••• |
| ---◇--- [N] | 20_Temporal | 9.05 | 12.89 | 19.19 | ••• |

[V]=Volume [N]=Number

| | File | Dx(10) | Dx(50) | Dx(90) | Lot |
|---|---|---|---|---|---|
| —o— [N] | 30_Full | 9.49 | 13.88 | 21.75 | ••• |
| – -□ – [N] | 30_Spatial | 9.39 | 13.46 | 20.23 | ••• |
| ---◇--- [N] | 30_Temporal | 8.94 | 12.87 | 19.59 | ••• |

[V]=Volume [N]=Number

| | File | Dx(10) | Dx(50) | Dx(90) | Lot |
|---|---|---|---|---|---|
| —o— [N] | 40_Full | 9.45 | 14.00 | 22.52 | ... |
| – -□- – [N] | 40_Spatial | 9.24 | 13.35 | 20.48 | ... |
| ---◇--- [N] | 40_Temporal | 9.82 | 12.87 | 20.04 | ... |

[V]=Volume [N]=Number

| | File | Dx(10) | Dx(50) | Dx(90) | Lot |
|---|---|---|---|---|---|
| —o— [N] | 60_Full | 9.68 | 14.58 | 24.36 | ... |
| – -□- – [N] | 60_Spatial | 9.09 | 13.44 | 21.60 | ... |
| ---◇--- [N] | 60_Temporal | 8.79 | 12.99 | 20.91 | ... |

[V]=Volume [N]=Number

| | File | Dx(10) | Dx(50) | Dx(90) | Lot |
|---|---|---|---|---|---|
| —o— [N] | 20_Full 1 | 10.52 | 14.87 | 21.87 | ... |
| – –□– – [N] | 20_Full 2 | 9.73 | 13.93 | 20.94 | ... |
| ---◇--- [N] | 20_Full 3 | 8.86 | 12.88 | 19.86 | ... |

[V]=Volume [N]=Number

| | File | Dx(10) | Dx(50) | Dx(90) | Lot |
|---|---|---|---|---|---|
| —o— [N] | 60_Full 1 | 11.16 | 16.59 | 27.05 | ... |
| – –□– – [N] | 60_Full 2 | 9.71 | 14.53 | 23.98 | ... |
| ---◇--- [N] | 60_Full 3 | 9.24 | 13.85 | 22.87 | ... |

[V]=Volume [N]=Number

| | File | Dx(10) | Dx(50) | Dx(90) | Lot |
|---|---|---|---|---|---|
| —○— [N] | 20_Spatial 1 | 10.33 | 14.37 | 20.66 | ••• |
| – –□– – [N] | 20_Spatial 2 | 9.36 | 13.33 | 19.83 | ••• |
| ---◇--- [N] | 20_Spatial 3 | 9.51 | 13.35 | 19.48 | ••• |

[V]=Volume [N]=Number

| | File | Dx(10) | Dx(50) | Dx(90) | Lot |
|---|---|---|---|---|---|
| —○— [N] | 60_Spatial 1 | 9.84 | 14.35 | 22.54 | ••• |
| – –□– – [N] | 60_Spatial 2 | 9.16 | 13.60 | 22.11 | ••• |
| ---◇--- [N] | 60_Spatial 3 | 8.76 | 13.02 | 20.99 | ••• |

[V]=Volume [N]=Number

| | File | Dx(10) | Dx(50) | Dx(90) | Lot |
|---|---|---|---|---|---|
| —○— [N] | 20_Temporal 1 | 9.76 | 13.58 | 19.63 | ••• |
| – –□ – [N] | 20_Temporal 2 | 8.81 | 12.63 | 19.04 | ••• |
| ---◇--- [N] | 20_Temporal 3 | 8.85 | 12.33 | 18.77 | ••• |

[V]=Volume [N]=Number

| | File | Dx(10) | Dx(50) | Dx(90) | Lot |
|---|---|---|---|---|---|
| —○— [N] | 60_Temporal 1 | 9.63 | 13.95 | 21.69 | ••• |
| – –□ – [N] | 60_Temporal 2 | 8.68 | 12.81 | 20.58 | ••• |
| ---◇--- [N] | 60_Temporal 3 | 8.54 | 12.71 | 20.74 | ••• |

[V]=Volume [N]=Number

| # | Samples |
|---|---------|
| 1 | mRNA Only |
| 2 | LNP Before Treatment |
| 3 | LNP + Triton X - 100 |
| 4 | LNP After Vibrating Mesh |
| 5 | LNP After Microfluidic Device |

1. LNP Solution
2. Vibrating Mesh
3. Microfluidic 0.2 0.4 0.6 0.8 1.0

$\times 10^6$

Radiance (p/sec/cm$^2$/sr)

MICROFLUIDIC PLATFORM FOR SHEAR-LESS AEROSOLIZATION OF LIPID NANOPARTICLES FOR MESSENGER RNA INHALATION

INCORPORATION BY REFERENCE TO ANY PRIORITY APPLICATIONS

The present application claims the benefit of priority to U.S. Provisional Patent Application No. 63/614,049 filed on Dec. 22, 2023, which is hereby expressly incorporated by reference in its entirety.

BACKGROUND OF THE INVENTION

Field

The present disclosure pertains to the field of medical aerosolization.

Description of the Related Art

The successful development of mRNA vaccines against SARS-COV-2 has transformed how the researchers and clinicians perceive the use of mRNA as a therapeutic tool. Previously considered a theoretical approach, it has now become a promising and feasible option for clinical applications. Particularly, mRNA has garnered significant attention in the field of pulmonology for its potential in treating inherited diseases, including cystic fibrosis (CF) and alpha-1 antitrypsin deficiency as well as in the field of vaccinology for intranasal vaccination approaches.

SUMMARY

In aspects, a microfluidic aerosolization system can provide delivery of a therapeutic media into a pulmonary airway. The microfluidic aerosolization system can include: a microfluidic chip having a plurality of microfluidic chambers and corresponding apertures; heat sources in the form of resistors in thermal communication with each of the microfluidic chambers, which may be individually addressable for drop ejection; a cartridge housing the microfluidic chip and multiple reservoirs holding the therapeutic media configured to deliver the therapeutic media into the microfluidic chambers; and a processor, configured to generate an activation pulse heating pattern; wherein the microfluidic chambers express a plurality of droplets in response to the activation pulse pattern.

In some examples, the chip is monolithically fabricated on a silicon base layer.

In some examples, the activation pulse heating pattern has a pulse range of between about 5 and about 40 volts and a timing range from about 0.1 microseconds to about 10 microseconds. In some examples, the heating pattern has a frequency of at least about 10 kHz.

In some examples, the chambers express droplets at a rate of at least about 5 million drops per second. In some examples, the microfluidic aerosolization system includes at least about 500 microfluidic chambers and corresponding apertures.

In some examples, at least some of the apertures have a diameter of no more than about 15 microns. In some examples, the cartridge contains a volume of the therapeutic media in one or multiple reservoirs. In some examples, the therapeutic media includes mRNA encapsulated within lipid nanoparticles. In some examples, the processor is configured to deliver the volume of media broken into a plurality of individual patient doses.

In some examples, the cartridge includes at least two reservoirs. In further examples, a first reservoir carries a first therapeutic media and a second reservoir carries a second, different media. In other further examples, each reservoir carries the same therapeutic media.

In some examples, at least one reservoir carries a buffer. In some examples, all apertures can be individually programmed using the activation pulse pattern in order to control at least one of drop size, drop size composition, drop ejection frequency and drop volume. In some examples, the processor can execute instructions to individually control pulse of each microfluidic chamber. In some examples, the processor can control at least one of drop size, drop size composition, drop ejection frequency and drop volume. In some examples, the processor is configured for simultaneous or sequential activation of the plurality of microfluidic chamber and apertures. In some examples, the processor can control the applied voltage and pulse width so that the heating pattern has a frequency ranging from 1 kHz to 15 kHz. In some examples, the processor can control the applied voltage and pulse width so that the heating pattern results in droplets having diameters ranging from 7.3 $\mu$m and 24.4 $\mu$m. In some examples, the processor can control the applied voltage and pulse width so that the heating pattern results in droplets having diameters ranging from 7.3 $\mu$m and 19.4 $\mu$m. In some examples, the processor can control the applied voltage and pulse width so that the heating pattern results in droplets having volumes ranging from 0.2 pL to 3.8 pL.

In some examples, the system includes a mouthpiece having a profile that is matched to the chip size to influence the shape of the plume as it is being ejected from the apertures.

In some examples, the therapeutic media includes a drug. In some further examples, the therapeutic media includes a small molecule drug. In some examples, the therapeutic media includes a biologically active agent. In some further examples, the biologically active agent includes mRNA. In yet further examples, the biologically active agent includes encapsulated mRNA.

In some examples, the processor can control the applied voltage and pulse width. In some examples, an applied voltage and pulse width results in the formation of a microbubble which nucleates, expands and collapses to eject a droplet of fluid in the microchamber. In some further examples, the applied voltage is less than about 5V and the pulse width is less than about 10 $\mu$s. In some further examples, the applied voltage includes a waveform that is at least one of square, saw tooth or sinusoidal. In some further examples, the applied voltage and pulse width results in the deflection of a micro-electro-mechanical membrane, which in term ejects a droplet of fluid in the microchamber. In some examples, individual chamber addressing pattern and ejection frequency are adjustable (e.g., by the processor) to regulate the plurality of droplets into a plume formation, the depth of droplet penetration into the pulmonary path and agglomeration of droplets in the plume.

In aspects, a pulmonary route method can deliver a therapeutic media. The method can include the steps of: introducing a therapeutic media into at least one microfluidic chamber having an aperture; and heating the microfluidic chamber to volatilize at least a fraction of the media and express at least one droplet through the aperture and into a pulmonary airway, where the aperture has a diameter of no more than about 20 microns.

In some examples, the aperture has a diameter of no more than about 15 microns. In some examples, the droplet has a diameter of no more than about 20 microns. In other examples, the droplet has a diameter of at least about 50 microns. In some examples, the method includes introducing the therapeutic media into at least about 100 microfluidic chambers. In further examples, the method includes introducing the biologically active media into at least about 500 microfluidic chambers. In yet further examples, the method includes expressing at least about 1 million droplets per second. In yet further examples, the method includes expressing at least about 5 million droplets per second. In some examples, the method includes using a processor to apply voltage and pulse width to the microfluidics chamber so that the heating pattern has a frequency ranging from 1 kHz to 15 kHz. In some examples, the method includes using a processor to apply voltage and pulse width to the microfluidics chamber so that the heating pattern results in droplets having diameters ranging from 7.3 μm and 24.4 μm. In some examples, the processor can control the applied voltage and pulse width so that the heating pattern results in droplets having diameters ranging from 7.3 μm and 19.4 μm. In some examples, the method includes using a processor to apply voltage and pulse width to the microfluidics chamber so that the heating pattern results in droplets having volumes ranging from 0.2 pL to 3.8 pL.

In some examples, the therapeutic media includes an mRNA vaccine. In further examples, the therapeutic media includes an mRNA vaccine encapsulated within lipid nanoparticles. In some examples, the therapeutic media includes a drug. In further examples, the therapeutic media includes a small molecule drug. In some examples, the therapeutic media includes a biologically active agent. In some examples, the biologically active agent includes mRNA. In some examples, the biologically active agent includes encapsulated mRNA.

In some examples, the method includes controlling heating of the microfluidic chamber using a processor executing instructions. In some examples, the processor can adjust the activation pulse pattern. In some examples, the processor can cause simultaneous or sequential activation of the plurality of microfluidic chamber and apertures. In some examples, all apertures can be individually programmed using the activation pulse pattern in order to control at least one of drop size, drop size composition, drop ejection frequency and drop volume.

BRIEF DESCRIPTION OF THE DRAWINGS

The following drawings and the associated descriptions are provided for illustrative purposes and do not limit the scope of the claims.

FIGS. 2A-2C shows a comparison of droplet formation from the microfluidic cartridge with 4-pL nozzles at three different frequencies, 1 kHz, 10 kHz, and 15 kHz.

FIG. 4A-4C are images of droplets of the untreated LNP/mRNA sample, the vibrating mesh nebulizer, and the microfluidic acrosolization system.

FIG. 5A is a cartoon diagram of a whole-body rodent inhalation system, which includes a 3 L container connected with the microfluidic aerosolization system.

FIGS. 5D and 5E show that the Nluc expressions in the mouse lungs were directly proportional to the dose of LNP/Nluc aerosolized.

FIGS. 5F and 5G show that luciferase expression was higher at 24 hours post-treatment compared to 48 hours post-treatment.

FIG. 26A shows inhalation of LNP/Nluc when 1 mg of mRNA was aerosolized. FIG. 26B shows inhalation of an equal volume of sterile PBS using the microfluidic platform.

DETAILED DESCRIPTION

Figure 1A:
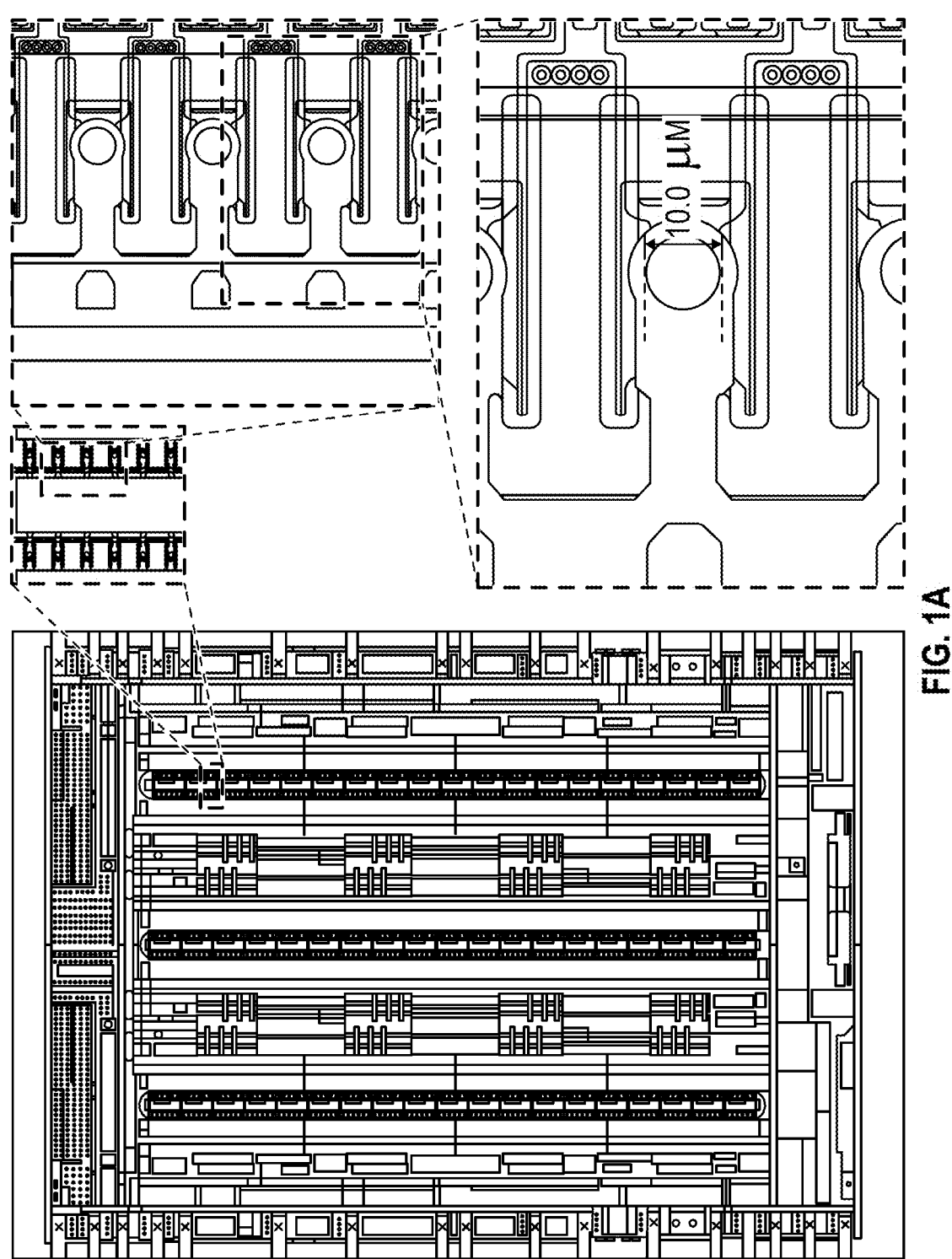
FIG. 1A illustrates views of a chip included in an example system.

The microfluidics aerosolizer of the present disclosure may avoid problems such as particle aggregation, loss of mRNA encapsulation, and deformation of nanoparticle morphology. Further, aerosolized nanoparticles generated by the microfluidic aerosolizer can increase transfection efficiency. The aerosolizer nanoparticles generated by the microfluidic aerosolizer may allow for successful, lung-specific mRNA transfection without observable signs of toxicity. The microfluidic aerosolizer may allow for pulmonary gene therapy, enabling precise and effective delivery of aerosolizer nanoparticles.

A significant challenge in clinical translation of mRNA-based therapeutic treatment lies in identifying a safe and effective delivery strategy. The recent progress in the development of novel nanoparticles capable of targeting the lungs following systemic administration shows great potential for lung-specific mRNA delivery. However, concerns regarding the potential risk of off-target delivery persist with these RNA vectors.

Given that many pulmonary diseases are closely linked to conditions in the pulmonary epithelial cells, the most direct, safe, and efficient method for administering mRNA therapies might be via inhalation. Inhalation allows for the therapy to reach high concentrations in the pulmonary epithelial tissues, enabling targeted and localized treatment for respiratory conditions while minimizing systemic exposure. This local administration holds significant promise for the treatment of the pulmonary system using mRNA therapies. Clinical trials based on inhalation-mediated mRNA delivery (NCT05712538 and NCT05737485) indicate the growing interest in this approach. However, inhaled mRNA therapy continues to encounter challenges related to the shearing damage caused by the inhalers, particularly nebulizers, which are commonly used to generate aerosols from aqueous medications. Both jet nebulizers and vibrating mesh nebulizers involve an atomization process that exerts strong shearing forces on the nanoparticles, leading to a significant loss in their mRNA delivery efficiency. Thus, addressing and mitigating these challenges may help to maximize the efficacy and safety of inhaled mRNA therapies for pulmonary diseases. Studies focused on optimizing nanoparticles have shown promising results in improving their ability to endure the shearing forces exerted by nebulizers. Increasing the molarity of polyethylene glycol (PEG) in lipid nanoparticle (LNP) formulations may enhance mRNA transfection after nebulization. High PEG contents in LNPs could improve their resilience to damage during the acrosolization process, attenuating the negative impact of shear forces on mRNA delivery efficiency.

While fine-tuning nanoparticles may rescue their delivery competence during nebulization, an alternative solution to this challenge lies in the development of a novel aerosolization platform. Nebulization through a vibrating mesh essentially involves directing fluid flow through a fine screen to atomize aerosols on a microscale. In this context, exploring other possible fluid mechanics for plume generation presents a promising chance to develop innovative aerosolization devices. Microfluidic devices have been widely employed in the production of various nanoparticles, providing continuous, controllable, and reproducible manufacturing of small-sized nanoparticles with a narrow size distribution in a simple process. Without being tied to a particular theory, it is possible the system can utilize microfluidics to flow LNPs through micro-channels offers the potential for aerosolizing mRNA without subjecting the nanoparticles to damaging shearing forces.

A microfluidic-based aerosolization ("MAP") platform can generate uniform aerosols containing mRNA encapsulated within LNPs (LNP/mRNA), effectively circumventing damaging shear forces. A microfluidic chip is connected to a cartridge that contains LNP/mRNA solution, providing on-demand droplet generation with precise dose control capabilities potentially for either individual chronic treatment or mass vaccination purposes. Unlike the ultrasonication method in vibrating mesh nebulizers or the jet explosion method in jet nebulizers, droplet generation process in this microfluidic aerosolization platform expels droplets with minimal shear-affected volume, making it highly suitable for delivering macromolecule-based therapies, such as nucleic acids, proteins, and nanoparticles. An example microfluidic aerosolization platform was compared to the clinical-grade vibrating mesh nebulizer based on ultrasonication method for droplet generation. For the studies, a gold standard ionizable lipid with formulations previously optimized for siRNA and mRNA delivery was used to highlight clinical translation of the microfluidic platform provided for by the present disclosure. This innovative platform holds promise to address the clinical need of inhaled nanoparticles for a broad range of RNA therapeutics and vaccines by offering a controlled and efficient aerosolization without compromising the integrity of the nanoparticles.

Overview

Inhalable gene therapy holds tremendous potential for diverse drug development pursuits, including inhalable vaccines and therapies for inherited lung disorders like cystic fibrosis (CF). Even with recent discovery of selective organ-targeting LNPs leading to effective mRNA transfection of the lungs, inhalation continues to stand out as an non-invasive and effective approach to specifically reach the lung bronchioles and parenchyma while avoiding unintended systemic transfections. Given the expanding application of mRNA in gene editing, the interest in achieving highly accurate delivery through inhalation has grown substantially, particularly for its potential to offer a lasting solution to inherited lung disorders. However, ensuring a sufficient therapeutic dose remains a significant hurdle. One plausible explanation for the limited pulmonary delivery could be the susceptibility of nanoparticles to destabilization during aerosolization. Researchers have actively sought a solution to this deadlock, working on developing more robust nanoparticles through meticulous formulation adjustment and exploration of diverse biomaterials. While these efforts are promising, the resolution of this challenge might ultimately stem from the innovation of advanced medical devices capable of generating aerosols while preserving the integrity of nanoparticles.

A microfluidic aerosolization platform ("MAP") can produce nanoparticle aerosols suitable for inhaled mRNA therapy. Findings affirm the capability of this MAP to generate a uniform nanoparticle aerosol without causing deformation in nanostructure or loss of encapsulated mRNA. Unlike conventional nebulizers such as vibrating mesh nebulizers and jet nebulizers, the MAP employs individually addressable nozzles for precise droplet ejection, allowing the generation of an aerosol containing LNP/mRNA at a lower operating frequency. Through this low shear aerosolization approach, the MAP prevents nanoparticle disruption, lipid aggregation, and mRNA leakage that occur with other nebulizers. Namely, this MAP maintains the size distribution and mRNA encapsulation of LNPs even after the aerosolization process. This was validated by cryoTEM imaging, which revealed minimal impact on LNP morphology compared to the distortion and dissociation observed with the mesh nebulizer. This preservation of nanoparticle integrity is critical not only for effective mRNA delivery to cells but also to prevent unwanted side effects in the respiratory system. Furthermore, the MAP offers precise control over droplet size and plume dimensions, ensuring accurate dosing. Importantly, it exhibited more efficient mRNA delivery efficiency to cells compared to the conventional nebulizer. While the mesh nebulizer led to a drastic 100-fold reduction in mRNA delivery, the MAP consistently maintained intracellular mRNA delivery efficiency. These results emphasize how the intactness of nanoparticles directly influence mRNA delivery efficiency. Lastly, despite the LNPs' inherent tropism to the liver, the LNP aerosols generated by the MAP successfully delivered mRNA to the mouse lungs through inhalation. It was achieved in a dose-dependent manner, exhibiting selective lung transfection without causing significant inflammations. These findings highlight the potential utility of the platform for administering pulmonary mRNA therapies.

The system may have several advantages. Firstly, to mitigate potential thermal denaturation, it may be desirable to minimize the temperature rise during bubble formation to prevent any adverse effects on LNP structure and mRNA stability. The aerosolized LNP/mRNA produced by the MAP demonstrated minimal changes in their physicochemical properties. Moreover, the application of heat to LNP/mRNA for aerosolization is brief, thus limiting its thermal impact on efficacy. Secondly, to address diverse clinical needs in pulmonology, enhancements to nozzle geometry are necessary to accommodate a wide range of droplet diameters. A recent study demonstrated that intratracheal vaccination induced peripheral and mucosal immunity against the SARS-COV-2 antigen, suggesting that the MAP could obviate the need for endoscopy in administration. Furthermore, to improve precision in delivering therapies to deep lung tissues, the MAP nozzle geometry needs to be engineered for smaller droplet diameters. This could enable more effective treatment of lower respiratory tracts, such as bronchioles and alveoli. I Recent advancements in LNP chemistry have identified the roles of PEG molarity in RNA delivery. The incorporation of PEG into LNPs can serve to maintain the nanoparticles' stability during self-assembly. In addition, PEG molecules hinder interactions between LNPs and serum proteins, extending the nanoparticles' circulation time. However, they also inhibit the formation of a biomolecular corona on the nanoparticle surface, which delays the LNPs' endocytosis and subsequent mRNA delivery. In the context of LNP nebulization, PEG molecules are considered to contribute to the recovery or stabilization of nebulized nanoparticles through steric effects. This intricate interplay of PEG in LNP chemistry adds complexity to the formulation design for inhalation. Even with meticulous optimization, the nebulization process compromises LNP integrity, thus obscuring the key traits necessary for effective lung transfection. The MAP may help eliminate uncertainties in formulation discovery by preventing LNP deformation during nebulization. This platform holds the promise of enabling optimized LNP formulations, developed for systemic administration, to also perform effectively in inhalation scenarios. Alternatively, formulation screening based on intratracheal instillation could offer higher accuracy in predicting efficacies when delivered via aerosols. Of note, the preservation of mRNA cargo integrity throughout the aerosolization process could facilitate precise dosing and reduce the risk of immunogenicity associated with activating RNA sensors in the patients' lungs. Collectively, the MAP could play a pivotal role in expediting the development of inhalable nanoparticles. Further, harnessing this platform has the potential to mark a significant leap in overcoming the challenges associated with translation of pulmonary gene therapy.

Additionally, the MAP may help to enable optimized LNP formulations, developed for systemic administration, to also perform effectively in inhalation scenarios. Formulation screening based on intratracheal instillation could offer higher accuracy in predicting efficacies when delivered via aerosols in part due to the consistent creation of aerosols prepared by the MAP. The preservation of mRNA cargo integrity throughout the aerosolization process could facilitate precise dosing and reduce the risk of immunogenicity associated with activating RNA sensors in the patients' lungs.

Example Aerosolization System

Figure 1B:
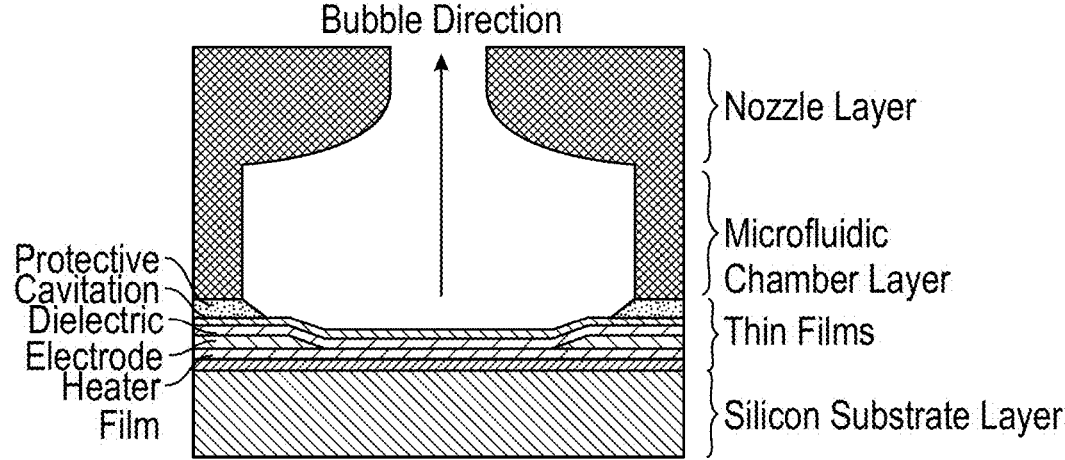
FIG. 1B is a cross-sectional view of a microfluidic chamber of the chip.
Figure 1C:
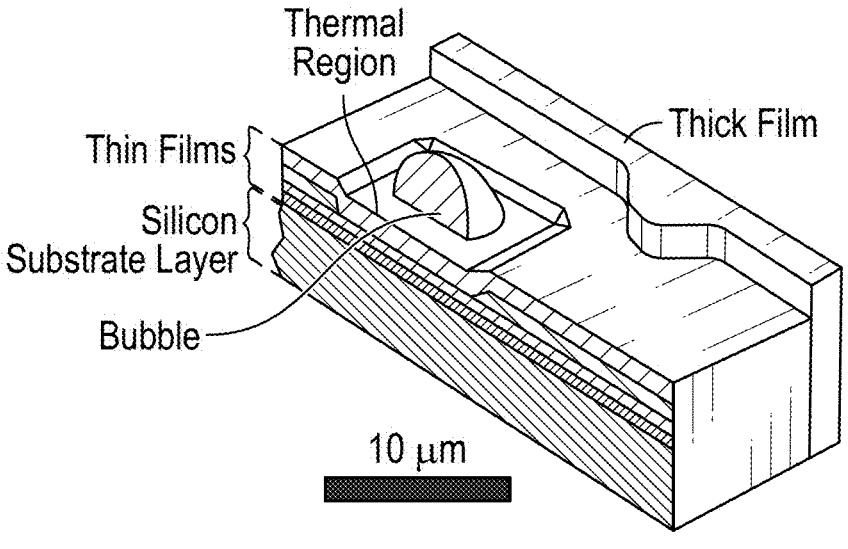
FIG. 1C illustrates the layer structure of the microfluidic chamber with a bubble forming.
Figure 1D:
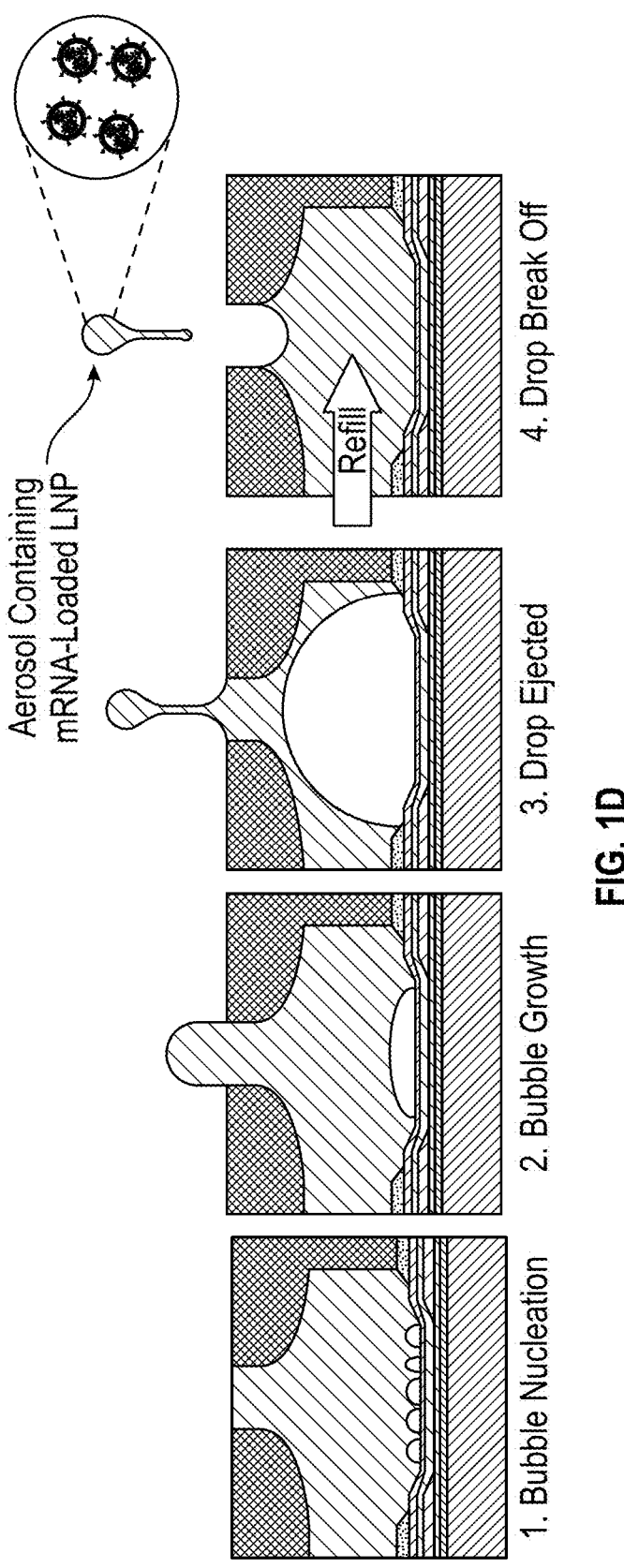
FIG. 1D is a scheme illustrating bubble formation on the chip with steps of (1) bubble nucleation, (2) bubble growth, (3) drop ejection, and (4) drop break off and refill.

To achieve effective delivery of LNP-assisted gene therapies in the form of micron-sized droplets, a microfluidic device consisting of a complementary metal oxide semiconductor (CMOS) based chip with integrated microfluidic structures was used. This device comprises an array of 960 droplet ejectors, each individually addressable, enabling the generation of droplet plumes containing LNP/mRNA (FIG. 1A). Briefly, the microfluidic chip is monolithically fabricated on a silicon base layer through standard photolithographic techniques, incorporating a polymeric manifold and nozzle configuration. It is a specialized device that utilizes microfluidic and thermodynamic principles to flow the liquid through the fluid manifolds and to generate and eject small droplets of liquid. Each of the 960 droplet ejectors consists of a microfluidic chamber that holds the liquid, and a nozzle or orifice (approximately 10 µm in diameter) through which the liquid droplets are expelled (FIG. 1B, C). Underneath the chamber, multiple thin film layers of heater elements and electric materials are integrated. The device is actuated digitally by applying short electrical pulses to individual heater elements, generating microbubbles that propel the droplets out of the nozzle. In detail, when an electric current is passed through the resistive heating element, the temperature of the surface of the heater increases rapidly, causing the liquid in substantial contact with the heater surface to vaporize. As the liquid vaporizes, it forms a bubble within the microfluidic channel, and the sudden expansion of this bubble propels a droplet out through the nozzle (FIG. 1D). Proper control of the electrical pulse duration and magnitude consistently generates droplets of a specified size and speed, while actuation of individual ejectors allows for precise and controlled dispensing. For example, if each of the 960 ejectors are actuated individually and repeatedly at a frequency of 10 kHz per nozzle, droplets are produced at a rate of 9.6 million droplets per second, resulting in the production of a plume. (See FIG. 15) Total dispensed volume is adjustable and easily controlled by specifying the exact number of droplets to be ejected per nozzle (e.g., by using a processor to adjusting pulse width or pulse frequency applied to the nozzle. During the entire procedure, the liquid is precisely controlled and conveyed to the nozzle through microfluidic techniques, ensuring a consistent and uniform droplet size and shape. Furthermore, the microfluidic techniques enabled accurate control over the plume dimensions, droplet velocity and size, as well as the administered dose.

Figures 2D, 2E:
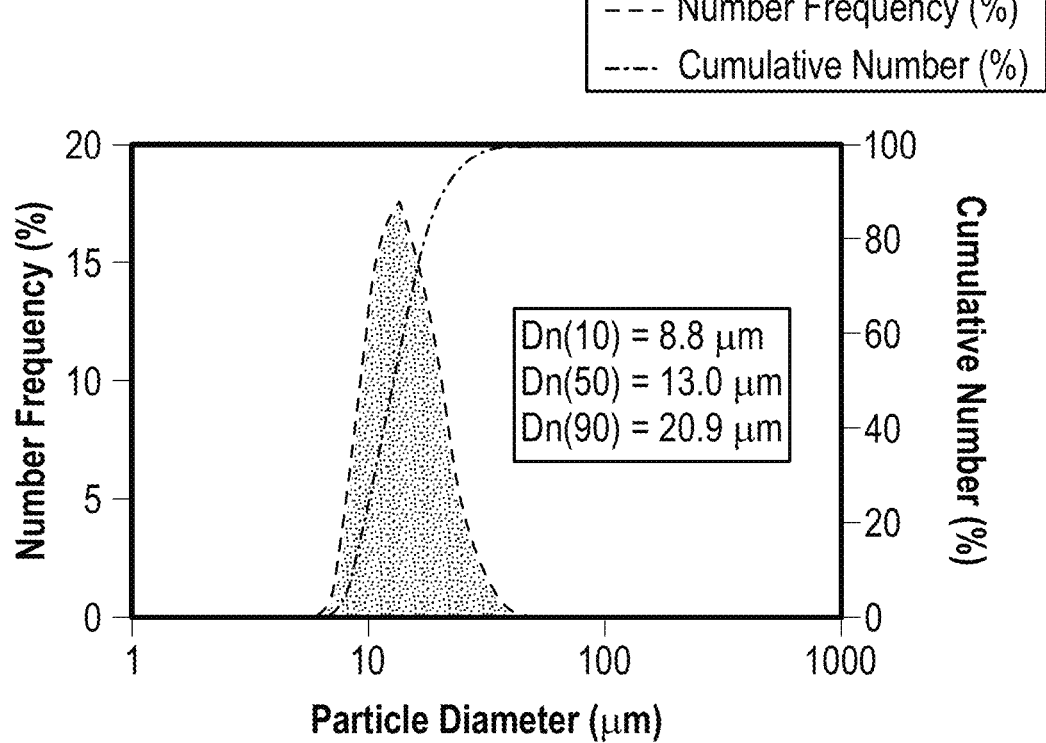
FIGS. 2D-2F chart the droplet diameters, volumes, and % volume at droplets at three different generation frequencies.
Figure 2F:
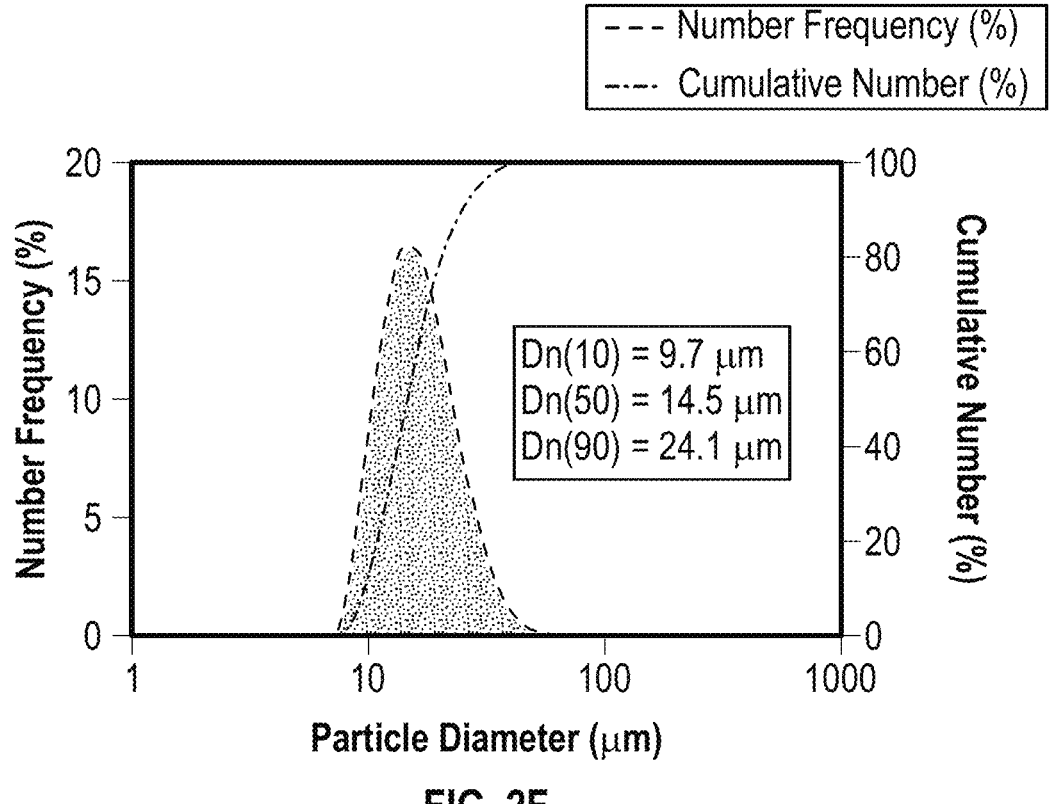
Figure 16:
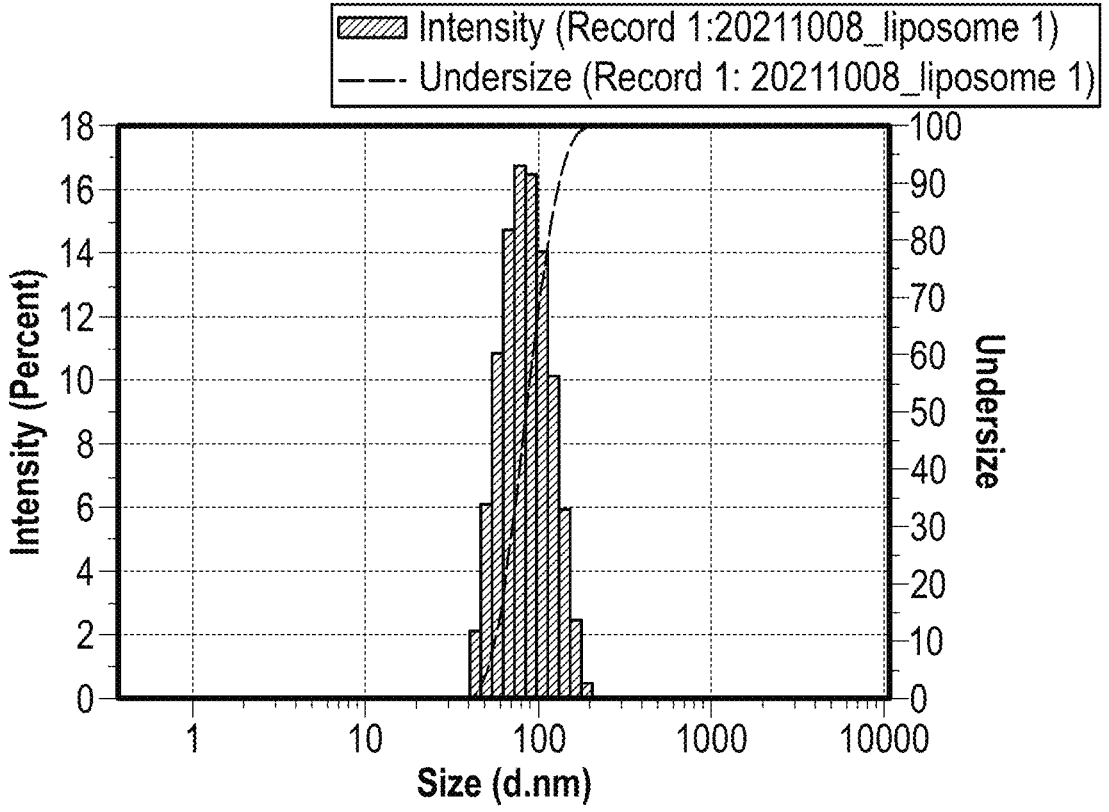
FIG. 16 plots a representative size distribution of liposomes.
Figure 17A:
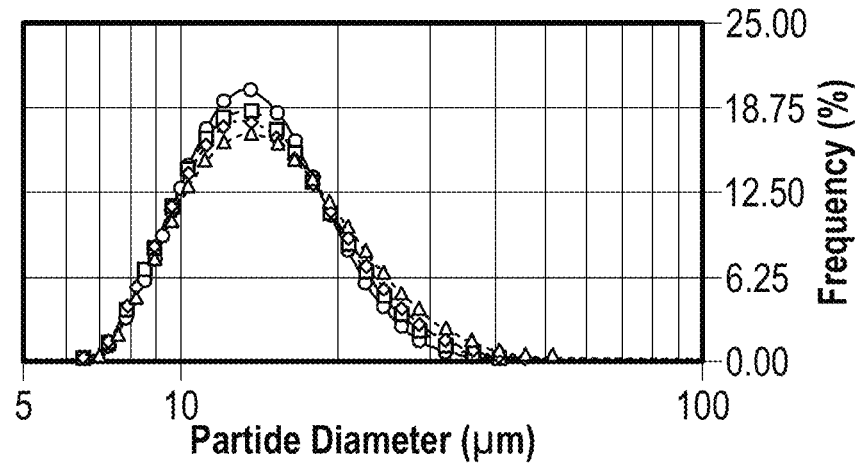
FIG. 17A-17C are plots showing the size distribution of aerosol droplets at various distances from the device.
Figure 17B:
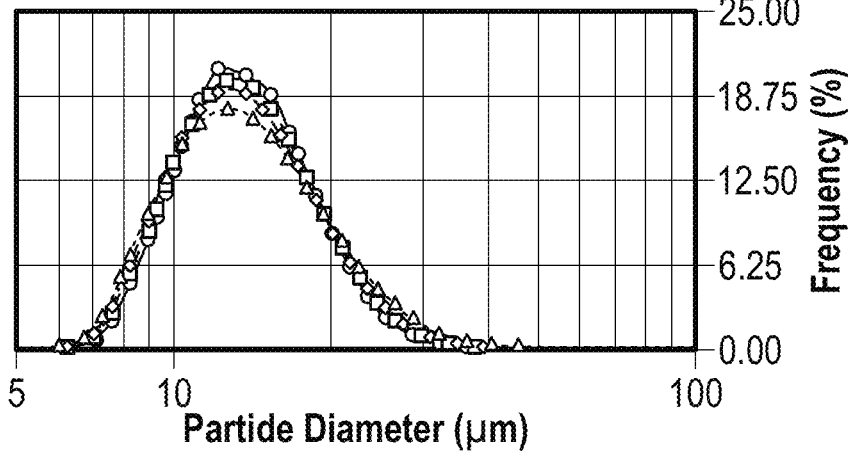
Figure 17C:
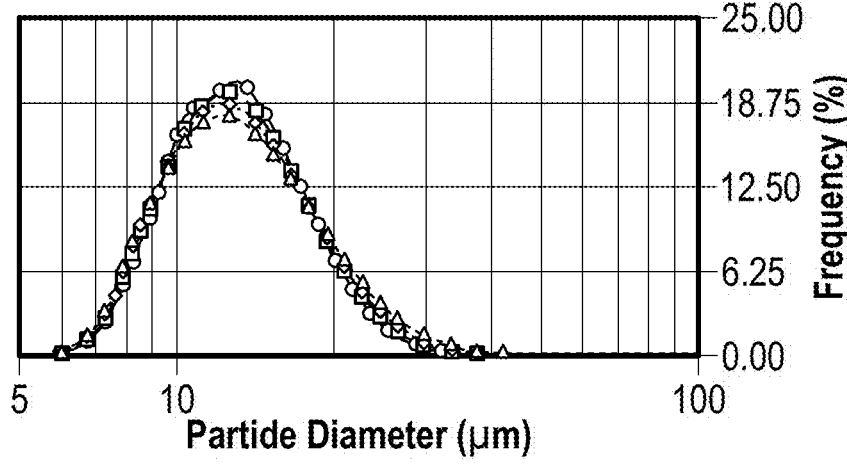
Figure 18A:
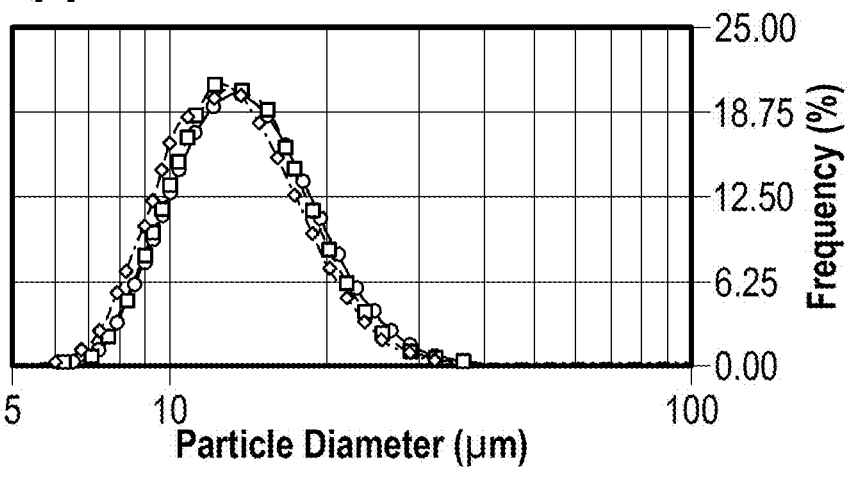
FIG. 18A-18D are plots of the size distribution of aerosol droplets by varying aerosolization frequencies or the number of nozzles.
Figure 18B:
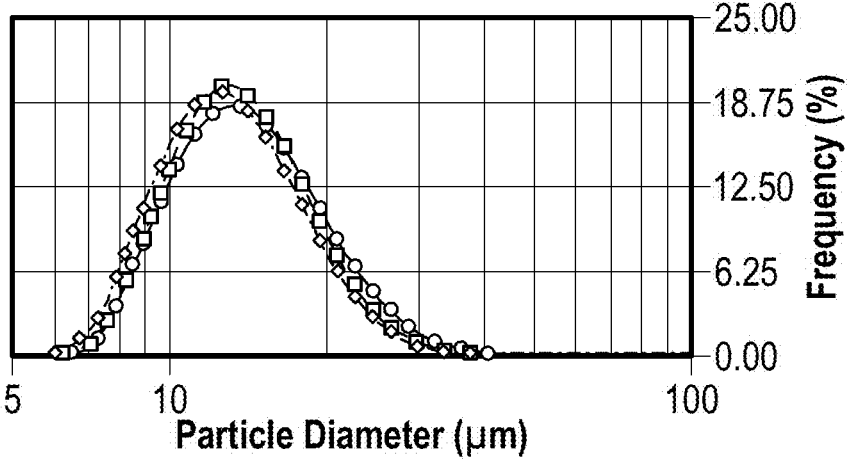
Figure 18C:
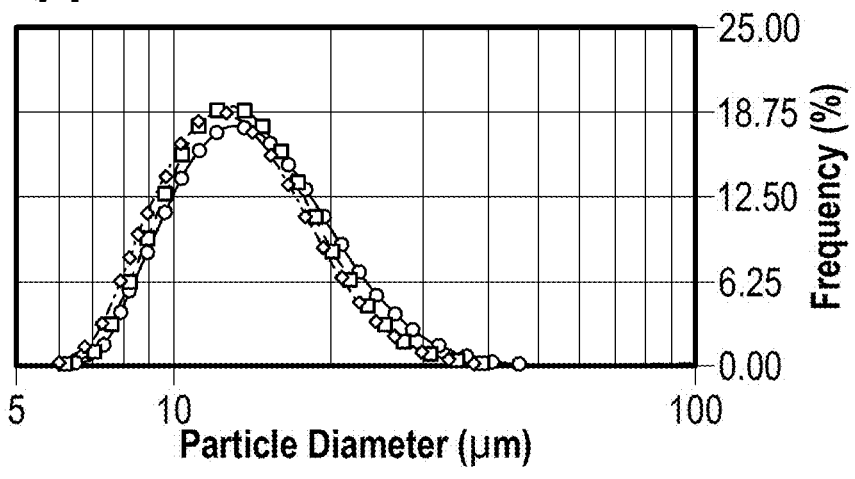
Figure 18D:
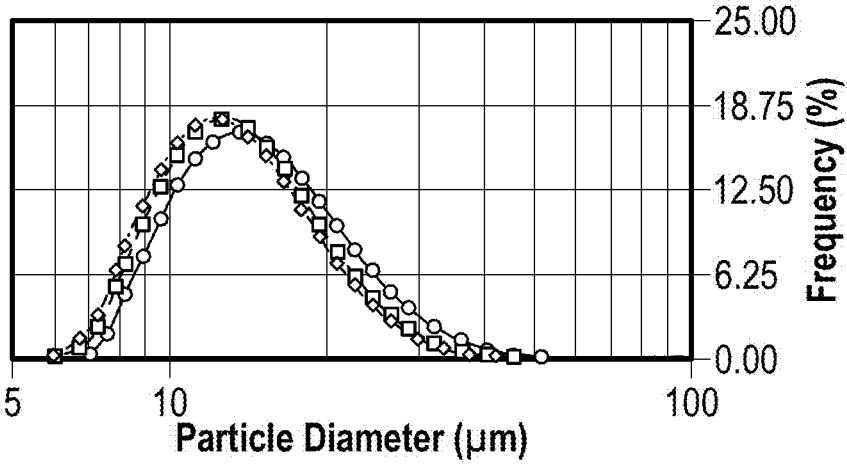
Figure 19A:
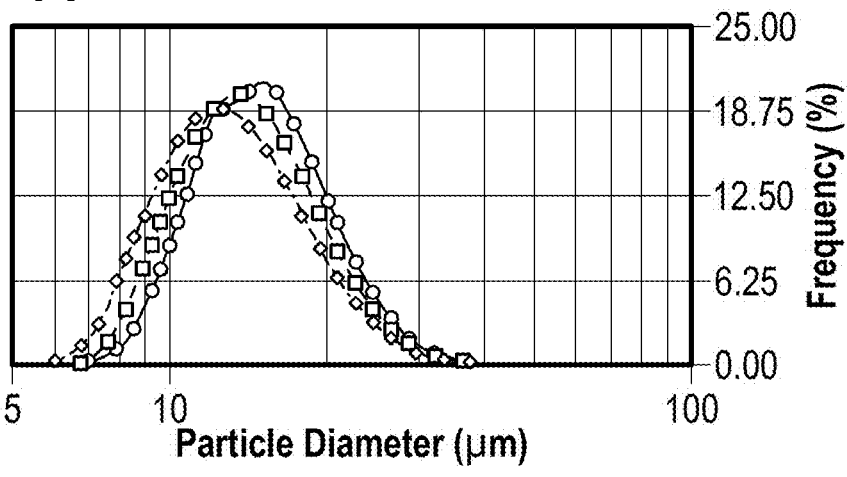
FIG. 19A-19F are plots of the size distribution of aerosol droplets at various elapsed times of aerosolization.
Figure 19B:
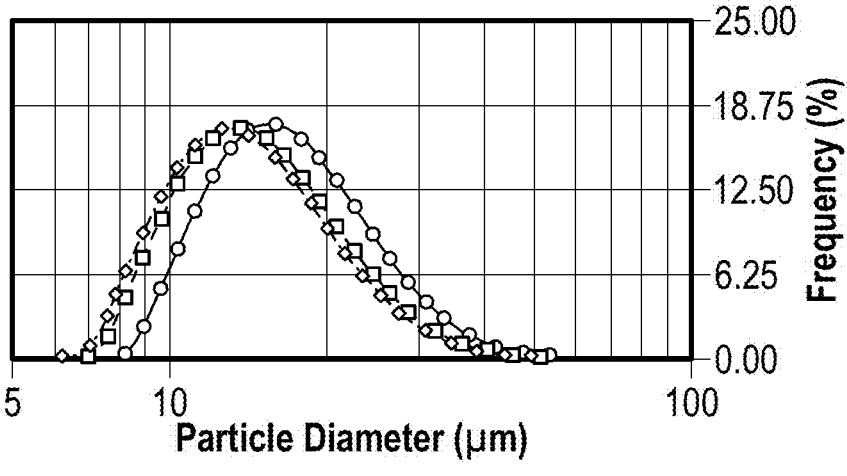
Figure 19C:
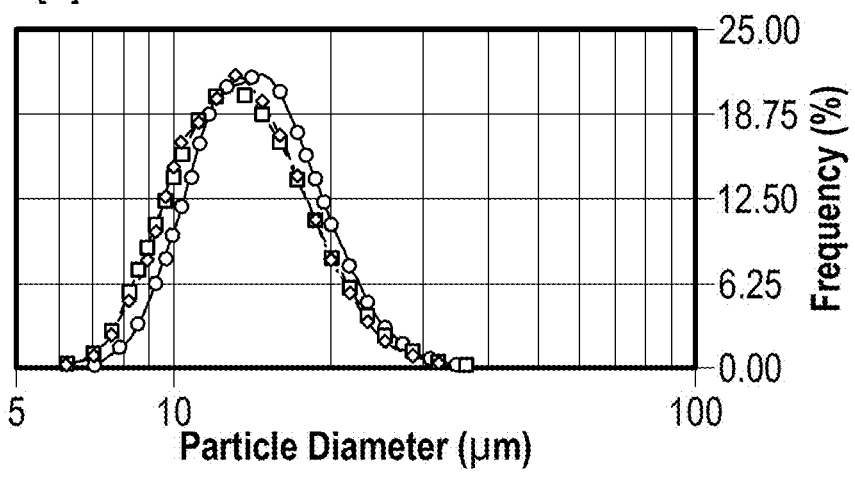
Figure 19D:
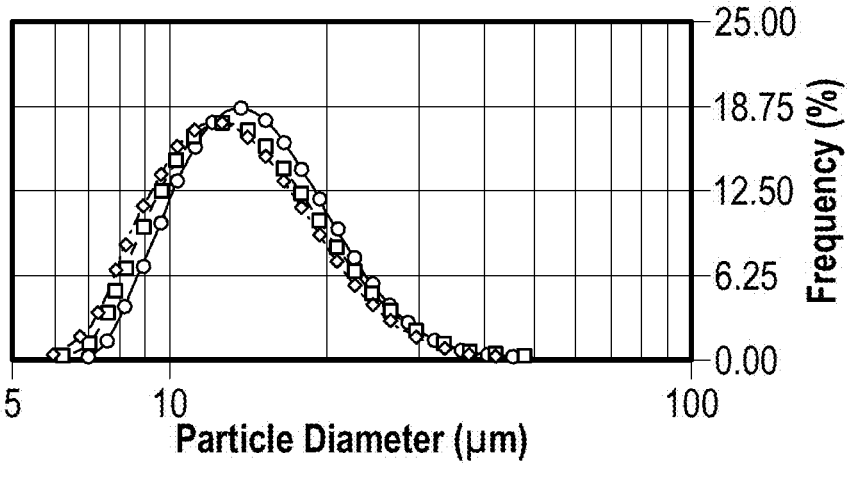
Figure 19E:
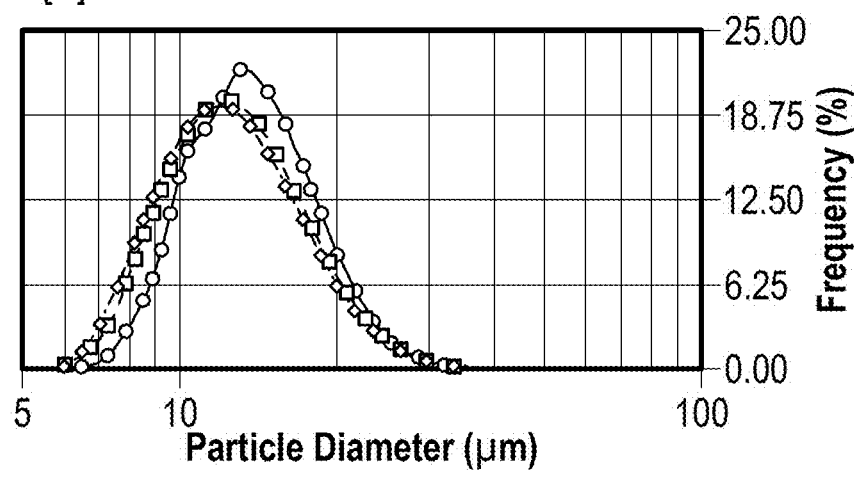
Figure 19F:
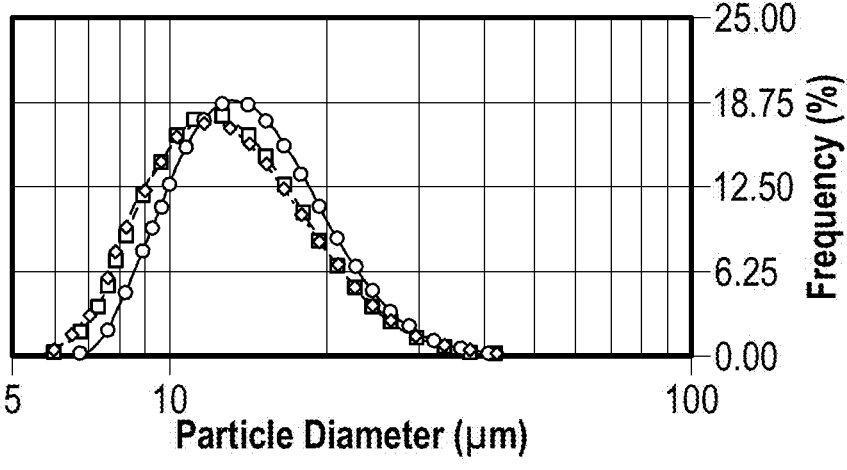

In inhalation-mediated drug delivery, the droplet size plays a pivotal role in determining its site of accumulation within the pulmonary tissues. Larger droplets tend to deposit in the upper airways and are susceptible to removal through mucociliary clearance before reaching the deeper lung tissues. Conversely, smaller droplets have a higher chance of penetrating deeper into the lungs and reaching the alveolar region. Therefore, the ideal droplet size for inhalation-mediated drug delivery depends on the specific target site of action. For conditions like asthma, chronic obstructive pulmonary disease (COPD), or CF, smaller droplets capable of reaching the lower airways and alveoli are preferred. On the other hand, larger droplets may be more suitable for topical treatment of upper respiratory infections or inhaled vaccinations. Hence, precise control over droplet size in aerosols is vital for the successful development of effective delivery platforms for inhalation-mediated medication. To assess the droplet size generated by the MAP, analyses of their size distribution was conducted using two different techniques: a JetXpert drop watcher and a Spraytec® droplet size measurement system. For the droplet size characterization, liposomes (DSPC:cholesterol:DSPE-PEG2K=52:45:3) were used to mimic physical properties of bulk LNP suspensions. The mean size of the liposomes was approximately 80 nm with an approximate polydispersity index (PDI) 0.1 (FIG. 16). The drop watcher system allows us to capture precise images of individual droplets in flight, measure their shape, and estimate their volume, even at the pico-liter scale. Drop formation of droplets ejected from the nozzles of the microfluidic cartridge at two different operating frequencies was performed and compared, resulting in each nozzle being actuated at 1 KHz and 15 kHz, respectively, for visualization of a single drop ejection event (FIGS. 2A-2B). Drops generated at 1 KHz were observed to break apart into 4 droplets in flight (FIG. 2A), while those at 15 kHz broke up into 3 droplets (FIG. 2B). By analyzing the captured images of the ejected fluid upon exiting the nozzle opening, it was revealed that 4 droplets formed at 1 KHz ejection frequency contained 59%, 30%, 8%, and 3% of the total ejected volume, respectively (FIG. 2C). Similarly, when operating at 15 kHz frequency, the three droplets formed per ejection were 72%, 17%, and 11% of the total ejected volume (FIG. 2D). It is noteworthy that, because the droplets have different velocities, they collide with each other, resulting in the breakup or merge in the air. As a result, the drop watcher system is limited to the analysis of the breakup of droplets upon ejection from the nozzle opening. To accurately determine the droplet size of the aerosols, Spraytec®, a size determination method based on laser diffraction of aerosols was used. Droplet sizes were measured at two ejection frequencies—at 7.5 kHz and 15 kHz-using all of the nozzles (FIGS. 2E, F). At 7.5 kHz, 50% of the total number of drops were less than 13.0 µm (Dn(50)) and 90% of the drops were less than 20.9 µm (Dn(90)) (FIG. 2E). Similarly, at 15 kHz, 50% of the total number of drops were less than 14.6 µm ((Dn(50)) and 90% of the drops were less than 24.4 µm (Dn(90)) (FIG. 2F). In some examples, 19.4 µm and 24.4 µm are alternative upper range bounds for droplet size, depending upon the desired clinical application. The droplet size distribution was characterized as measurement parameter varied, including by measuring distances, the number of nozzles, and the elapsed time of aerosolization. When the measurement was taken near the nozzle plate, the distribution became slightly narrower (FIG. 17). It was observed that lowering the frequency of aerosolization or the number of nozzles tended to slightly decrease the droplet size (FIG. 18). Additionally, the size over the course of elapsed time during aerosolization was measured. The size distribution was smaller at the beginning of aerosolization compared to the middle and end, suggesting that the aerosolization process becomes more stable as dispensing continues (FIG. 19). It is noteworthy that the impact of the studied variables on droplet size was consistently less than 2 µm in all cases, indicating the robust aerosolization performance of the microfluidic platform (FIG. 17-19).

Figure 2G:
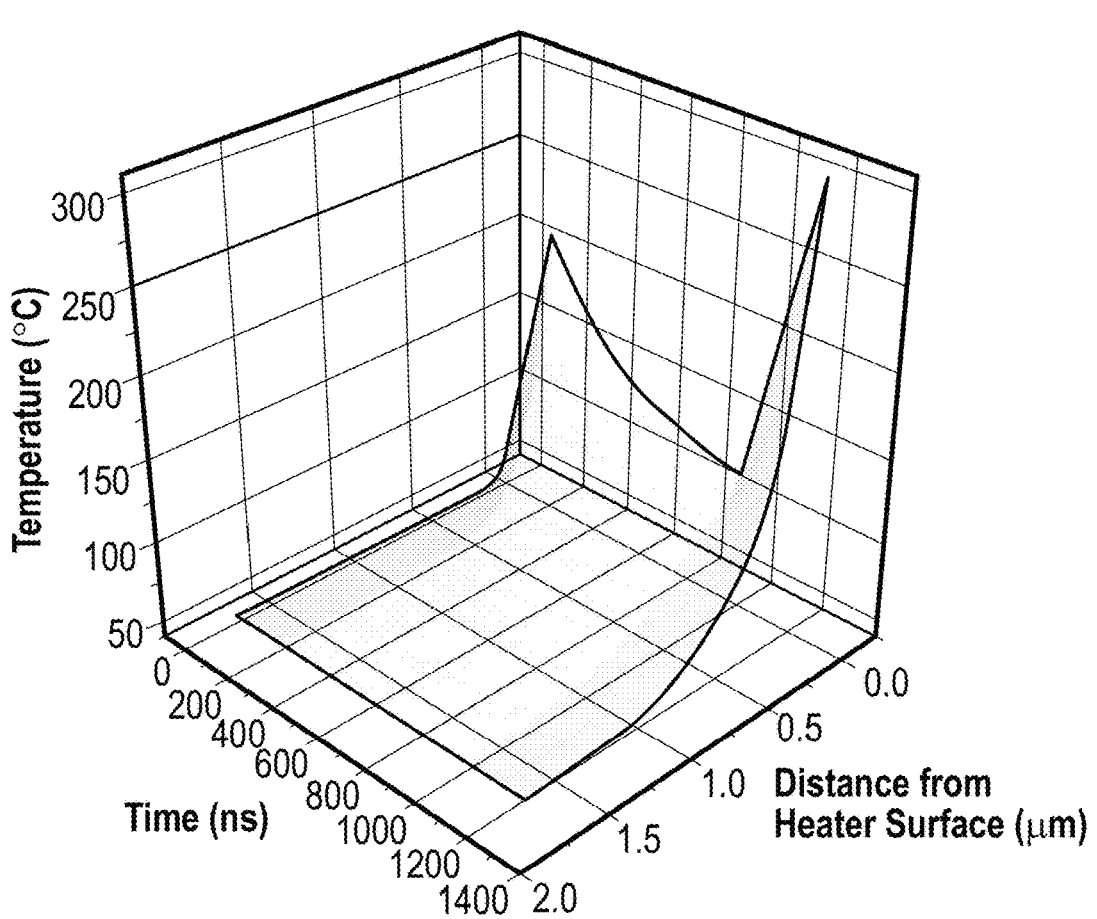
FIGS. 2G and 2H show simulation-based analysis performed to estimate the temperature change of the fluid in the thermal boundary layer during the electric pulse, considering the effects of time and geometric dimensions.
Figure 2H:
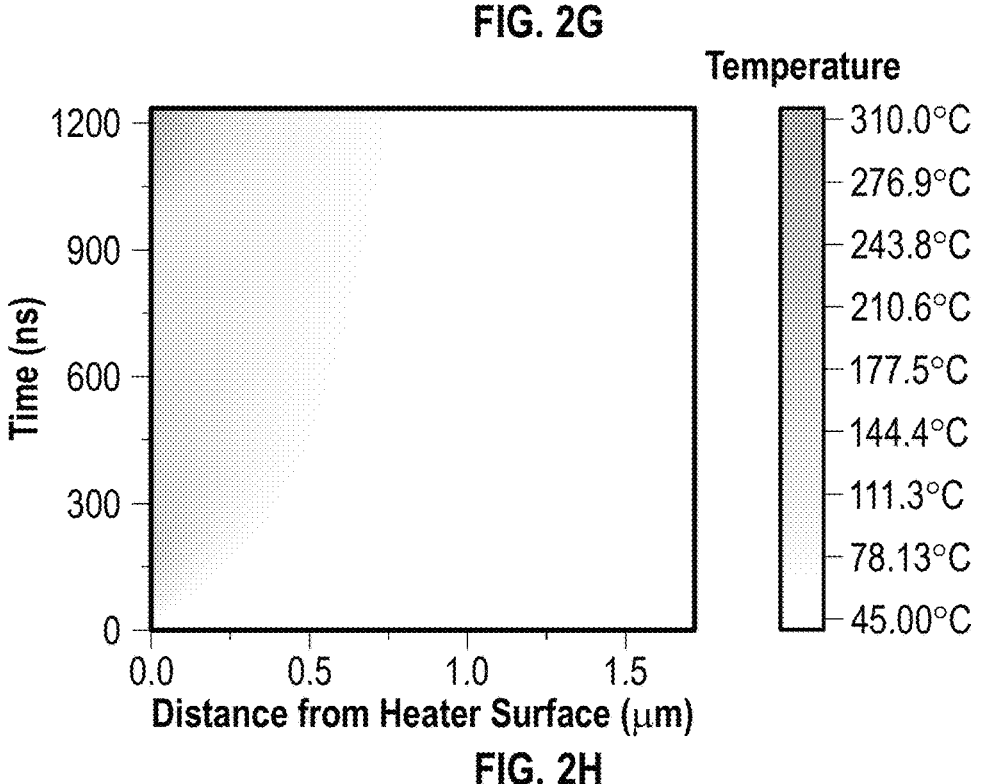

Analysis was also performed, via simulation to estimate the temperature change of the fluid in the thermal boundary layer during the electric pulse, considering the effects of time and geometric dimensions. The temperature distribution of the fluid in the ejector chamber was non-uniform, with higher temperatures closer to the heater surface (FIGS. 2G, 2H). As the distance from the heater surface exceeded 1 µm, the temperature increase was minimal. Additionally, the temperature rise was highly correlated in time with the actuation of the drop ejection with the electrical signals to the heater, with the peak temperature near the end of the ejection sequence (FIGS. 2G, 2H). Although the temperature experienced a localized increase to 300° C. for only a few microseconds, this rise was limited to the regions in proximity to the heater, which is unlikely to compromise the overall stability of the LNP/mRNA to be aerosolized.

Figure 3A:
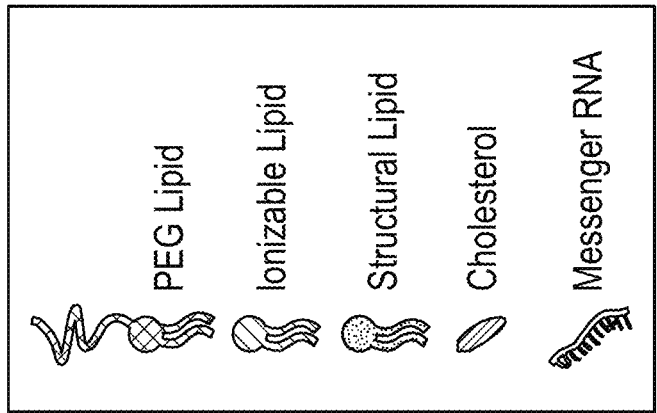
FIG. 3A is a cartoon drawing showing a lipid nanoparticle and its components.
Figure 3A:
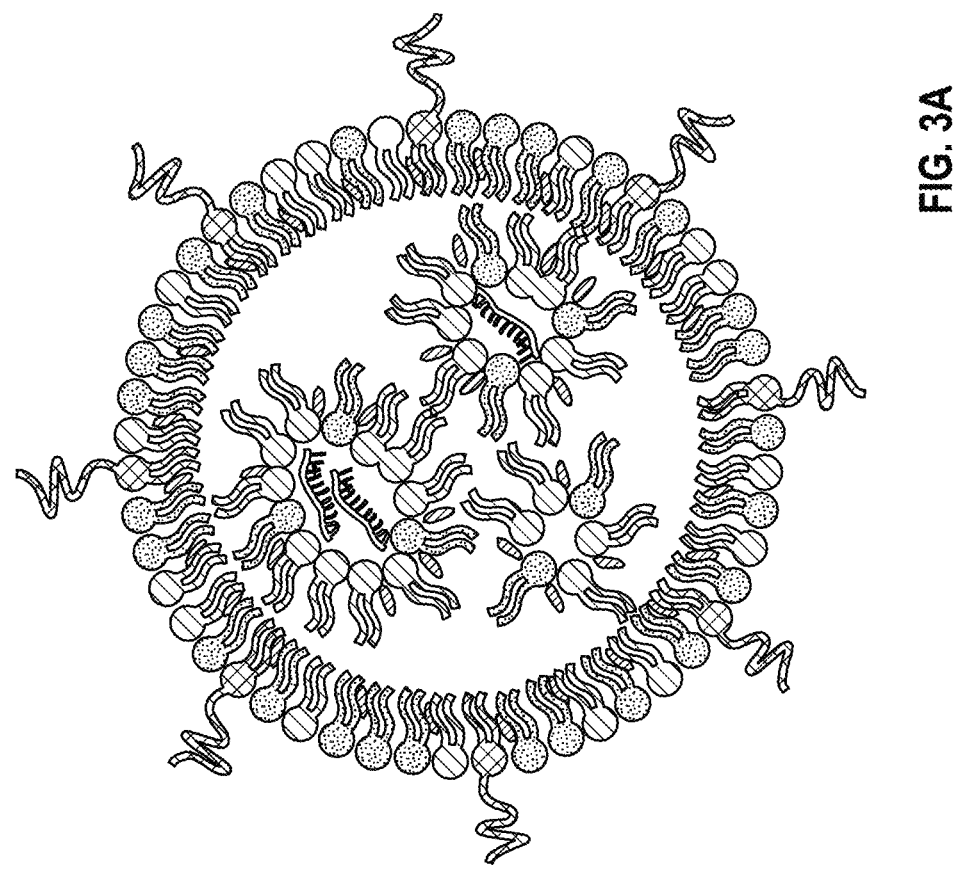
Figure 3B:
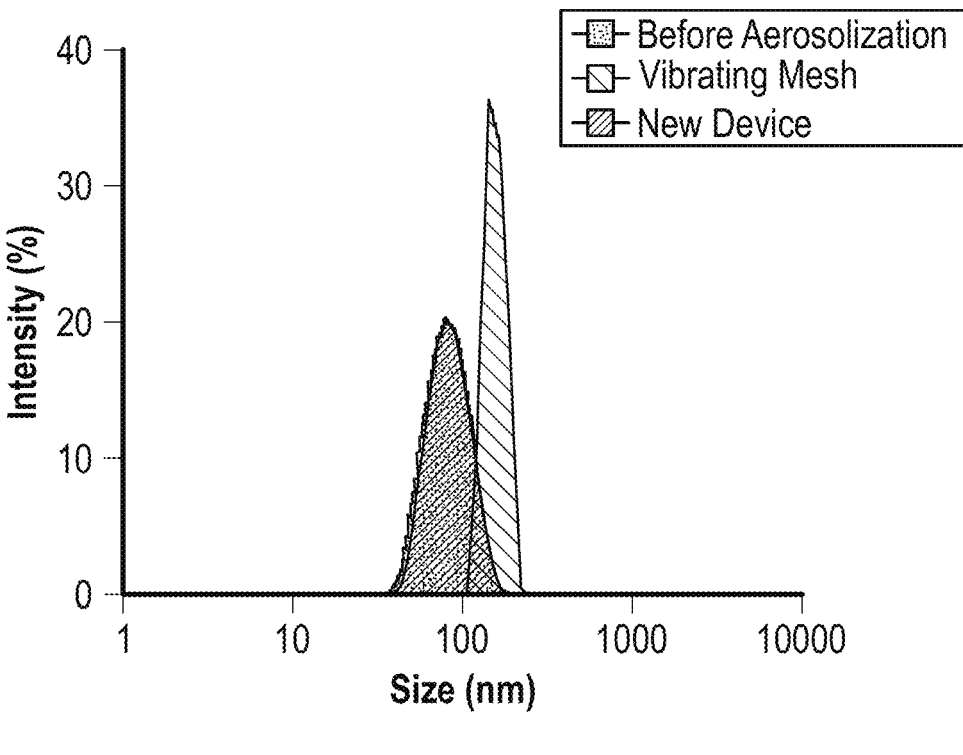
FIGS. 3B-3F compare hydrodynamic size distributions, zeta-potentials, and RNA encapsulation of the nanoparticles generated using either a vibrating mesh nebulizer or the microfluidic aerosolization platform.
Figure 3C:
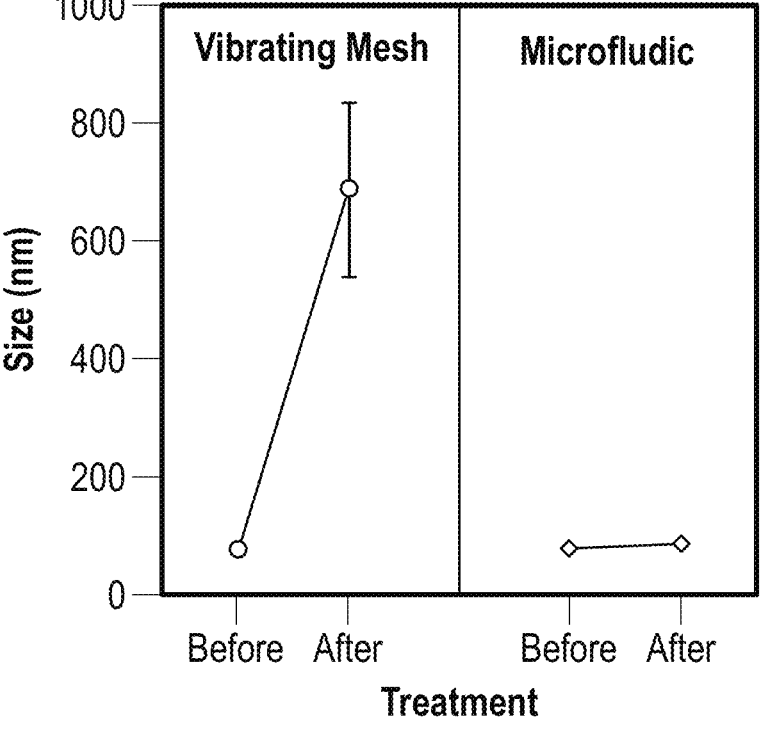
Figure 3D:
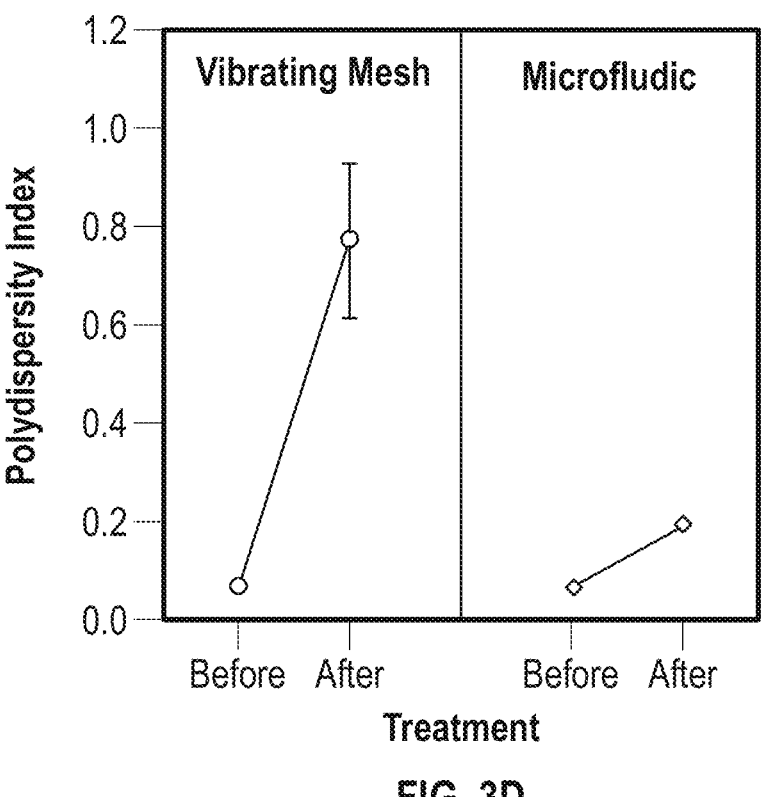
Figure 3E:
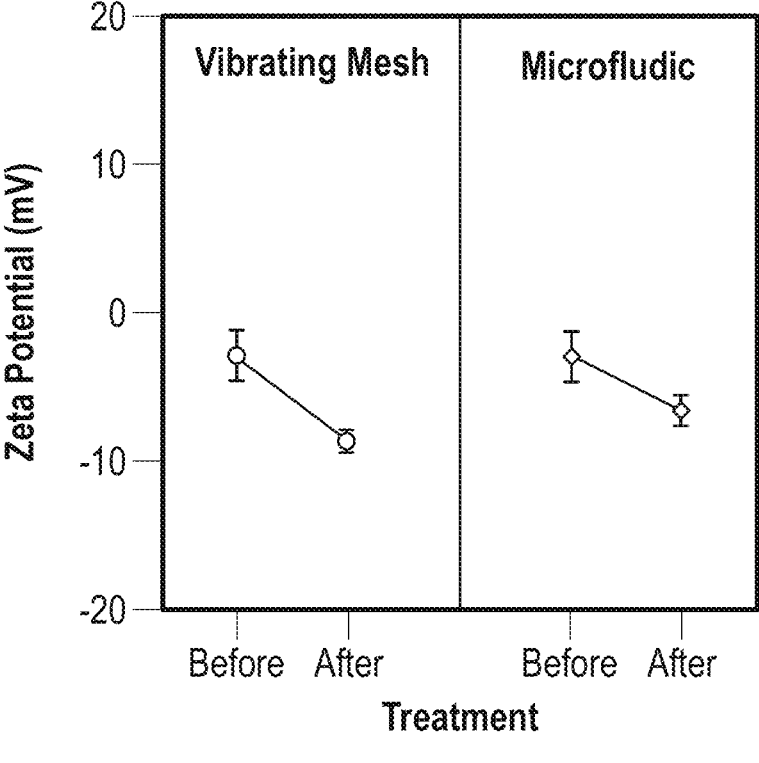
Figures 3F, 3G:
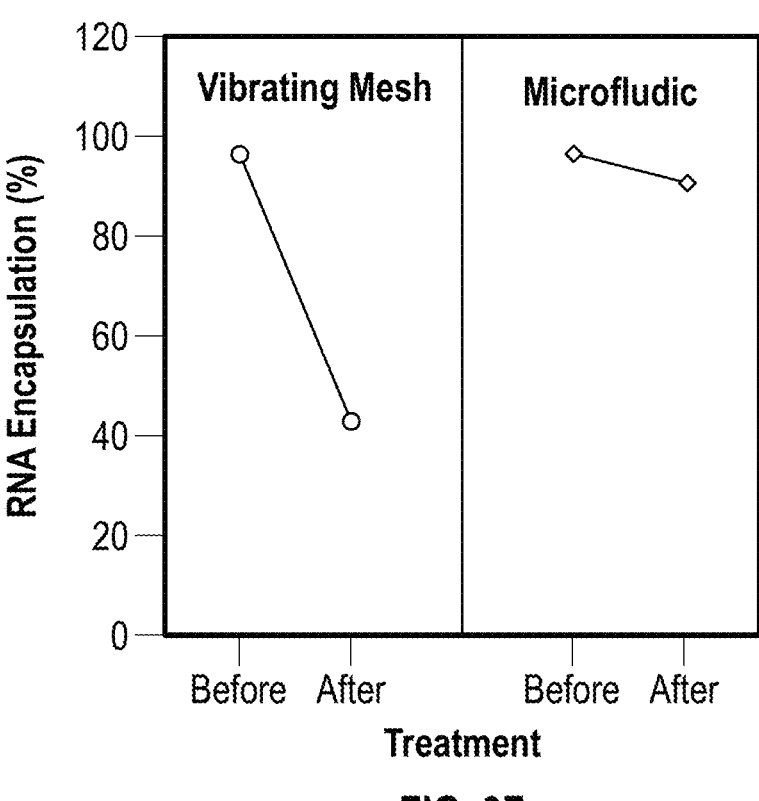
FIG. 3G is a western blot comparing RNA encapsulation of the nanoparticles created by the microfluidics aerosolization system or the vibrating mesh nebulizer, as well as untreated nanoparticles and free mRNA.
Figure 3H:
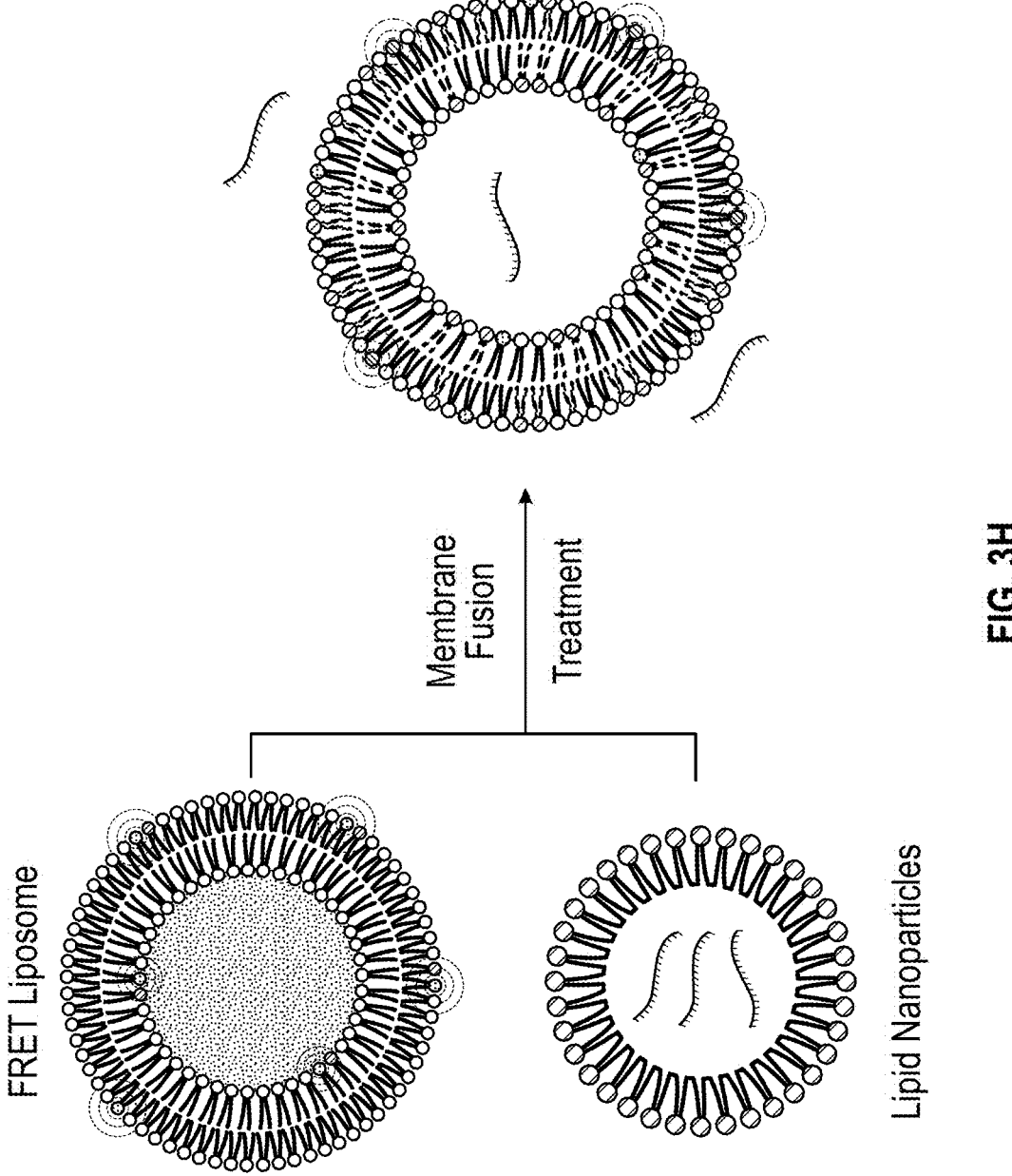
FIG. 3H is a cartoon drawing of liposomes containing two DOPE-conjugated FRET probes, 7-nitrobenzo-2-oxa-1,3-diazole (NBD-PE) and lissamine rhodamine B (Rho-PE), prepared to result in "FRET liposomes."
Figure 3I:
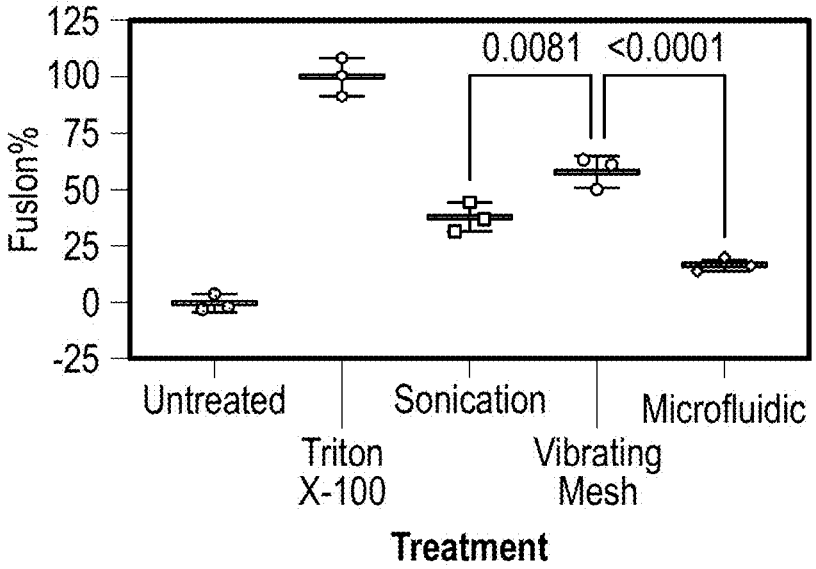
FIG. 3I plots fusion percentage of liposomes to assess the frequency of membrane fusion events for the NPLs in droplets created by the microfluidic aerosolization system as compared to sonication, vibrating mesh, Triton X-100 and untreated liposomes.

To examine any potential impact of thermal changes and shearing forces generated by the microfluidic platform, LNPs were aerosolized and encapsulated mRNA were delivered to the cells. The LNP formulation consisted of DLin-MC3-DMA, cholesterol, DSPC, and DMG-PEG2000 at a molar ratio of 50:38.5:10:1.5 (i.e., the lipid composition of patisiran), with the mRNA present at an N/P ratio of 5.30 (FIG. 3A). Following the aerosolization of LNP/mRNA using either a vibrating mesh nebulizer or a microfluidic platform in accordance with the present disclosure, the hydrodynamic size distributions, zeta-potentials, and RNA encapsulation of the nanoparticles with those of the untreated nanoparticles were compared (FIGS. 3B-3G). Untreated LNP/mRNA were <100 nm in hydrodynamic diameter with narrow distributions (PDI<0.2) (FIG. 3B-3D). When aerosolized by a vibrating mesh nebulizer, the size distribution of the nanoparticles was changed dramatically. As shown previously, the ultrasonication of a mesh nebulizer resulted in large, unstable, and aggregated LNPs. The nebu- lized LNP/mRNA displayed approximately 700 nm hydro- dynamic diameter with wide distributions (PDI>0.7) (FIGS. 2B-2D). In contrast, the size distributions of the nanopar- ticles were scarcely affected by the microfluidic aerosoliza- tion (FIG. 3B-3D). The hydrodynamic sizes of the nanopar- ticles that went through microfluidic aerosolization were <100 nm with narrow distribution (PDI<0.2) (FIGS. 3C-3D). Despite slight decreases after aerosolization, zeta- potentials of all LNP samples were in the neutral range (i.e., between +10 and −10 mV) (FIG. 3E). These conspicuous differences in the dynamic light scattering (DLS) analysis indicate that the microfluidic platform provides clear ben- efits in retaining the physicochemical properties of LNP/ mRNA during aerosolization than traditional mesh nebuliz- ers. The encapsulation state of mRNA after LNP aerosolization were characterized. While untreated LNP/ mRNA had high encapsulation (>95%), the ultrasonication of the mesh nebulizers led to significant loss of mRNA encapsulation (ca. 43%) (FIG. 3F). Again, the microfluidic acrosolization rescued the encapsulated mRNA from the leakage, indicating its protective effects of mRNA cargos during aerosolization. To confirm the retainment of cargo encapsulation, the LNP/mRNA samples were subject to the agarose gel electrophoresis analysis (FIGS. 3G and 20). mRNA solution ('mRNA only' group) and the LNP/mRNA treated with Triton X-100 detergent showed mRNA migra- tion in the gel, generating two bands: one for its linear form and the other for its secondary structure. Untreated LNP/ mRNA did not migrate but remain in the wells, indicating the stable encapsulation of mRNA within the nanoparticles. When tested the LNP/mRNA exposed to the vibrating mesh nebulization, the mRNA bands appeared, indicating that the nanoparticles leaked the mRNA during nebulization (FIG. 3G). By contrast, the ones aerosolized by the microfluidic platform displayed very faint bands in the gel, supporting the negligible amount of mRNA loss during acrosolization (FIG. 3G). These results showed that the microfluidic plat- form can aerosolize LNPs without the risk of mRNA loss (FIG. 3G), in conjunction with the results of mRNA encap- sulation assay (FIG. 3F). Without being tied to a particular theory, the loss of mRNA during nebulization may arise from aggregation and rearrangement of lipids incorporated in the LNPs. LNP/mRNA was tested to examine whether it could go through the membrane fusion in the nebulization processes through fluorescence resonance energy transfer (FRET). Liposomes containing two DOPE-conjugated FRET probes, 7-nitrobenzo-2-oxa-1,3-diazole (NBD-PE) and lissamine rhodamine B (Rho-PE), were prepared, result- ing in "FRET liposomes" (FIG. 3H). The proximate pres- ence of both probes in the liposomes caused a decrease in NBD fluorescence due to FRET occurring between NBD and rhodamine B. Following the process of membrane fusion, the distance between the two probes increased, leading to a subsequent rise in NBD fluorescent signals. To assess membrane fusion events, LNP/mRNA were mixed with FRET liposomes and subjected to various conditions: Triton X-100, bath sonication, vibrating mesh nebulization, and microfluidic aerosolization (FIG. 3I). The signal obtained from the untreated sample represented 0% fusion, while Triton X-100 treatment represented 100% fusion. Among the tested methods, vibrating mesh nebulization induced the highest degree of membrane fusion (FIG. 3I). Notably, it significantly surpassed bath sonication, likely due to the additional shear stresses generated by the pores of the mesh. On the other hand, microfluidic acrosolization resulted in significantly lower levels of fusion (approxi- mately 16% lower), indicating its mild effects on the lipid membrane structure during LNP acrosolization. In summary, microfluidic platforms in accordance with the present dis- closure offer distinct advantages in the aerosolization of LNP/mRNA by preserving the physicochemical properties and structural integrity of the nanoparticles and providing better protection for the encapsulated mRNA cargos, sur- passing the conventional vibrating mesh nebulizer in these aspects.

Next, the morphology of LNP/mRNA after undergoing acrosolization using cryogenic transmission electron microscopy was examined (CryoTEM). The untreated LNP/ mRNA sample displayed a spherical shape with a single bilayer (FIG. 4A), and the particle diameter was found to be less than 100 nm, consistent with the DLS analysis results (FIG. 2C). However, ultrasonication with mesh nebulizers caused the dissociation and aggregation of the nanoparticles (FIG. 4B). The density of nanoparticle per field of view was also notably reduced (Data not shown). Some particles captured exhibited diameters in the range of several hundred nanometers, and the images had a generally low signal-to- noise ratio, indicating poor electron density of the sample on the grid. In contrast, the morphology of LNP/mRNA fol- lowing microfluidic aerosolization closely resembled that of the untreated sample, despite the presence of a few large nanoparticles (FIG. 4C). The macroscopic observation of the LNP/mRNA samples further supported that the ultrasonica- tion processes led to the dissociation and aggregation of LNPs. Comparatively, the untreated sample and the one subject to microfluidic aerosolization appeared optically translucent. However, the sample aerosolized by the mesh nebulizer became opaque (FIG. 21), suggesting the presence of large particles capable of scattering light.

Figure 4D:
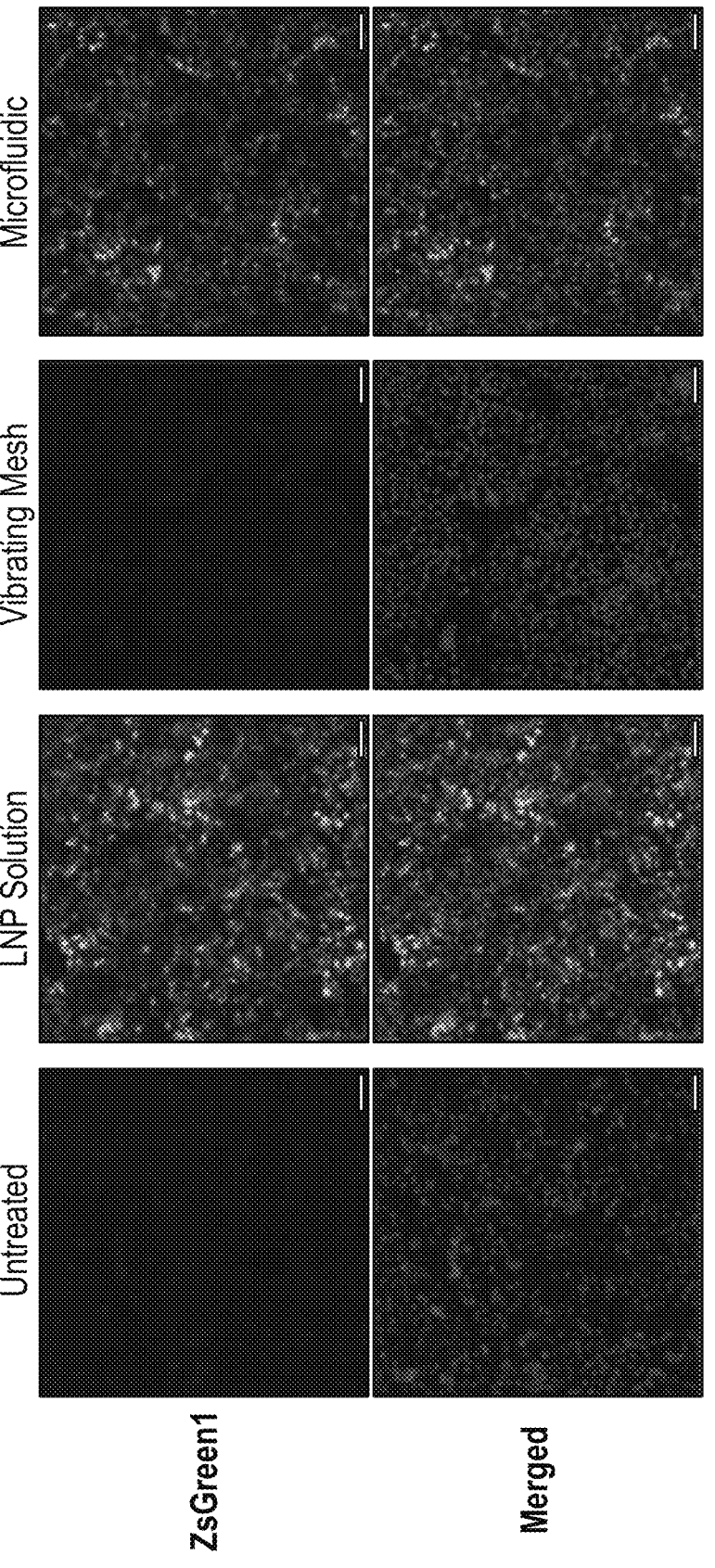
FIG. 4D are fluorescence images of cells exposed to untreated droplets, an LNP solution, droplets created by the vibrating mesh nebulizer, and droplets created by the microfluidic aerosolization system.
Figure 4E:
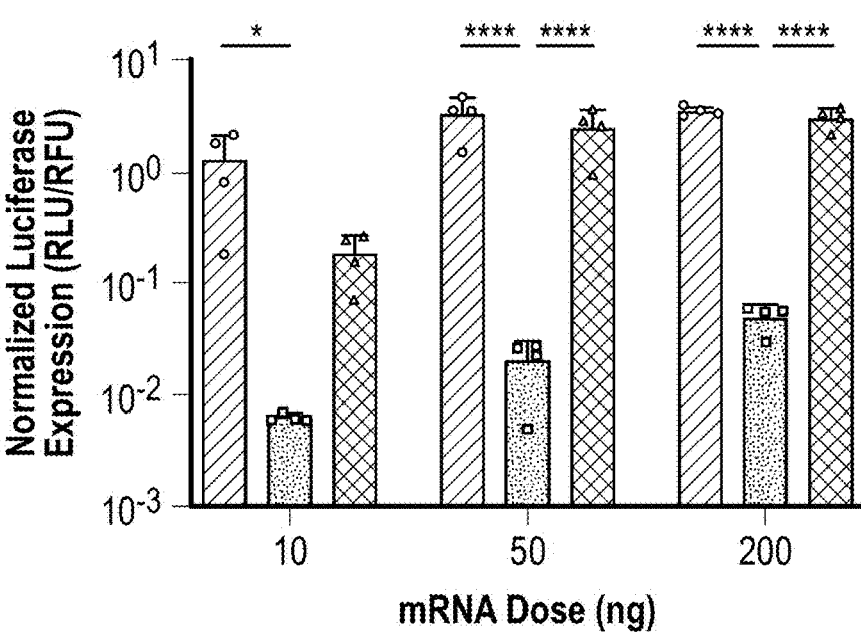
FIG. 4E plots mRNA transfection of the experiment of FIG. 4D.
Figure 4F:
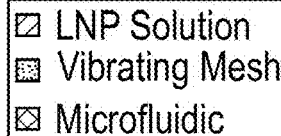
FIG. 4F plots mRNA transfection efficiency across five different cell lines.
Figure 22:
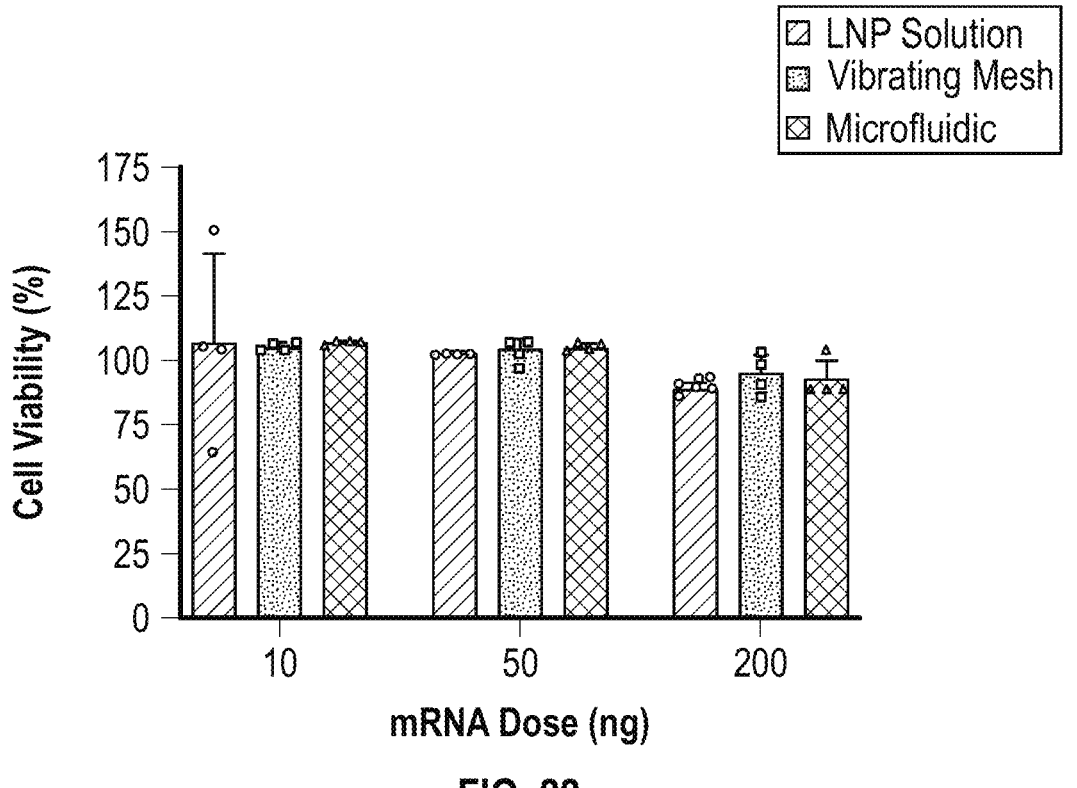
FIG. 22 plots cell viability in response to LNP transfection with nebulized LNPs.
Figure 23A:
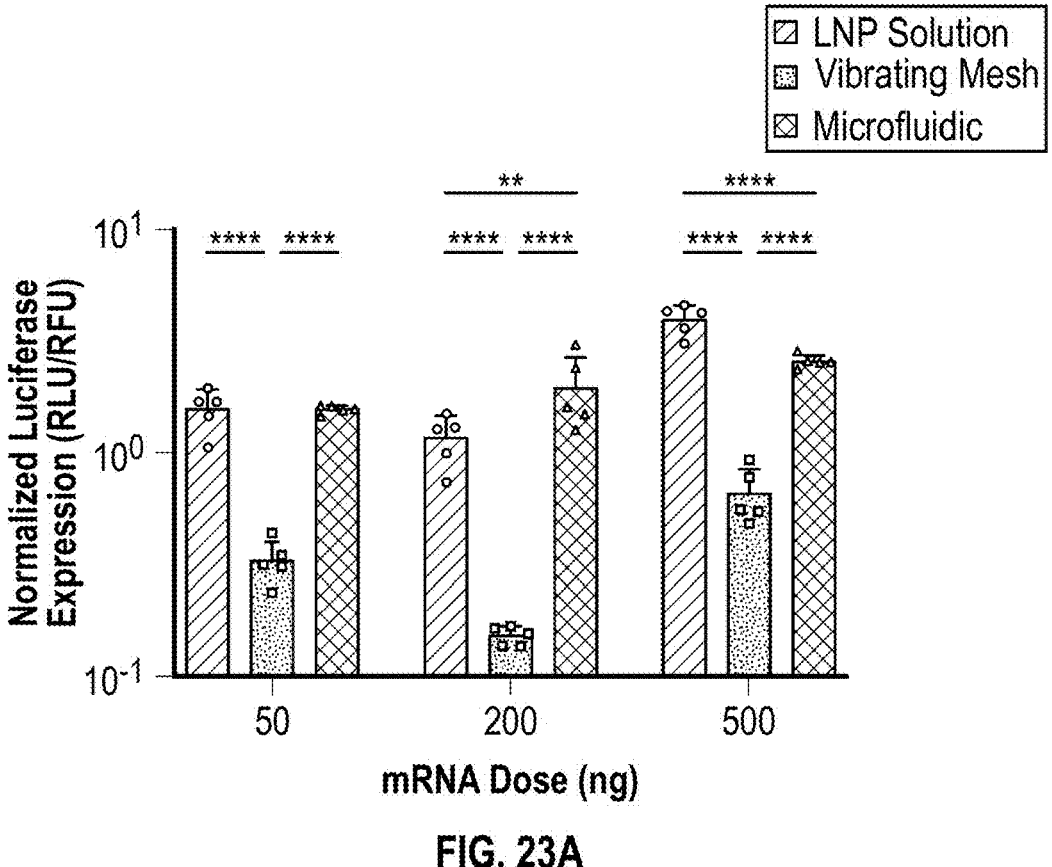
FIG. 23A-23B are plots showing the effects of nebulized LNP delivery to relevant lung cell line.
Figure 23B:
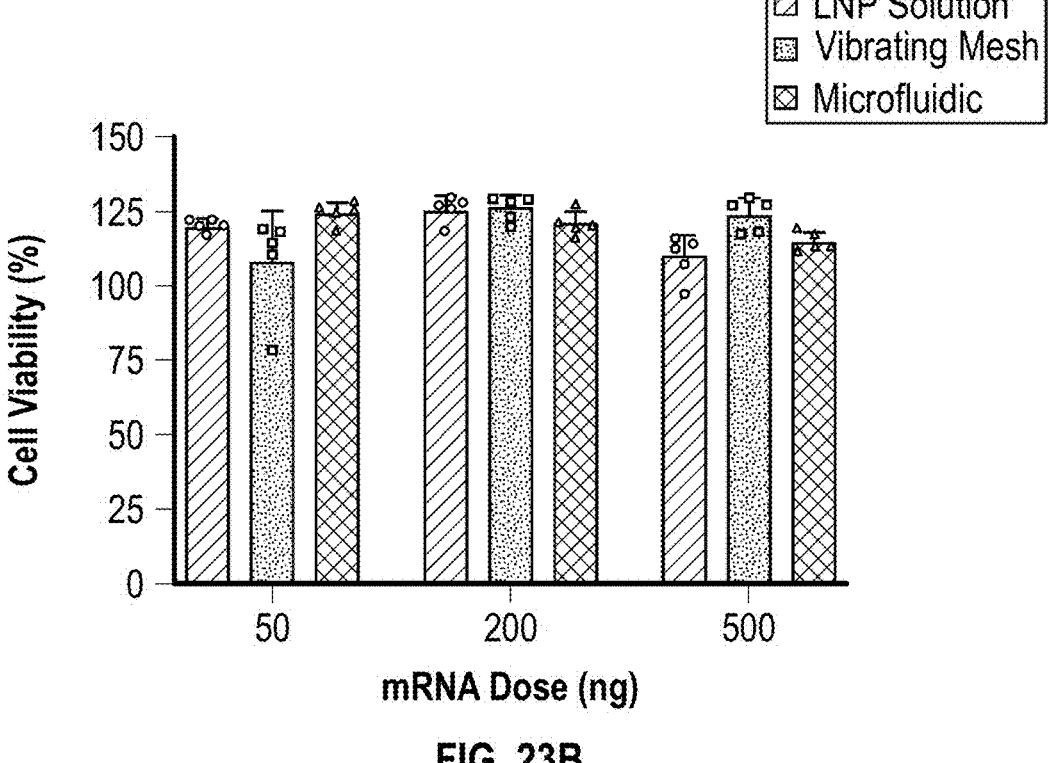
Figure 24:
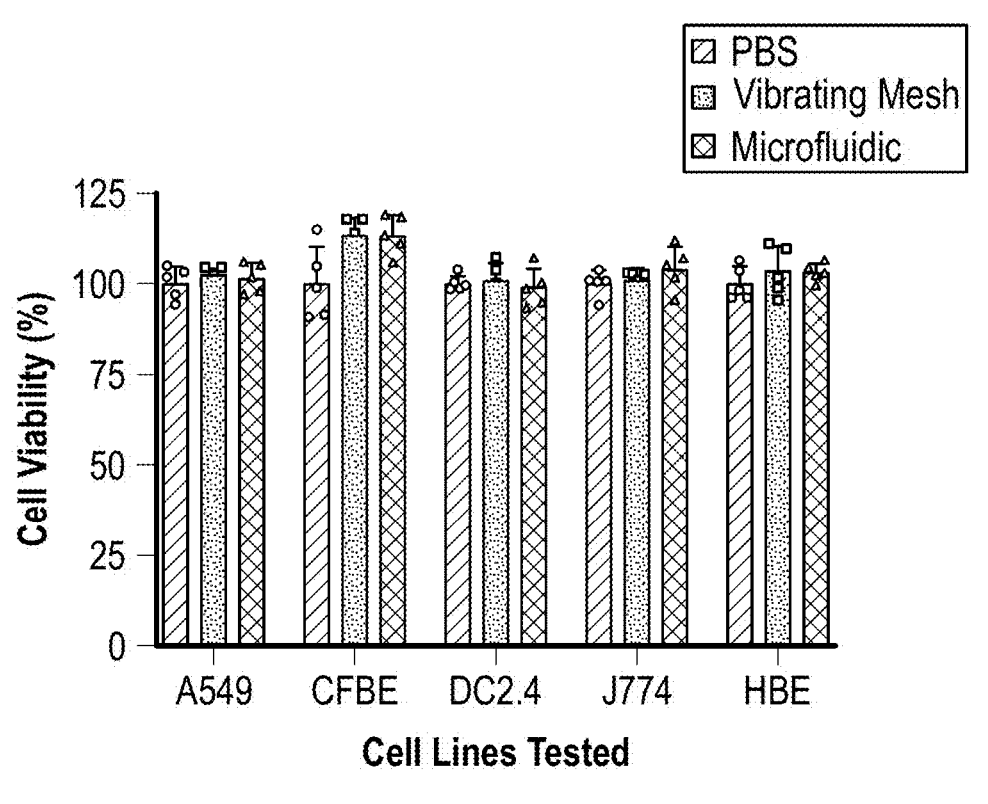
FIG. 24 plots cell viability of various cell lines after treatment with nebulized LNPs.
Figure 25B:
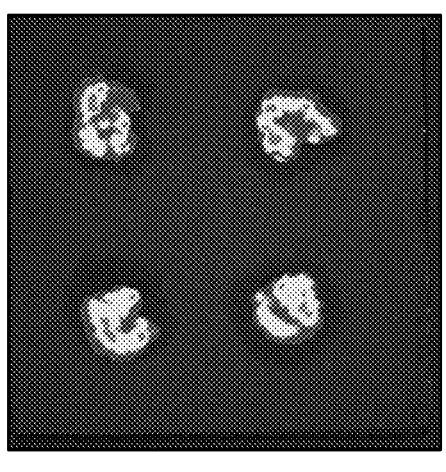
FIG. 25A-25B are images image showing lung delivery of aerosolized LNP/Nluc by spontaneous inhalation to mouse lungs.
Figure 25B:
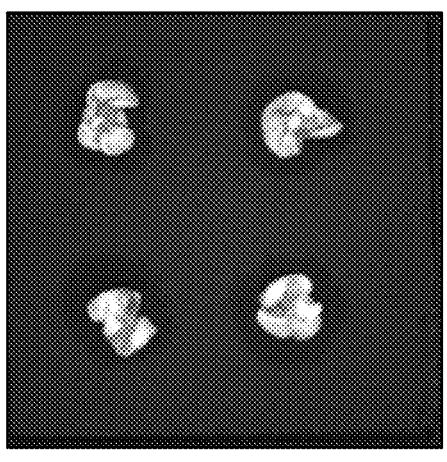
Figure 25A:
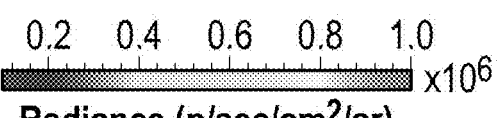
Figure 25C:
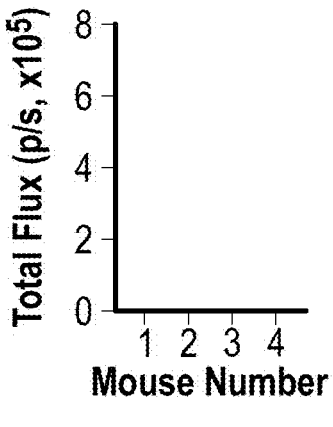
FIG. 25C plots quantified luminescent signals from the captured images.

Without being tied to a particular theory, the intact nano- structure provided from microfluidic platform may produce greater mRNA transfection than the damaged nanostructure by mesh nebulizers. To validate this assumption, 293T/17 cells were treated with LNPs containing ZsGreen1 mRNA (LNP/ZsGreen1) with or without aerosolization. After 24 h incubation post-treatment, ZsGreen1 mRNA transfection was assessed using fluorescence microscopy. The negative control group showed no green fluorescence, while the cells treated with the LNP/ZsGreen1 solution exhibited bright green fluorescence across the field of view (FIG. 4D). When comparing the vibrating mesh nebulizer and the microfluidic platform, it became evident that the latter resulted in a greater expression of ZsGreen1 protein in the treated cells (FIG. 4D). Moreover, the level of ZsGreen1 expression observed in cells treated with aerosolized LNP/ZsGreen1 using the microfluidic platform looked comparable to that of cells treated with the LNP/ZsGreen1 solution. It suggests that the aerosolization of LNP/mRNA by the microfluidic platform has little impact on the efficiency of nanoparticle- mediated mRNA delivery to cells. On the other hand, vibrating mesh nebulizers noticeably hindered in vitro mRNA transfection by nanoparticles during aerosolization. Additional measurements were conducted to examine the advantages of the microfluidic platform compared to vibrating mesh nebulizers in mRNA delivery. When delivering firefly luciferase (Fluc) mRNA instead, consistent patterns were found again. In 293T/17 cells, the group treated using the vibrating mesh nebulizer showed a nearly 100-fold reduction in mRNA transfection compared to the LNP solution treatment group (FIG. 4E). In contrast, the group treated with the microfluidic platform displayed mRNA transfection levels similar to the LNP solution treatment group, albeit an approximately 7-fold decrease observed only in the lowest mRNA dose (FIG. 4E). All treatments had little effect on the cell viability of 293T/17 cells (FIG. 22). To corroborate the benefit of the microfluidic platform in aerosolizing LNP/mRNA, the experiments were iterated in more biologically relevant cells. In human bronchial epithelial cells (16HBE14o-), the microfluidic platform showed comparable efficiency in delivering mRNA to that of the LNP solution treatment (FIG. 23). By contrast, the vibrating mesh nebulizer significantly impaired the nanoparticles' ability to deliver mRNA across all tested mRNA doses. The subsequent screening across various cell lines exhibited similar results, demonstrating that the microfluidic platform achieved mRNA delivery efficiencies approximately 5 to 187 times higher than the vibrating mesh nebulizer (FIG. 4F and FIG. 24). In sum, microfluidic platforms in accordance with the present disclosure clearly demonstrated significant advantages over the vibrating mesh nebulizer, as it displayed superior efficiency in delivering mRNA to cells.

Having established the overall relative advantages of microfluidic platforms in accordance with the present disclosure in generating nanoparticle-containing aerosols, mRNA was delivered to the mouse lungs. For this purpose, a whole-body rodent inhalation system was employed, which included a 3 L container connected with the microfluidic platform (FIG. 5A). This system facilitated the controlled administration of aerosolized LNP/mRNA to the mice, enabling the evaluation of its potential applicability for inhalable mRNA therapy. The microfluidic platform was programmed through the controller to generate a plume, and the cartridge was loaded with LNPs containing Nluc mRNA (LNP/Nluc). The mice were placed inside the chamber and exposed to the aerosol containing LNP/Nluc, after which they spontaneously inhaled the nanoparticles. To confirm the successful pulmonary delivery of mRNA to the lungs using the rodent inhalation system facilitated by a microfluidic platform in accordance with the present disclosure, RNAScope in situ hybridization (ISH) analysis was conducted.

Figures 5B, 5C:
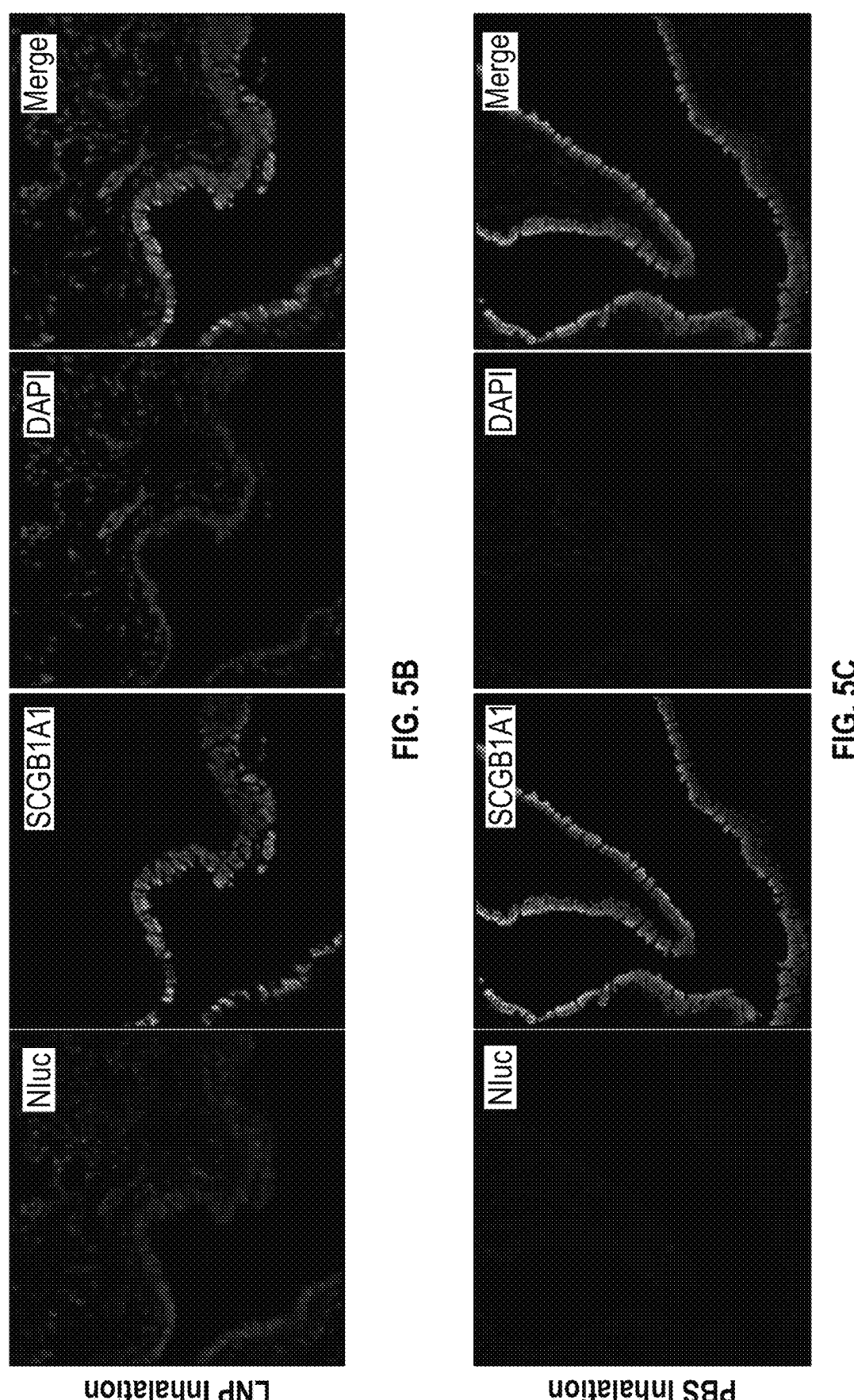
FIG. 5B are confocal images of mouse lung tissue showing the presence of Nluc transcripts throughout the lungs that were exposed to LNP/Nluc aerosol.
FIG. 5C are confocal images showing no signal detected in the lungs exposed to PBS aerosol.
Figure 5H:
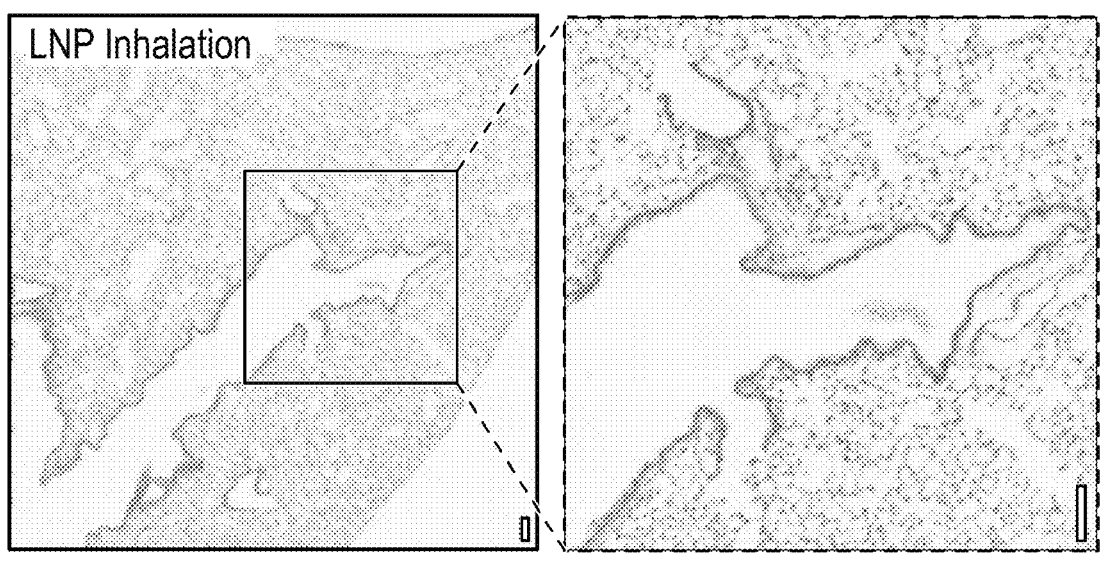
FIGS. 5I and 5H show histopathological images of mouse lung exposed to LNP/Nluc aerosol containing 1 mg of mRNA (FIG. 5H) or an equivalent volume of PBS (FIG. 5I).
Figure 5I:
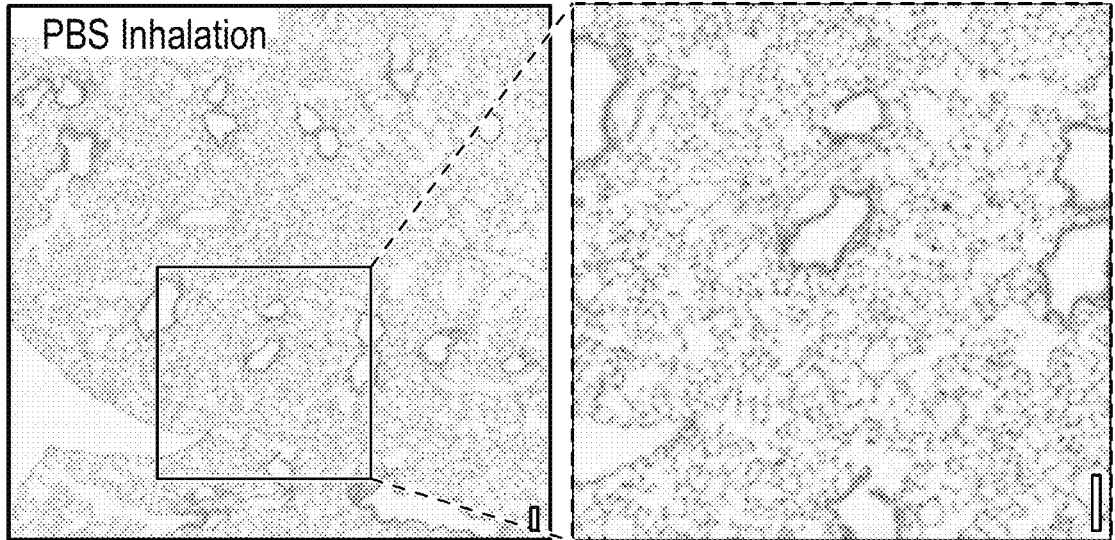

LNP/Nluc containing 1 mg of mRNA was aerosolized into the chamber and allowed the mice to inhale the aerosols. After 24 hours, the mouse lungs were collected, fixed, and sections were prepared for staining. Using confocal imaging, the presence of Nluc mRNA transcripts in the lungs was visualized. Additionally, club cells, a specific type of bronchial epithelial cells, were labeled to assess the distribution of Nluc mRNA transcripts within the epithelial tissues of the lungs. The confocal images clearly showed the presence of Nluc transcripts throughout the lungs that were exposed to LNP/Nluc aerosol (FIG. 5B). In contrast, no signal was detected in the lungs exposed to PBS aerosol, validating the specificity of the assay (FIG. 5C). Moreover, the delivered Nluc mRNA transcripts were predominantly localized in the club cells, suggesting that the inhaled mRNA was effectively deposited in the lung epithelial tissues (FIG. 5C). These findings strongly support that a microfluidic platform in accordance with the present disclosure produced aerosols fine enough to reach the lung epithelial cells of mice through spontaneous respiration, validating its efficacy in pulmonary mRNA delivery. To evaluate the effectiveness of the delivered mRNA in cell transfection, bioluminescence imaging on the collected lungs was conducted. Similarly, LNP/Nluc was aerosolized into the chamber, delivering a dose of 1 mg Nluc mRNA. After 24 hours post-inhalation, the mouse lungs were imaged ex vivo. The bioluminescence imaging showed consistent luciferase expressions in the collected lungs among all the mice. This consistent expression in the lungs supports the robust performance of a microfluidic platform in accordance with the present disclosure in delivering mRNA to the lungs and achieving successful protein expression in the respiratory tissues of mice (FIG. 25). Further investigations were conducted to assess whether mRNA transfection was dose-dependent. The results demonstrated that the Nluc expressions in the lungs were directly proportional to the dose of LNP/Nluc aerosolized (FIGS. 5D and 5E). This indicates that increasing the dose of LNP/mRNA led to a corresponding increase in the protein expression in the lungs. In addition, the site of mRNA transfection through inhaled LNP/Nluc was exclusively confined to the lungs (FIG. 5D). The conventional LNP formulation containing DLin-MC3-DMA exhibits inherent tropism for transfection to the liver when administered systemically. However, results corroborate that inhaled LNPs can deliver mRNA to the respiratory system, consistent with previous studies. Luminescence measurements were conducted at both 24 hours and 48 hours after treatment. It was shown that luciferase expression was higher at 24 hours post-treatment compared to 48 hours post-treatment (FIGS. 5F and 5G). This observation indicates the transient nature of mRNA transfection, with the expression of the delivered mRNA reaching its peak at an earlier timepoint before gradually declining over time. Subsequently, the possibility of acute lung damage following LNP/Nluc inhalation was examined through histopathology. The mice were exposed to LNP/Nluc aerosol containing 1 mg of mRNA (FIG. 5H) or an equivalent volume of PBS (FIG. 5I). After 24 hours of treatment, the lungs were collected, lung sections were prepared, and were stained with hematoxylin and eosin (FIGS. 5H and 5E) to assess any potential histological changes or tissue damage. In the H&E-stained lung sections, the lungs of both groups appeared histologically normal. However, in both groups, minimal mononuclear cell infiltrates around the terminal bronchioles, interstitium, or peribronchiolar areas were observed (FIG. 26). Furthermore, the lungs showed a slight increase in lymphocytes in the bronchus-associated lymphoid tissues, but there was no significant difference between the two groups, suggesting that these abnormalities were likely artifactual findings and not related to the treatment. These minor changes could be attributed to the excessive accumulation of liquid in the tissues, resulting in mild congestion in the lungs. Overall, these findings collectively reinforce the pulmonary efficacy of a microfluidic aerosolization platform in accordance with the present disclosure, offering a safe, effective, and straightforward means of delivering mRNA therapies for respiratory conditions while avoiding unwanted effects in other organs.

Materials and Methods

Discussed herein are a number of working examples. The working examples are not intended to limit the scope of the disclosure, but are intended to illustrate various aspects. Any features discussed with reference to the working examples below can be combined with embodiments discussed elsewhere this disclosure, and vice versa.

Materials

Firefly luciferase (Fluc) mRNA was purchased from Tri-link Biotechnologies. Cholesterol was obtained from Sigma-Aldrich (MO, USA), and DSPE-PEG2K and DMG-PEG2K were purchased from NOF America. DLin-MC3-DMA was purchased from Biofine International Inc. (BC, Canada). 1,2-distearoyl-sn-glycero-3-phosphocholine (DSPC), 1-palmitoyl-2-oleoyl-sn-glycero-3-phosphocholine (POPC), 1,2-dioleoyl-sn-glycero-3-phosphoethanolamine-N(lissa-mine rhodamine B sulfonyl) (Rhod-PE) and 1,2-dioleoyl-sn-glycero-3-phosphoethanolamine-N-(7-nitro-2-1,3-ben-zoxadiazol-4-yl) (NBD-PE) were obtained from Avanti Polar Lipids, Inc. (AL, USA).

Characterization of Droplets Generated by a Microfluidic Aerosolization Platform Liposomes were prepared as a substitute to LNPs in the characterization of droplet formation by a microfluidic aero-solization platform. Briefly, the lipid phase consisted of the following components: DSPC, cholesterol, and DSPE-PEG2K, in a 52:45:3 molar ratio, and was diluted to 25 mM in EtOH/DMF mixture (97.5:2.5). Sterile PBS and lipid solutions were heated at 65° C. and mixed at a 2:1 volu-metric ratio using a NanoAssemblr Benchtop system (Pre-cision Nanosystems, BC, Canada), followed by overnight dialysis against sterile PBS at 4° C. in 10 kDa Slide-a-Lyzer G2 cassettes (Thermo Fisher, MA, USA). The batch size of liposomes was 1.2 L in total. Hydrodynamic size and polydispersity of the liposomes were determined with DLS in a Zetasizer Nano ZSP device (Malvern Panalytical, UK).

Droplet formation and ejection was evaluated using the drop watcher system (JetXpert Dropwatcher, ImageXpert, NH). Droplets that were dispensed by the microfluidic head were examined, and the behavior of a single drop was captured using the drop watcher camera. The system was calibrated to a ratio of 1 pixel to 0.001034 mm using internal software and a calibration target provided by the manufac-turer. A known-width slit was imaged at a determined magnification and working distance. It allows for the deter-mination of droplet sizes and the estimation of droplet volumes using the software provided by the manufacturer.

Droplet size was measured using Spraytec® droplet size measurement system (Malvern Panalytical, UK). The sys-tem measures size distribution of sprayed droplets via their laser diffractions. This requires the angular intensity of light scattered from a spray to be measured as it passes through a laser beam. The recorded scattering pattern is analyzed and plotted using the manufacturer's software.

The thermal simulation was conducted using a proprietary FMS ejector modeling code (Funai Lexington, KY) with the following settings: bubble detachment time of 1236 ns, voltage of 11V, chip temperature of 45° C., pre-pulse dura-tion of 200 ns, pulse delay of 800 ns, and main heat-pulse duration of 600 ns. A proprietary aqueous dye formulation with well-defined thermophysical properties was used to characterize the fluid dynamics of the microfluidic aero-solization platform. Data were plotted using Origin 2022 (ver. 9.9).

In Vitro Transcription of mRNA

In vitro transcription of mRNA was performed as describe. Briefly, a linearized plasmid containing nanolu-ciferase (Nluc) under a T7 promoter was used as a template for in vitro transcription. Nluc mRNA was synthesized using the HiScribe T7 high yield RNA synthesis kit (New England Biolabs Inc., MA, USA) with CleanCap Reagent AG (Tri-Link Biotechnologies) according to the manufacturer's instructions. Synthesized mRNA was purified using the Monarch RNA cleanup kit (New England Biolabs) and stored at −80° C. Concentration of Nluc mRNA was mea-sured using a multimode microplate reader (Tecan Trading AG, Switzerland). To visualize the mRNA and assess for degradation, agarose gel electrophoresis was performed. 1 µg of IVT mRNA or RiboRuler high range RNA ladder (Thermo Fisher, MA, USA) was denatured and loaded on 1.5% agarose-formaldehyde gel prestained with GelRed (Biotium, CA, USA). The gel was run at 85 V for 2 h, followed by UV visualization.

LNP Formulation

LNPs were prepared using microfluidic mixing as previ-ously described. Lipid phase consisted of the following components: DLin-MC3-DMA, cholesterol, DMG-PEG2K, and DSPC in a 50:38.5:1.5:10 molar ratio and were diluted to 5.5 mM in 100% ethanol. mRNA was diluted in sterile 50 mM citrate buffer. The mRNA and lipid solutions were mixed at a 3:1 volumetric ratio using a NanoAssemblr Benchtop system (Precision Nanosystems, BC, Canada), followed by overnight dialysis against sterile PBS at 4° C. in 10 kDa Slide-a-Lyzer G2 cassettes (Thermo Fisher, MA, USA).

LNP Characterization

Hydrodynamic size and polydispersity of the LNPs were determined with DLS in a Zetasizer Nano ZSP device (Malvern Panalytical, UK). Encapsulation of mRNA was quantitatively determined by a modified protocol using Quant-iT RiboGreen RNA assay kit (Thermo Fisher, MA, USA) and a multimode microplate reader. Encapsulation of mRNA was measured qualitatively before and after aero-solization using agarose gel migration.

LNP Acrosolization

To aerosolize LNPs through ultrasonication, LNPs were added to a vibrating mesh nebulizer (Acrogen, Ireland) dropwise as previously described[4]. For microfluidics-based aerosolization with the microfluidic device, LNPs were added to a single channel of the previously described microfluidic cartridge, connected to the microfluidic aero-solization platform (FMS, Lexington, KY). Droplet ejection was controlled using FMS-provided software with the fol-lowing settings: frequency of 1.2 kHz, target temperature of 25° C., voltage of 11V, preheat pulse conditioning of 100 ns, preheat pulse duration of 200 ns, main-heat pulse condition-ing of 800 ns, and main-heat pulse duration of 600 ns.

FRET-Based Lipid Membrane Fusion Assay

Lipid mixing and membrane fusion induced by shear stress during aerosolization were assessed using a FRET assay. Briefly, DOPE-conjugated FRET probes, NBD-PE and Rho-PE, were incorporated into FRET liposomes. This formulation causes a reduction in NBD fluorescence due to FRET to rhodamine. When lipid fusion occurred, an increase in NBD signal would be detected owing to the greater distance between the two probes. To prepare FRET lipo-somes, DOPC:NBD-PE:Rho-PE mixture was combined in chloroform at a molar ratio of 99:0.5:0.5 in a round-bottom flask. The chloroform was eliminated through constant air-flow and flask rotation, resulting in a uniform lipid firm on the flask bottom. Vacuum was applied for 2 h to ensure complete chloroform evaporation. After drying, the lipid film was sonicated for 20 min, hydrated with HEPES-buffered saline, and extruded using a mini extruder (Avanti Polar Lipids). The liposome solution was passed through a 100 nm membrane 11 times. Subsequently, FRET liposomes were mixed with LNP/mRNA at a 1:1 (v/v) ratio and exposed to different conditions: no treatment, 2% Triton X-100, 20-min bath sonication, vibrating mesh nebulizer, or microfluidic aerosolization platform. The resulting samples were added to a black 96-well plate (80 µl per well) for fluorescence measurement. Fluorescence measurement (F) was conducted on a multimode microplate reader at Ex/Em=465/535 nm. The results from no treatment and Triton X-100 treatment were set as negative ($F_{min}$) and positive control ($F_{max}$), respectively. Fusion % was calculated as $(F-F_{min})/(F_{max}-F_{min})\times100$.

Cryogenic Transmission Electron Microscopy (CryoTEM)

Following plasma cleaning of grids, 2 µl of sample was deposited onto the grid in the FEI Vitrobot chamber at 100% relative humidity and allowed to rest for 10 seconds. The grid was then blotted for 1 second with filter paper and subsequently plunged into liquid ethane cooled by liquid nitrogen. The frozen grids were inspected for visible defects and then intact grids were assembled into cassettes. CryoTEM acquisition was performed with a Glacios cryoelectron microscope equipped with a Gatan K3 camera at 200 kV.

Cell Culture

HeLa cells were gifted from Prof. Robert Langer at Massachusetts Institute of Technology. A549 cells were kindly provided by Prof. Adam Alani at Oregon State University. 16HBE14o- cells and CFBE41o- cells were from Prof. Kelvin MacDonald at OHSU. HEK293T/17 were purchased from American Type Culture Collection (ATCC). HeLa and HEK293T/17 cells were cultured in DMEM supplemented with 10% heat inactivated FBS, 1% penicillin/streptomycin, and 10 mM HEPES buffer. 16HBE14o- cells and CFBE41o- cells were maintained in MEM/EBSS supplemented with 10% heat inactivated FBS, 1% penicillin/streptomycin/glutamine, 1% sodium pyruvate, and 10 mM HEPES buffer. A549 cells were cultured with RPMI-1640 supplemented with 10% heat-inactivated FBS, 1% penicillin/streptomycin, and 10 mM HEPES buffer.

Characterization of In Vitro mRNA Delivery

Cells were seeded on a white 96 well plate at 4,000 cells/well, on a clear 12 well plate at 50,000 cells per well, or on an 8 well chamber microslide (Ibidi) at 40,000 cells per chamber, followed by overnight incubation for attachment. Aerosolization of mRNA was conducted with one of two methods: a vibrating mesh nebulizer (Aerogen, Ireland) and a microfluidic aerosolization platform (Funai Lexington, KY). Cells in particular plates were treated with corresponding doses of mRNA. For cells in the 96 well plate, nebulized particles were collected from output of nebulizing unit and added to seeded cells. For cells in the 12 well plate, nebulizing unit was held and dispensed mRNA encapsulating LNPs directly over cells, followed by a 24 h incubation. Cell viability and in vitro luciferase expression was evaluated via ONE-Glo+Tox luciferase reporter and cell viability assay kit (Promega) and a multimode microplate reader.

Animals

All animals studied were conducted at Oregon Health and Sciences University and approved by the Institutional Animal Care and Use Committee (IACUC, IP0001707).

In Vivo LNP/mRNA Delivery Through Microfluidic Aerosolization

For characterizing mRNA delivery to mice through aerosolized LNPs, a whole chamber aerosolization system was chosen as described[12]. Briefly, all mice of group were placed in a 3 L chamber at once. LNPs encapsulating mRNA were prepared at 0.25 mg/mL, diluted in PBS. LNPs were loaded into a microfluidic cartridge single channel at a volume of 200 µl at a time. LNPs were aerosolized into the chamber at a rate of 25 µl per 2 minutes until the total dose of mRNA 1 mg total delivered. All mice in group were unrestrained without sedation. After 24 h post-treatment, the animals were sacrificed, and the lungs were collected for further characterization. To detect Nluc expression in the lungs, the collected lungs were gently and briefly washed in sterile PBS, incubated in 200 µl of 40-fold dilution of Nano-Glo substrate (Promega) in PBS per lung at room temperature for 5 minutes. Ex vivo bioluminescent imaging was then conducted using the IVIS Lumina XRMS (PerkinElmer). Collected lungs were then homogenized by adding the lungs to vials, adding 150 µl PBS to each lung and completely homogenizing with a hand-held homogenizer over ice until a slurry is observed. Samples moved to microcentrifuge tubes were centrifuged at 17,000×g for 30 minutes at 4° C. On a white 96 well plate, 30 µl of the supernatant and 60 µl of 80-fold dilution of Nano-Glo substrate in PBS were incubated at room temperature for 5 minutes. Luminescence was read with a multimode microplate reader. Luminescence was normalized with total protein concentration, which was measured with a BCA protein assay kit (Thermo Fisher).

Histopathology

BALB/c mice were exposed to LNP/mRNA aerosols generated from the microfluidic device until the total dose of mRNA 1 mg total delivered or sterile PBS until the equal volume delivered. After 24 h, mice were humanely euthanized, and their lungs were perfused with sterile PBS through the right ventricle. A 20G catheter was inserted into the trachea for lung inflation using a 10% neutral buffered formalin solution under a pressure of 25 cm from the surgical plane. The inflated lungs were carefully removed, placed in tissue embedding cassettes, and immersed in 70% ethanol for the purpose of dehydration. Following this, the tissues were embedded in paraffin, sectioned, placed onto slides, stained using H&E, and coverslipped, enabling histopathological assessment (IDEXX BioAnalytics, MO, USA). Whole-slide imaging of the specimens was conducted using a slide scanner (Leica Biosystems), and the images were analyzed using Aperio ImageScope v12.4.6.5003 (Leica Biosystems) and Fiji.

RNAscope In Situ Hybridization

Delivered Nluc mRNA and endogenous scgbla1 mRNA transcripts that were present in formalin-fixed paraffin-embedded (FFPE) lung tissue sections were visualized using RNAscope Multiplex Fluorescent Reagent Kit v2 (ACD) according to the manufacturer's protocol. Nluc probe (Cat. No. 885981), and Scgbla1 probes (Cat. No. 420351-C3) were prepared, and tyramide signal amplification (TSA)-based Opal fluorophores, Opal 570 (Akoya Biosciences, #FP1488001KT, 1:800 dilution) and Opal 690 (#FP1487001KT, 1:1,500 dilution), were used to visualize Nluc and Scgbla1 transcripts. Confocal images were obtained with a ZEISS LSM 880 (Carl Zeiss AG).

FIGS. 1A-1D. Microfluidic system to aerosolize LNP/mRNA. (FIG. 1A) Microscopic images of a microfluidic chip cartridge containing 960 nozzles. The nozzles are arrayed into three fluid channels, each channel consisting of 2 columns of nozzles and each channel linked to separate fluid chambers. The diameter of each nozzle is approximately 10 µm. (FIG. 1B) Illustration of the cross-sectional view of an individual nozzle made using a conventional semiconductor CMOS process, proprietary FMS thin film processes, and proprietary FMS MEMS photolithography processes. The thin film consists of various layers, including a protective layer, cavitation layer, dielectric film, electrode, and heater film. Blue arrow indicates primary direction of bubble growth when the heater is actuated. (FIG. 1C) Illustration of the layer structure of the microfluidic cartridge head with a bubble. Scale bar indicates 10 µm. (FIG. 1D) Schematic illustration explaining the sequential mechanism of ejection (aerosolization) of LNP/mRNA droplets at the cross-section of a nozzle: (1) bubble nucleation, (2) bubble growth, (3) drop ejected, and (4) drop break off and refill.

FIGS. 2A-2H. Characterization of droplets produced from the microfluidic platform. Representative images of droplets from a single ejection at (FIG. 2A) 1 kHz and (FIG. 2B) 15 kHz frequencies. Black arrow indicates the direction of plumes. The volumetric percentage of each droplet was estimated from the captured images and recorded for each ejection at (FIG. 2C) 1 kHz and (FIG. 2D) 15 kHz. (FIGS. 2E and 2F) The laser diffraction-based determination of the size distribution of droplets ejected at frequencies of (FIG. 2E) 7.5 kHz and (FIG. 2F) 15 kHz. (FIGS. 2G and 2H) Electric-thermal simulation of variation of fluid temperature in thermal boundary layer during pulse according to the geometric dimension and time. (G) Response surface plot and (H) contour plot of fluid temperature during pulse. Time is presented as the duration from the start of pulse in nanoseconds (ns).

FIGS. 3A-3I. Physicochemical characterization of LNP/ mRNA aerosols produced by a conventional nebulizer and the microfluidic acrosolization platform. (FIG. 3A) A schematic representation of a single LNP/mRNA. PEG lipid (blue); ionizable lipid (green); structural lipid (pink); cholesterol (yellow). (FIG. 3B) Representative size distributions of LNP/mRNA for different treatments: no treatment (gray), vibrating mesh (red), and microfluidic platform (blue). (C—F) Changes in LNP/mRNA following acrosolization via a vibrating mesh (black) or microfluidic platform (blue): (FIG. 3C) size, (FIG. 3D) polydispersity index, (FIG. 3E) zeta potential (mV), and (FIG. 3F) mRNA encapsulation. (FIG. 3G) A representative image showing agarose gel electrophoresis analysis from various treatment conditions: 1) mRNA only, 2) untreated LNP/mRNA, 3) LNP/mRNA+ Triton X-100, 4) LNP/mRNA+vibrating mesh, and 5) LNP/ mRNA+microfluidic platform. (FIG. 3H) A schematic diagram of FRET-based lipid membrane fusion assay. (FIG. 3I) FRET-based assay results for lipid membrane fusion of LNP/mRNA exposed to different conditions.

FIG. 4A-4F. Performances of LNP/mRNA aerosols produced by the microfluidic aerosolization platform surpasses that of a vibrating mesh nebulizer. Cryogenic transmission electron microscopy (cryoTEM) images of LNP/mRNA (FIG. 4A) in solution, (FIG. 4B) after acrosolization by a vibrating mesh nebulizer, and (FIG. 4C) after aerosolization by the microfluidic platform. Scale bars indicate 50 nm. (FIG. 4D) Fluorescence microscopy images of Hela cells subjected to various conditions: untreated, treated with LNP/ZsGreen1 in solution, aerosolized by a vibrating mesh, and aerosolized by the microfluidic platform (from left to right) at a dose of 1 μg mRNA per chamber. Green represents ZsGreen1 proteins and blue represents nuclei. Scale bars indicate 200 μm. (FIG. 4E) Normalized luciferase expression of 293T/17 cells treated with LNP/Fluc solution (light blue), LNP/Fluc aerosolized by a vibrating mesh nebulizer (red) or the microfluidic platform (blue) at various mRNA doses. (n=4) (F) Normalized luciferase expression of various cell lines by LNP/Fluc aerosolized by a vibrating mesh nebulizer (red) or the microfluidic platform (blue) at a dose of 50 ng mRNA per well. (n=5) *p<0.05; p<0.01; **p<0.0001.

FIGS. 5A-5I. Effective mRNA delivery to the lungs using microfluidics-assisted aerosolization. (FIG. 5A) A schematic diagram of a whole-body rodent inhalation system, which consisted of a 3 L container connected with the microfluidic platform. (FIGS. 5B and 5C) Representative images of RNAscope in situ hybridization analysis of BALB/c mouse lung sections after inhalation of (FIG. 5B) LNP/Nluc inhalation or (FIG. 5C) sterile PBS using the microfluidic platform. Nluc mRNA transcript (red), SCGBIAl (green), and nuclei (blue). 20× magnification. (FIGS. 5D-5G) Ex vivo luminescence (FIGS. 5D and 5F) images and quantification (FIGS. 5E and 5G) in lungs after LNP/Nluc were aerosolized and administered to mice. (FIGS. 5D and 5E) The variations included changing the amounts of mRNA to be aerosolized when the images were taken at 24 h post-inhalation (FIGS. 5D and 5E), or conducting luminescence imaging at different time points when 2.0 mg of mRNA was aerosolized (FIGS. 5F and 5G). (n=2) (FIGS. 5H and 5I) Histopathological analysis of mouse lungs collected 24 h after (H) inhalation of LNP/Nluc when 1.0 mg of mRNA was aerosolized, or (FIG. 5I) inhalation of an equal volume of sterile PBS using the microfluidic platform. Scale bars indicate 100 μm.

Each ejector may be fluidically linked to separate fluid chambers. In some examples, the chip includes at least 50, 100, 200, 300, 400, 500, 600, 700, 800, 900, 960, 1000, 1100, 1200, 1300, 1400, 1500, 1600, 1700, or 1800 droplet ejectors, or in a range defined by any two of the preceding values. In some examples, the array includes 800 to 1200 droplet ejectors. In some examples, the array includes 900 to 1000 droplet ejectors. In some examples, the array includes 960 droplet ejectors. The droplet injectors may each be individually addressable, enabling the generation of droplet plumes containing LNP/mRNA.

The nozzle of each droplet ejector may have a diameter of 1, 2, 3, 4, 5, 6, 7, 8, 9, 10, 11, 12, 13, 14, 15, 16, 17, 8, 19, 20, 21, 22, 23, 24, or 25 μm, or a diameter within a range defined by any two of the preceding values. In some examples, the diameter of each nozzle may be between 5 and 15 μm. In some examples, the diameter of each nozzle may be between 8 and 14 μm. In some examples, the diameter of each nozzle may be between 9 and 13 μm. In some examples, the diameter of each nozzle may be about 10 μm. In some examples, the diameter of each nozzle may be about 12 μm. In some examples, the microfluidic chamber may have a diameter equal to or larger than that of the nozzle. In some examples, the microfluidic chamber may have a diameter larger than that of the nozzle.

PEG molarity can impact RNA delivery of aerosolized LNP/mRNA. The incorporation of PEG into LNPs can help maintain the nanoparticles' stability during self-assembly. In addition, PEG molecules hinder interactions between LNPs and serum proteins, extending the nanoparticles' circulation time. However, they also inhibit the formation of a biomolecular corona on the nanoparticle surface, which delays the LNPs' endocytosis and subsequent mRNA delivery. In the context of LNP nebulization, PEG molecules are considered to contribute to the recovery or stabilization of nebulized nanoparticles through steric effects. This intricate interplay of PEG in LNP chemistry adds complexity to the formulation design for inhalation. Even with meticulous optimization, the nebulization process compromises LNP integrity, thus obscuring the key traits necessary for effective lung transfection. The MAP can help to eliminate or minimize uncertainties in formulation discovery by preventing LNP deformation during nebulization.

Example Portable Nebulizer

One implementation of a portable, hand held nebulizer in accordance with the present invention is discussed below in connection with FIGS. 6-14.

Figure 6:
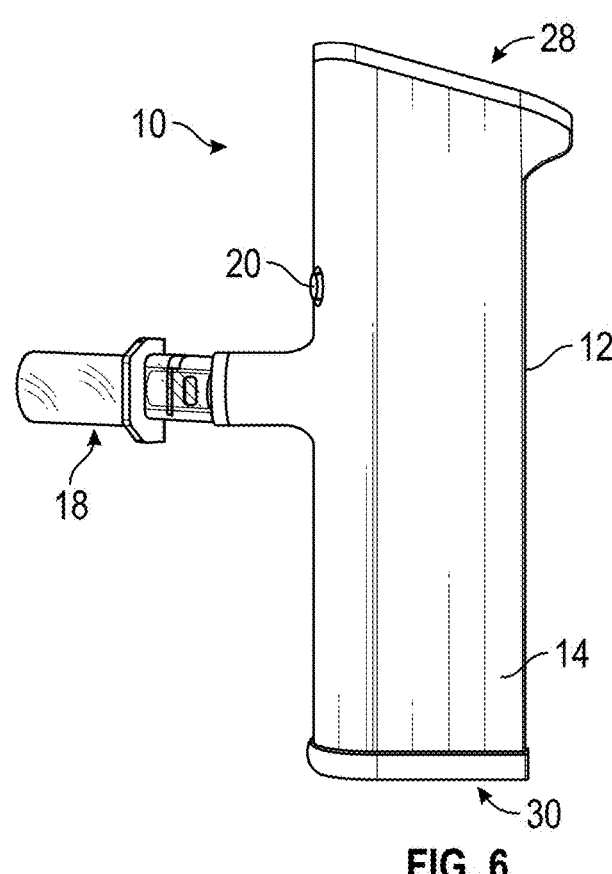
FIGS. 6-9 illustrate views of a portable aerosolizer.
Figure 7:
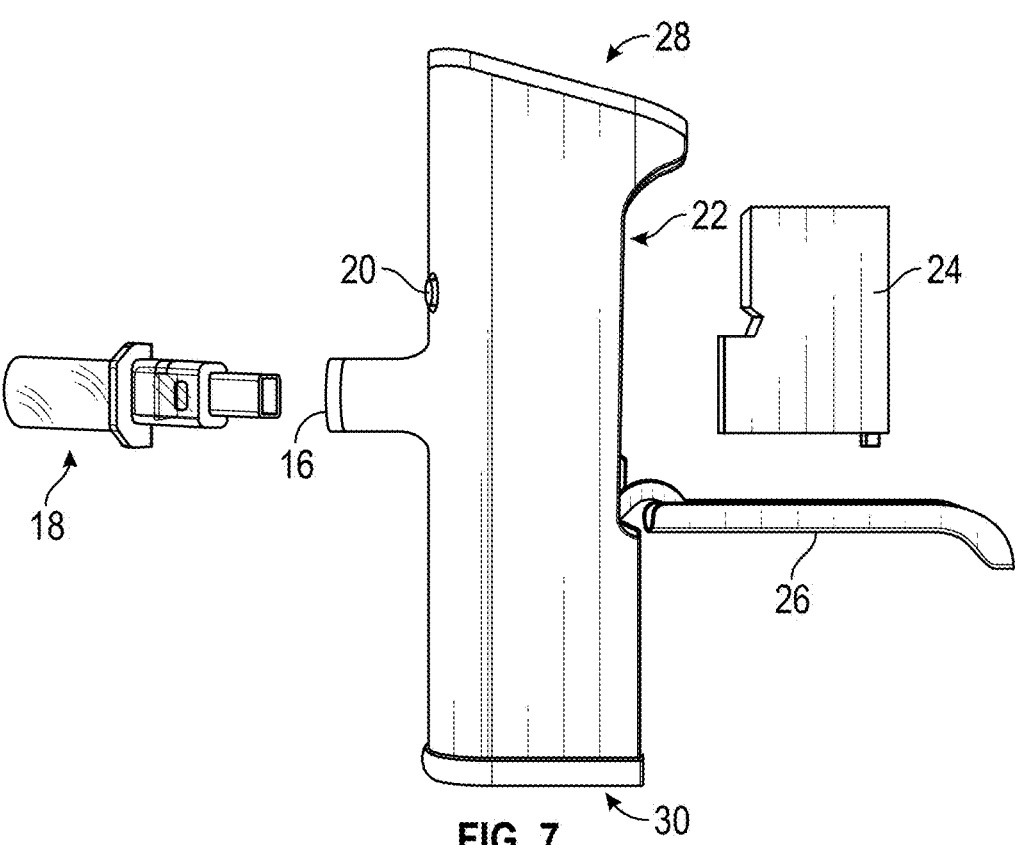

Referring to FIG. 6, there is illustrated one example of a microfluidic pulmonary drug delivery dispenser 10 in accordance with the present invention. The dispenser 10 includes a housing 12 which may have a handle 14. An effluent port 16 is carried by the housing 12 and can removably receive a mouthpiece 18. The dispenser 10 can discharge one or more pulmonary drug doses via the mouthpiece 18 and into a pulmonary system in response to activation of a discharge control such as a button 20 and/or a breath triggered trigger whereby the discharge is activated by the patient's inhalation thus enabling synchronized of the therapeutic with a patient's inhalation. While such breath-actuated inhalers (e.g.: U.S. Pat. No. 7,219,664B2) and breath-actuated nebulizers (eg: U.S. Pat. No. 11,266,795B2)_are known, the present technology is a novel application of a breath-actuated Microfluidic Aerosolizer.

The housing 12 may be provided with a docking structure such as an interior cavity 22 for removably receiving a cartridge 24 which contains a volume of one or more pulmonary drugs. The housing 12 may additionally be provided with a cover 26 for enclosing the cartridge 24 within the cavity 22. The cartridge 24 includes at least one reservoir and at least one microfluidic chip as will be discussed in greater detail below. When the cartridge 24 is seated within the cavity 22, a drug flow path extends from the reservoir(s), through the chip, out the effluent port 16 and through the mouthpiece 18 to the patient. Therapeutics from one or more reservoirs can be discharged sequentially or simultaneously according to pre-set configurations in the context of multi-fluid delivery applications. Further, the ratio of the different therapeutics from the different reservoirs, whether in a sequential or simultaneous discharge, can be configured to achieve different concentrations necessary for preferred clinical outcomes.

The cartridge 24 can be stored at up to −4° C. for up to 6 months and reused to discharge doses while maintaining clinical efficacy.

The housing 12 may additionally be provided with a display 28 for displaying progress and status of the dispenser 10. A microprocessor, power supply and associated electronics maybe carried within the housing 12. A charging connection such as an inductive coil or a charging port 30 such as a USB port may be provided to charge the internal power supply. An audible signal generator such as a tone generator or buzzer may be provided and activated at preset points in the operating cycle such as at the commencement of dose activation and completion of dose delivery.

Figure 8:
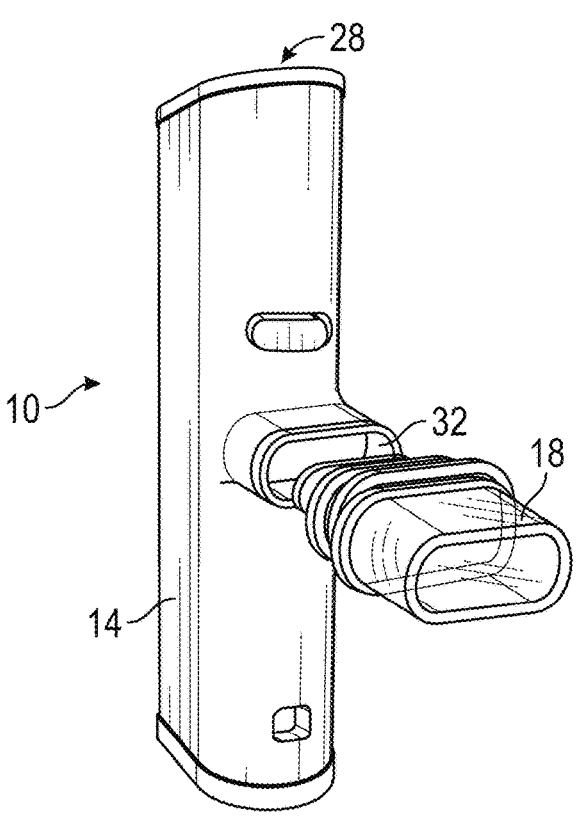
Figure 9:
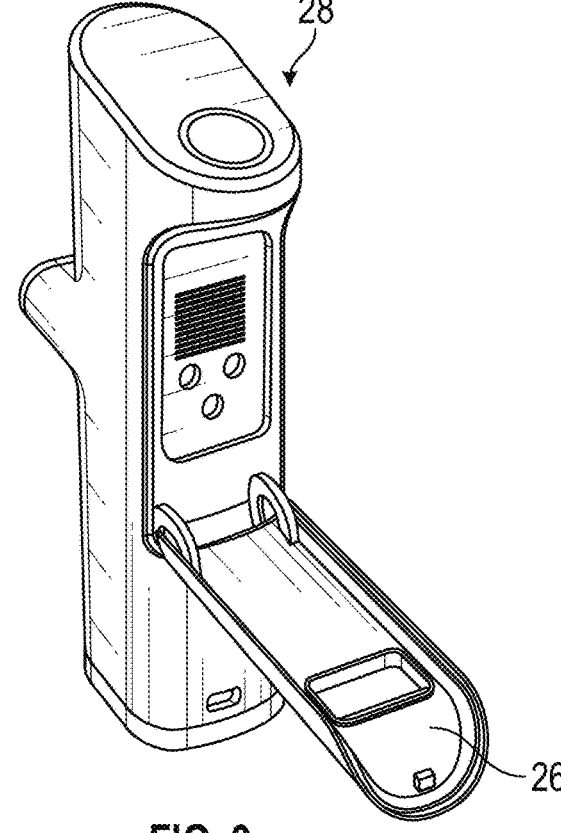
Figure 10:
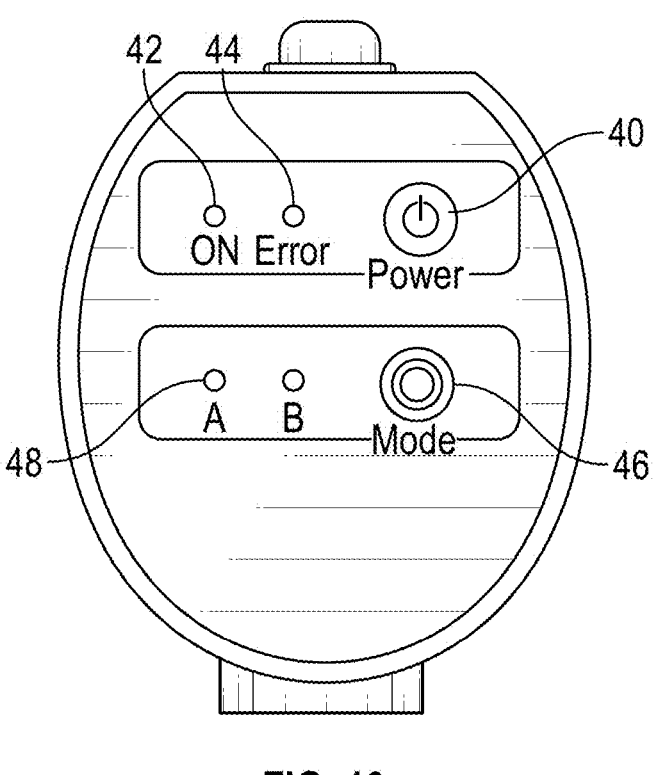
FIG. 10 illustrates a display and user controls of the portable aerosolizer of FIGS. 6-9.

Referring to FIG. 8, a plasma heat sterilization element 32 may be provided in communication with the flow path, downstream from the microfluidics chip and upstream from the effluent port 16. The plasma heat sterilization element, which quickly heat up to neutralize potential viruses or bacteria, can be activated in between uses or in between patients for cross-contamination purposes. Referring to FIG. 10, the user interface 28 may include a power control such as a button 40 and an on/off indicator 42 such as an LED. An optional error indicator 44 may also be provided, which may also be an LED. A mode select control 46 allows the user to switch between different dispense settings such as extended time dispense or dispensing from multiple reservoirs for a combination dose. One or two or more mode indicators 48 confirm the selected mode.

Figure 11:
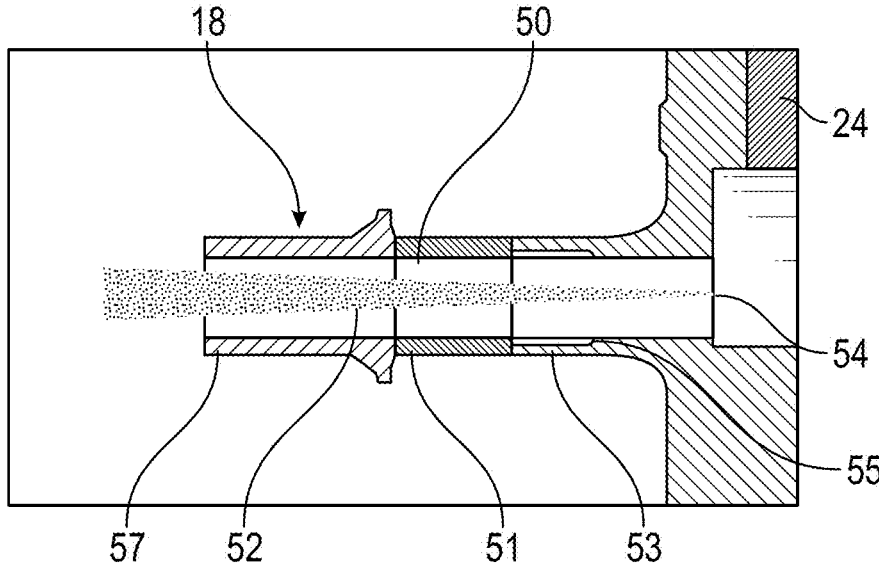
FIG. 11 illustrates airflow from a mouthpiece of the portable aerosolizer of FIGS. 6-9.

Referring to FIG. 11, the mouthpiece 18 may be provided with a one way valve 50 such as a shutter door, flap valve, duck bill or other valve configuration, which may open in response to forward velocity of the vapor plume 52.

Figure 12A:
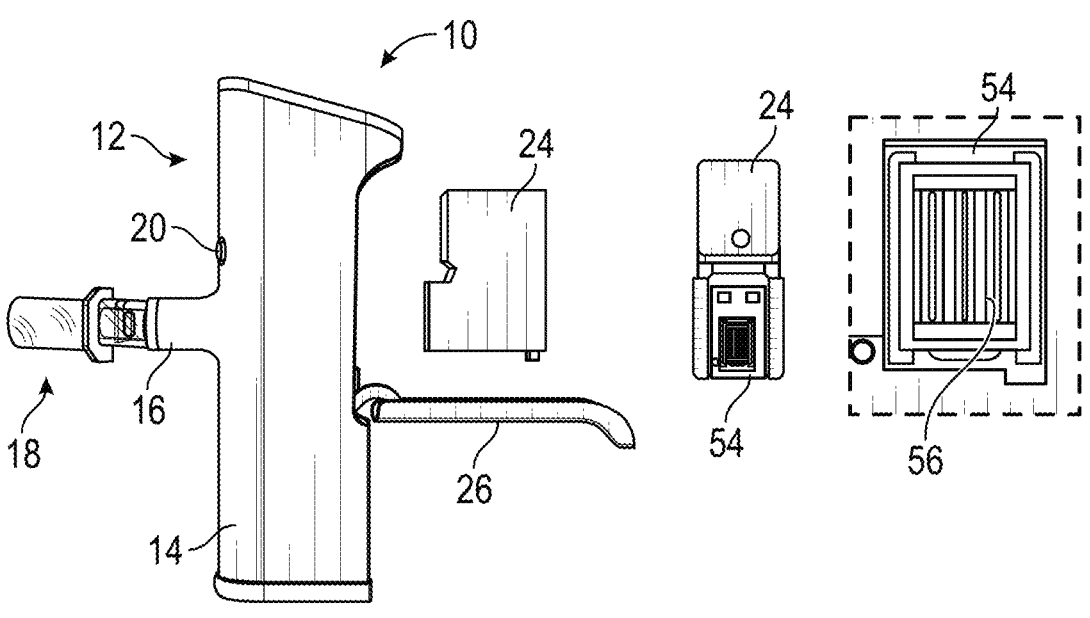
FIG. 12A illustrates an exploded side view of the portable aerosolizer of FIGS. 6-9.

FIG. 12A illustrates an exploded side view of the housing and cartridge, with a front elevational view of the cartridge and an enlargement of the microfluidics chip 54. The chip 54 carries a digitally addressable nozzle array 56 which may include at least about 100 or 200 and in some implementations at least about 300 or 400 or more individual nozzles 58. The microfluidics chip 54 may have a width within the range of from about 1 mm to about 10 mm, and in some implementations within the range of from about 3 mm and about 5 mm and in one implementation about 4 mm.

Figure 12B:
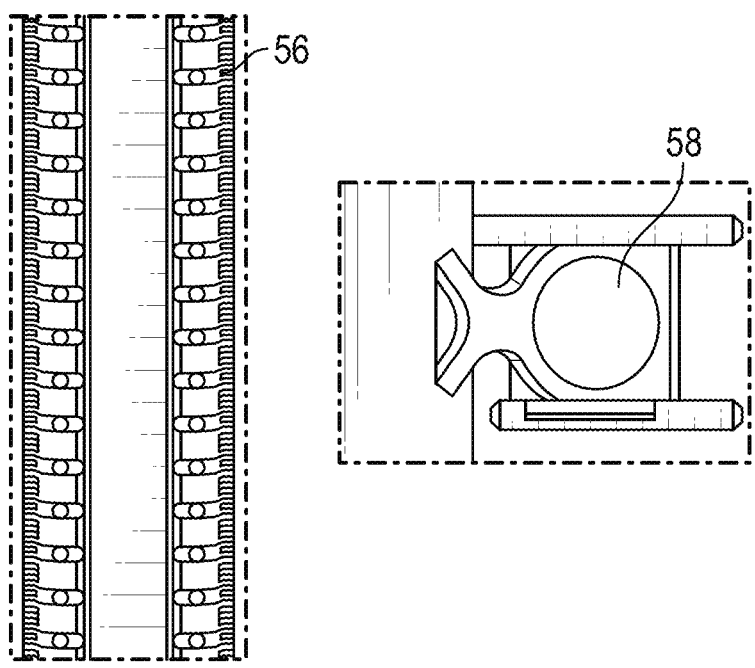
FIG. 12B illustrates two views of droplet ejectors of the portable aerosolizer of FIGS. 6-9.
Figures 13, 14:
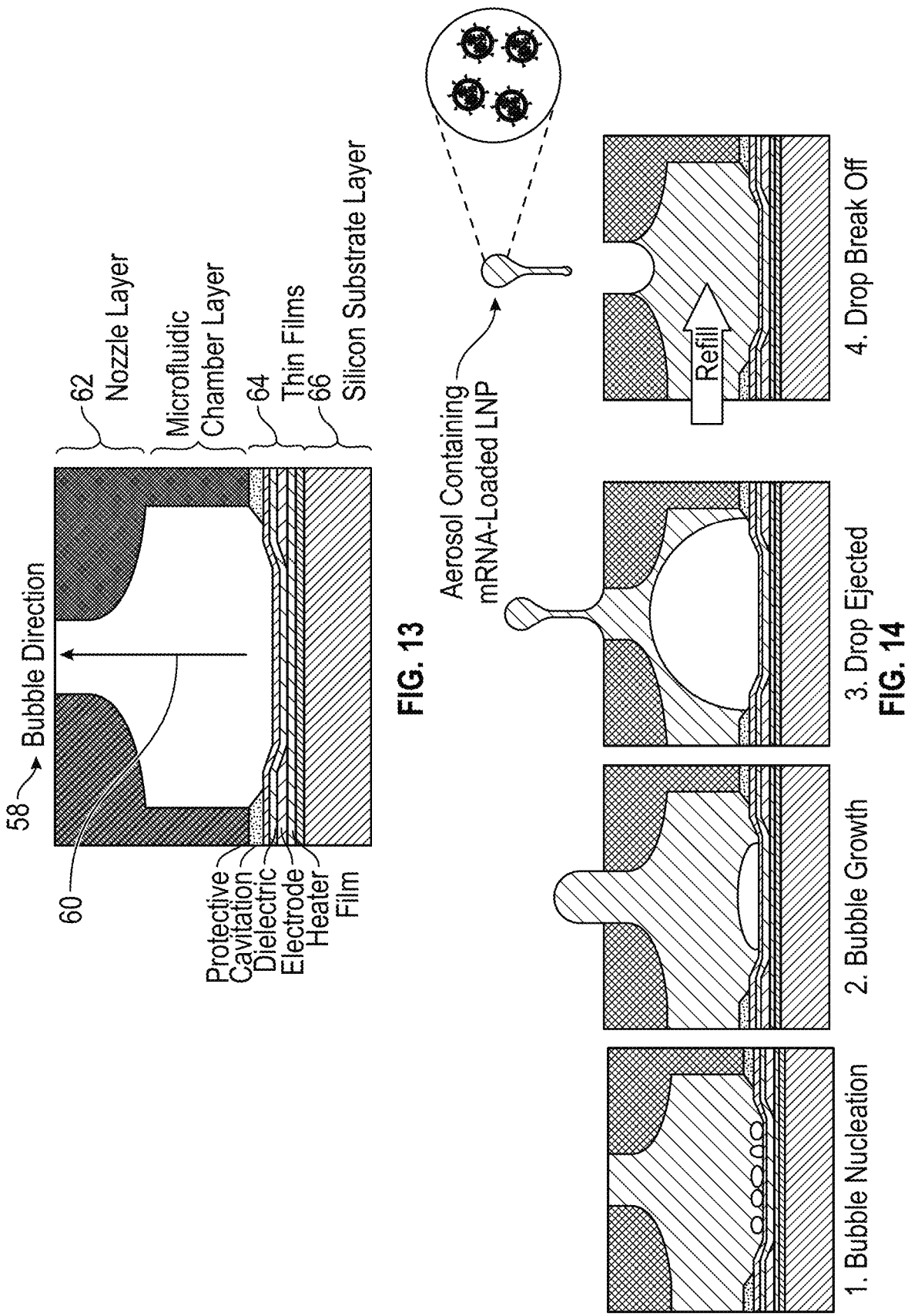
FIG. 13 illustrates a cross-sectional side view of a droplet ejector of the portable aerosolizer of FIGS. 6-9.
FIG. 14 illustrates a cross-sectional view of a droplet ejector of the portable aerosolizer of FIGS. 6-9 during the process of droplet nucleation.

Referring to FIGS. 12B and 13, each droplet ejector 58 has an nozzle 60 in communication with a microfluidic chamber 62 for expressing a liquid drug solution from the chamber and out through the nozzle 60. The opening may have a diameter within the range of from about 10 microns to about 100 microns depending upon desired performance. The droplet size may generally be less than about 30 microns and in some implementations is within the range of from about 7 to about 17 microns. A single nozzle ejection may run at a repeat rate of at least about 5,000 or 10,000 or 15,000 droplets or more per second to produce a throughput of at least about 20 or 25 or more microliters per second, having an initial velocity of about 8 to about 12 meters per second. Measured at 2 inches from the distal opening of the mouthpiece, the velocity is no more than about 1 meter per second, and generally no more than about 0.5 m/s or about 0.1 m/s, resulting in a soft, low velocity plume 52.

A thin film layer 64 is in thermal and/or mechanical communication with the microfluidic chamber 62 and supported by a substrate such as a silicon layer 66. The thin film layer 64 can eject a droplet of drug from the microfluidic chamber 62 and out through the droplet ejector 58 such as by the application of thermal or mechanical energy. In the illustrated implementation, the thin film layer 64 may include a heater layer to provide resistive heating in response to application of an electrical current. Mechanical energy may alternatively be supplied using piezoelectric or ultrasound transducers as will be understood in the art.

FIG. 14 shows a side elevational sequence of the droplet nucleation through ejection. Droplet nucleation begins upon the application of heat to a microfluidic chamber charged with drug. Further application of the heat causes droplet growth and ejection, resulting in a final droplet break off following exit from the droplet ejector 58, contributing to an aerosol plume containing mRNA loaded liquid nanoparticles.

Figure 15:
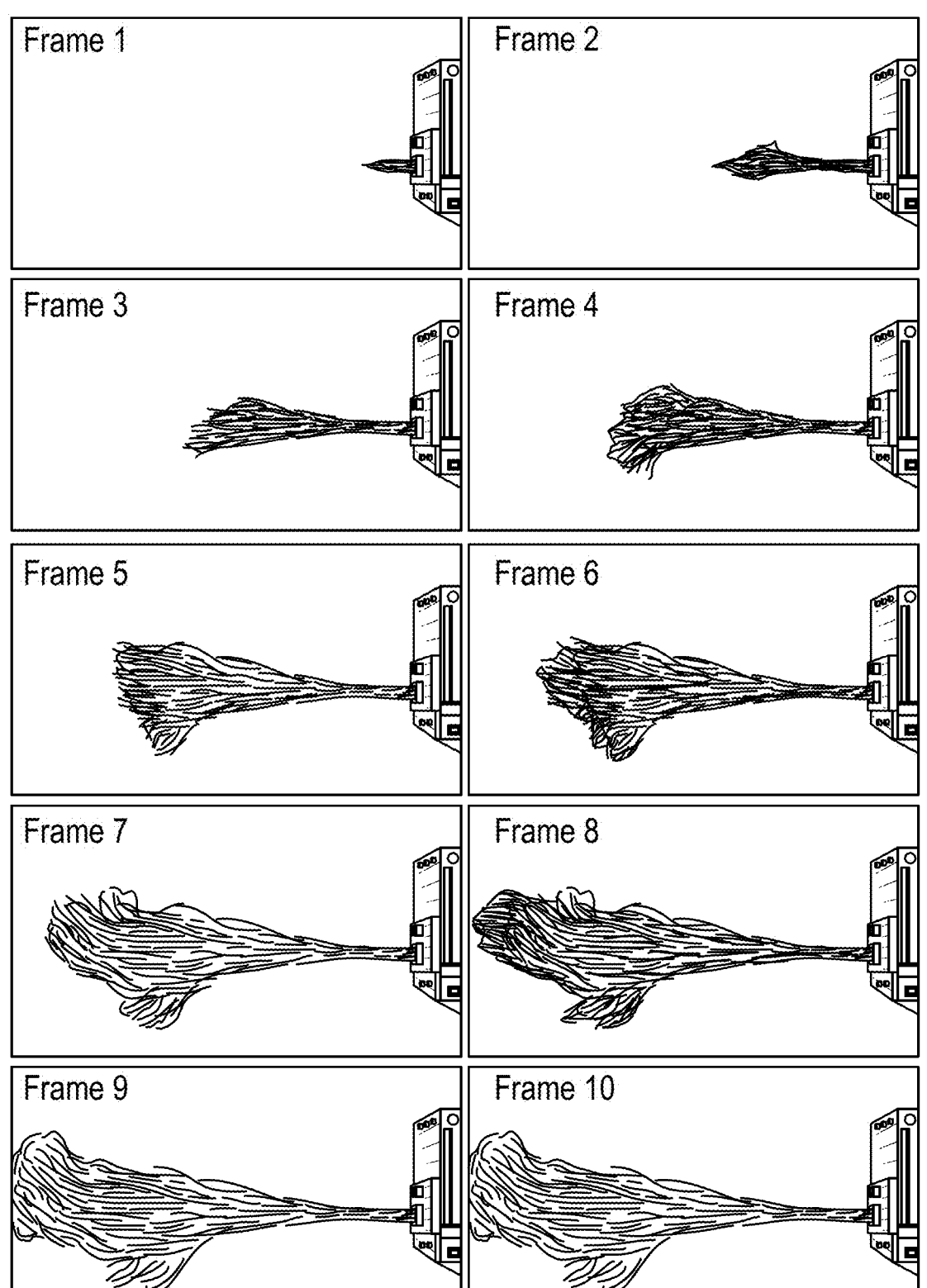
FIG. 15 is an image sequence of aerosol generation from the microfluidic device.

FIG. 15 is an image sequence of aerosol generation from the microfluidic device.

FIG. 16 plots a representative size distribution of liposomes.

FIG. 17 plots showing the size distribution of aerosol droplets at various distances from the device. Laser scattering was measured at various distances from the nozzle plates: 20 mm (red), 30 mm (blue), 40 mm (green), and 60 mm (magenta). Aerosolization was conducted from (A) all nozzles at 15 kHz (full), (B) half of the total nozzles at 15 kHz (spatial), or (C) all nozzles at 7.5 kHz (temporal).

FIG. 18 plots the size distribution of aerosol droplets by varying aerosolization frequencies or the number of nozzles. Aerosolization was conducted from all available nozzles at 15 kHz (red; full), half of the total nozzles at 15 kHz (blue; spatial), or all nozzles at 7.5 kHz (green; temporal). Laser scattering was measured at various distances from the nozzle plates: (A) 20 mm, (B) 30 mm, (C) 40 mm, and (D) 60 mm.

FIG. 19 plots the size distribution of aerosol droplets at various elapsed times of aerosolization. Laser scattering was measured at (A, C, E) 20 mm or (B, D, F) 60 mm from the nozzle plates. Measurements were recorded in the beginning (red), middle (blue), or end (green) of the dispense. Aerosolization was conducted from (A, B) all available nozzles at 15 kHz (full), (C, D) half of the total nozzles at 15 kHz (spatial), or (E, F) all nozzles at 7.5 kHz (temporal).

Figure 20:
FIG. 20 is an image of an agarose gel electrophoresis analysis of LNP encapsulation of mRNA after mesh nebulizer or microfluidic device aerosolization.

FIG. 20 is an image of an agarose gel electrophoresis analysis of LNP encapsulation of mRNA after mesh nebulizer or microfluidic device aerosolization. (A-C) Replicate samples: 1) mRNA only, 2) LNP before treatment, 3) LNP treated with Triton X-100, 4) LNP after nebulization with a vibrating mesh, and 5) LNP after microfluidic device. Yellow dotted line indicates gel image used in FIG. 3G.

Figure 21:
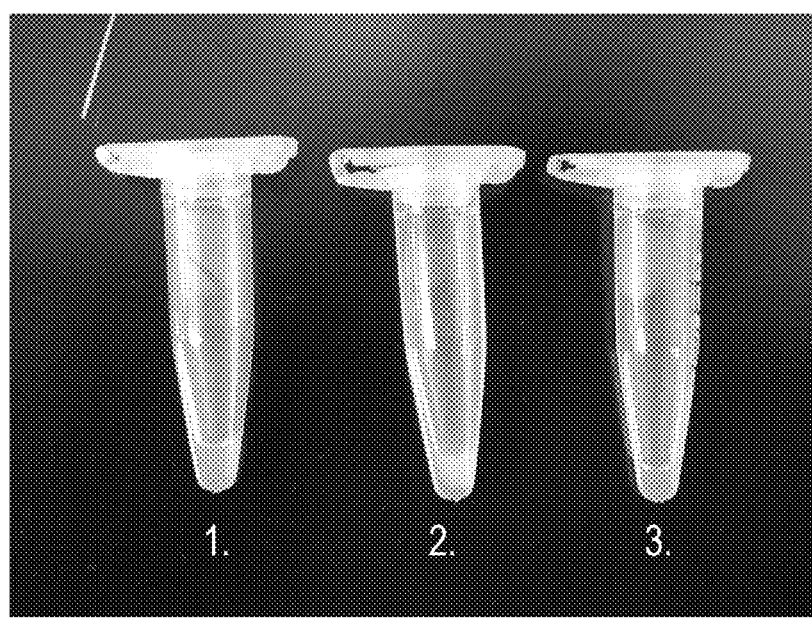
FIG. 21 are images showing the visual change in opacity of LNP solution after nebulization.

FIG. 21 are images of showing the visual change in opacity of LNP solution after nebulization or aerosolization. LNP solutions before (1) and after vibrating mesh (2) or microfluidic (3) aerosolization were imaged to show changes in opacity in the solutions.

FIG. 22 plots cell viability in response to LNP transfection with nebulized/aerosolized LNPs. Cell viability of 293T/17 cells treated with LNP/Fluc solution (grey), LNP/Fluc aerosolized by a vibrating mesh nebulizer (red) or the microfluidic platform (blue) at various mRNA doses. (n=4).

FIG. 23 plot the effects of nebulized/aerosolized LNP delivery to relevant lung cell line. (A) Normalized luciferase expression and (B) cell viability of human bronchial epithelium (16HBE14o-) cells treated with LNP/Fluc solution (grey), LNP/Fluc aerosolized by a vibrating mesh nebulizer (red) or the microfluidic platform (blue) at various mRNA doses. (n=5). *$p<0.05$; *$p<0.001$; **$p<0.0001$.

FIG. 24 plots cell viability of various cell lines after treatment with nebulized/aerosolized LNPs. Cell viability of various cell lines treated with PBS (grey), LNP/Fluc aerosolized by a vibrating mesh nebulizer (red) or the microfluidic platform (blue) at a dose of 50 ng FLuc mRNA per well (n=5). CFBE: CFBE41o- human bronchial epithelial cells, J774: mouse macrophage cells, and HBE: human bronchial epithelium 16HBE14o- cells.

FIG. 25 is an image showing lung delivery of aerosolized LNP/Nluc by spontaneous inhalation to mouse lungs. (A-C) Microfluidic device delivery consistency across all 4 mice in a whole-body rodent inhalation system. (A) Bioluminescent signals and (B) a photograph of the collected lungs. (C) Quantified luminescent signals in the captured images.

Figure 26A:
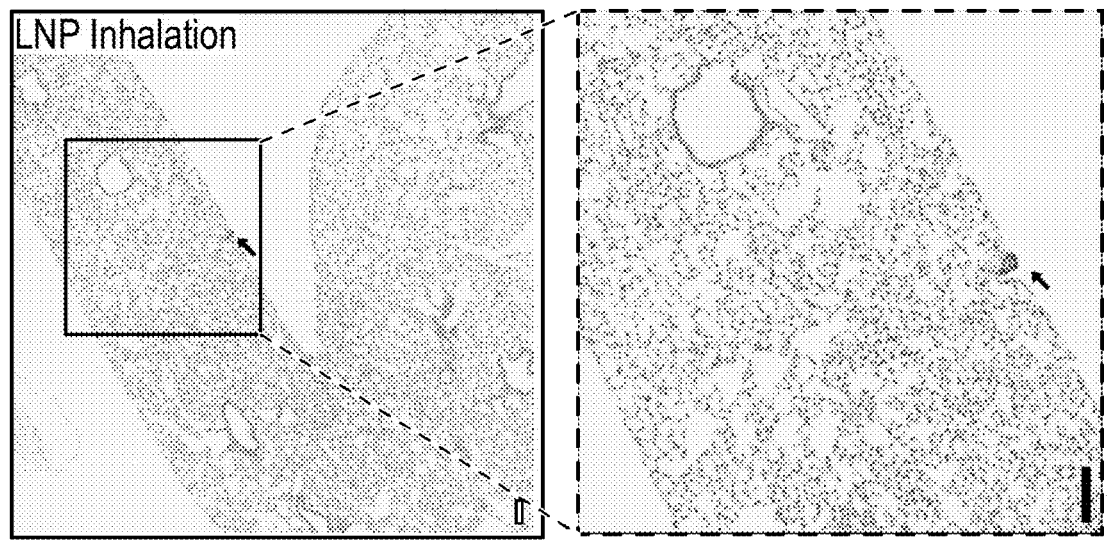
FIGS. 26A and 26B are histopathological images of mouse lungs collected 24 h.
Figure 26B:
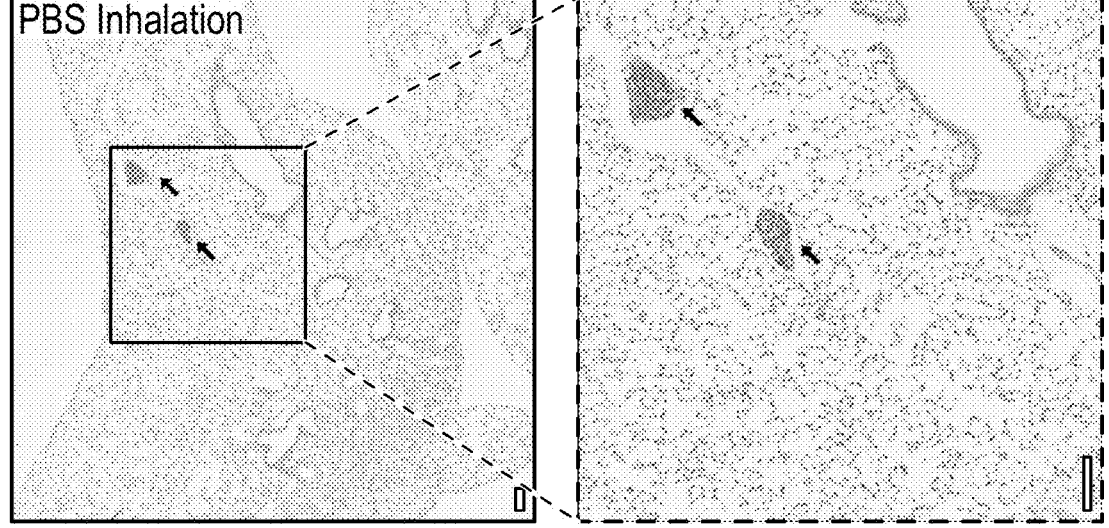

FIGS. 26A and 26B are histopathological images of mouse lungs collected 24 h. FIG. 26A shows inhalation of LNP/Nluc when 1 mg of mRNA was aerosolized. FIG. 26B shows inhalation of an equal volume of sterile PBS using the microfluidic platform. Insets indicate the area of interest. Arrows indicate minimal increases of lymphocytes in the bronchus-associated lymphoid tissue (BALT). Scale bars indicate 100 μm.

Terminology

"CF" refers to cystic fibrosis.

"CMOS" refers to complementary metal oxide semiconductor.

"COPD" refers to chronic obstructive pulmonary disease.

"CryoTEM" refers to cryogenic transmission electron microscopy.

"DLS" refers to dynamic light scattering.

"DMF" refers to dimethylformamide.

"DOPE" refers to 1,2-dioleoyl-sn-glycero-3-phosphoethanolamine.

"DSPC" refers to 1,2-distearoyl-sn-glycero-3-phosphocholine.

"DSPE" refers to 1,2-distearoyl-sn-glycero-3-phosphoethanolamine.

"FFPE" refers to formalin-fixed paraffin-embedded.

"Fluc" refers to firefly luciferase.

"FRET" refers to fluorescence resonance energy transfer.

"H&E" refers to hematoxylin and eosin.

"HEPES" refers to 4-(2-hydroxyethyl)-1-piperazineethanesulfonic acid.

"ISH" refers to in situ hybridization; LNP, lipid nanoparticle.

"MAP" refers to microfluidic aerosolization platform.

"NBD" refers to 7-nitrobenzo-2-oxa-1,3-diazole.

"Nluc" refers to nanoluciferase.

"PBS" refers to phosphate buffered solution.

"PDI" refers to polydispersity index;

"PEG" refers to polyethylene glycol.

"POPC" refers to 1-palmitoyl-2-oleoyl-sn-glycero-3-phosphocholine.

"Rho" refers to rhodamine B.

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The description herein is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figures. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A low shear microfluidic aerosolization system for delivery of a therapeutic media into a pulmonary airway, the system configured to maintain droplet size and preserve mRNA encapsulation, the system comprising:
   a microfluidic chip having a plurality of microfluidic chambers and corresponding apertures, the microfluidic chip having a width of from about 3 mm to 5 mm, and wherein the plurality of microfluidic chambers comprises about 100 or more microfluidic chambers;
   a plurality of heat sources comprising resistors in thermal communication with each of the plurality of microfluidic chambers, the resistors in communication with circuitry to allow each of the plurality of microfluidic chambers to be individually addressable for drop ejection;
   a cartridge housing the microfluidic chip and multiple reservoirs holding the therapeutic media configured to deliver the therapeutic media into the plurality of microfluidic chambers, the therapeutic media comprising mRNA encapsulated within lipid nanoparticles;
   and a processor, configured to separately control each of the plurality of heat sources to generate an activation pulse heating pattern, wherein the processor executes programming to apply an electrical potential to each of the heat sources, the electrical potential being less than about 5V and having a pulse width of less than about 10 µs;
   wherein the plurality of microfluidic chambers express a plurality of droplets in response to the activation pulse heating pattern, wherein sizes of the lipid nanoparticles are substantially the same before and after expression, the plurality of droplets having diameters ranging from 7.3 µm to 24.4 µm after expression, and wherein the microfluidic aerosolization system is configured to preserve encapsulation of over 43% of the mRNA during expression of the plurality of droplets from the plurality of microfluidic chambers.

2. The microfluidic aerosolization system of claim 1, wherein the microfluidic chip is monolithically fabricated on a silicon base layer.

3. The microfluidic aerosolization system of claim 2, wherein the activation pulse heating pattern has a timing range from about 0.1 microseconds to about 10 microseconds.

4. The microfluidic aerosolization system of claim 1, wherein the activation pulse heating pattern has a frequency of at least about 10 kHz.

5. The microfluidic aerosolization system of claim 1, wherein the plurality of microfluidic chambers express the plurality of droplets at a rate of at least about 5 million drops per second.

6. The microfluidic aerosolization system of claim 1, comprising at least about 500 microfluidic chambers and corresponding apertures.

7. The microfluidic aerosolization system of claim 1, wherein at least some of the corresponding apertures have a diameter of no more than about 15 microns.

8. The microfluidic aerosolization system of claim 1, wherein the cartridge contains a volume of the therapeutic media in the one or multiple reservoirs.

9. The microfluidic aerosolization system of claim 8, wherein the processor is configured to deliver the volume of therapeutic media broken into a plurality of individual patient doses.

10. The microfluidic aerosolization system of claim 1, wherein the cartridge includes at least two reservoirs.

11. The microfluidic aerosolization system of claim 10, wherein a first reservoir carries a first therapeutic media and a second reservoir carries a second therapeutic media.

12. The microfluidic aerosolization system of claim 10, wherein each reservoir carries the same therapeutic media.

13. The microfluidic aerosolization system of claim 10, wherein at least one reservoir carries a buffer.

14. The microfluidic aerosolization system of claim 1, wherein all the corresponding apertures can be individually programmed using the activation pulse heating pattern in order to control at least one of a drop size, a drop size composition, a drop ejection frequency, and a drop volume.

15. The microfluidic aerosolization system of claim 1, wherein the processor is configured for simultaneous or sequential activation of the plurality of microfluidic chambers and corresponding apertures.

16. The microfluidic aerosolization system of claim 1, further comprising a mouthpiece having a profile that is matched to the microfluidic chip size to influence the shape of the plume as it is being ejected from the corresponding apertures.

17. The microfluidic aerosolization system of claim 1, wherein an applied voltage and pulse width results in the formation of a microbubble which nucleates, expands and collapses to eject a droplet of fluid in each of the plurality of microfluidic chambers.

18. The microfluidic aerosolization system of claim 17, wherein the applied voltage comprises a waveform that is square, saw tooth, or sinusoidal.

19. The microfluidic aerosolization system of claim 17, wherein the applied voltage and pulse width results in a deflection of a micro-electro-mechanical membrane, which ejects the droplet of fluid in the microchamber.

20. The microfluidic aerosolization system of claim 1, wherein each of the plurality of individual chamber addressing pattern and ejection frequency are adjustable to regulate the plurality of droplets into a plume formation, the depth of droplet penetration into the pulmonary airway and agglomeration of droplets in the plume.

21. The microfluidic aerosolization system of claim 1, wherein, before expression of the plurality of droplets from the microfluidic chambers, the sizes of the lipid nanoparticles is about 100 nm.

\* \* \* \* \*